United States Patent
Williams et al.

(10) Patent No.: US 9,506,035 B2
(45) Date of Patent: Nov. 29, 2016

(54) METHODS AND COMPOSITIONS TO SUPPORT TRANSPLANTED TISSUE INTEGRATION AND INNOSCULATION WITH ADIPOSE STROMAL CELLS

(75) Inventors: Stuart K. Williams, Harrods Creek, KY (US); James Beatty Hoying, Louisville, KY (US); Laxminarayanan Krishnan, Louisville, KY (US)

(73) Assignee: University of Louisville Research Foundation, Inc, Louisville, KY (US)

( * ) Notice: Subject to any disclaimer, the term of this patent is extended or adjusted under 35 U.S.C. 154(b) by 0 days.

(21) Appl. No.: 13/502,090

(22) PCT Filed: Oct. 13, 2010

(86) PCT No.: PCT/US2010/052496
§ 371 (c)(1),
(2), (4) Date: Apr. 19, 2012

(87) PCT Pub. No.: WO2011/047040
PCT Pub. Date: Apr. 21, 2011

(65) Prior Publication Data
US 2012/0201890 A1    Aug. 9, 2012

Related U.S. Application Data

(60) Provisional application No. 61/251,060, filed on Oct. 13, 2009.

(51) Int. Cl.
| | |
|---|---|
| *A61K 35/39* | (2015.01) |
| *C12N 5/071* | (2010.01) |
| *A61K 35/28* | (2015.01) |
| *A61K 35/34* | (2015.01) |
| *A61K 35/35* | (2015.01) |
| *A61K 35/44* | (2015.01) |

(52) U.S. Cl.
CPC ............. *C12N 5/0677* (2013.01); *A61K 35/28* (2013.01); *A61K 35/34* (2013.01); *A61K 35/35* (2013.01); *A61K 35/39* (2013.01); *A61K 35/44* (2013.01); *C12N 2502/1305* (2013.01)

(58) Field of Classification Search
None
See application file for complete search history.

(56) References Cited

FOREIGN PATENT DOCUMENTS

WO    00-62794 A1    10/2000

OTHER PUBLICATIONS

Kang et al., Porous Poly(Lactic-Co-Glycolic Acid) Microsphere as Cell Culture Substrate and Cell Transplantation Vehicle for Adipose Tissue Engineering, Tissue Engineering, vol. 14, Issue 1, Mar. 18, 2008.*
Gimble et al., Adipose-Derived Stem Cells for Regenerative Medicine, Circulation Research 100:1249-1260 (2007).*
Shepherd et al., Rapid Perfusion and Network Remodeling in a Microvascular Construct After Implantation, Arterioscler Thromb Vasc Biol, May 2004.*
PCT/US2010/052496 International Patent Application No., International Search Report mailed Jun. 29, 2011; 5 pages.
PCT/US2010/052496 International Patent Application No., International Preliminary Report on Patentability and Written Opinion mailed Jun. 28, 2011; 7 pages.
Figliuzzi, M., et al., "Bone Marrow-Derived Mesenchymal Stem Cells Improve Islet Graft Function in Diabetic Rats" Transplantation Proceedings, Jun. 2009, vol. 41, No. 5, pp. 1797-1800.
Fumimoto, Y., et al., "Creation of a Rich Subcutaneous Vascular Network with Implanted Adipose Tissue-derived Stromal Cells and Adipose Tissue Enhances Subcutaneous Grafting of Islets in Diabetic Mice." Sep. 2009, Tissue Eng. Part C Methods, vol. 15, No. 3, pp. 437-444.
Teramura, Y., et al., "Islet Encapsulation with Living Cells for Improvement of Biocompatibility" Biomaterials, Apr. 2009, vol. 30, No. 12, pp. 2270-2275.

* cited by examiner

*Primary Examiner* — Suzanne M Noakes
*Assistant Examiner* — Stephen Chong

(57) ABSTRACT

The present invention generally relates to methods, compositions and uses thereof for enhancing vascularization of a tissue or cell transplant for transplantation into a subject. In particular, one aspect of the present invention provides methods and compositions comprising the use of a population of stromal vascular fraction (SVF) cells to encapsulate or surround a tissue or cell transplant to enhance vascularization of the tissue or cell transplant. Another aspect of the present invention provides methods and compositions for enhancing vascularization of a tissue or cell transplant by combining a population of SVF cells with a tissue or cell transplant to form a transplant mixed with SVF cells. In some embodiments, the SVF cells can be on the surface or embedded within a three-dimensional matrix. In some embodiments, the SVF cells can be generically engineered to secrete therapeutic proteins or pro-angiogenic factors.

8 Claims, 3 Drawing Sheets

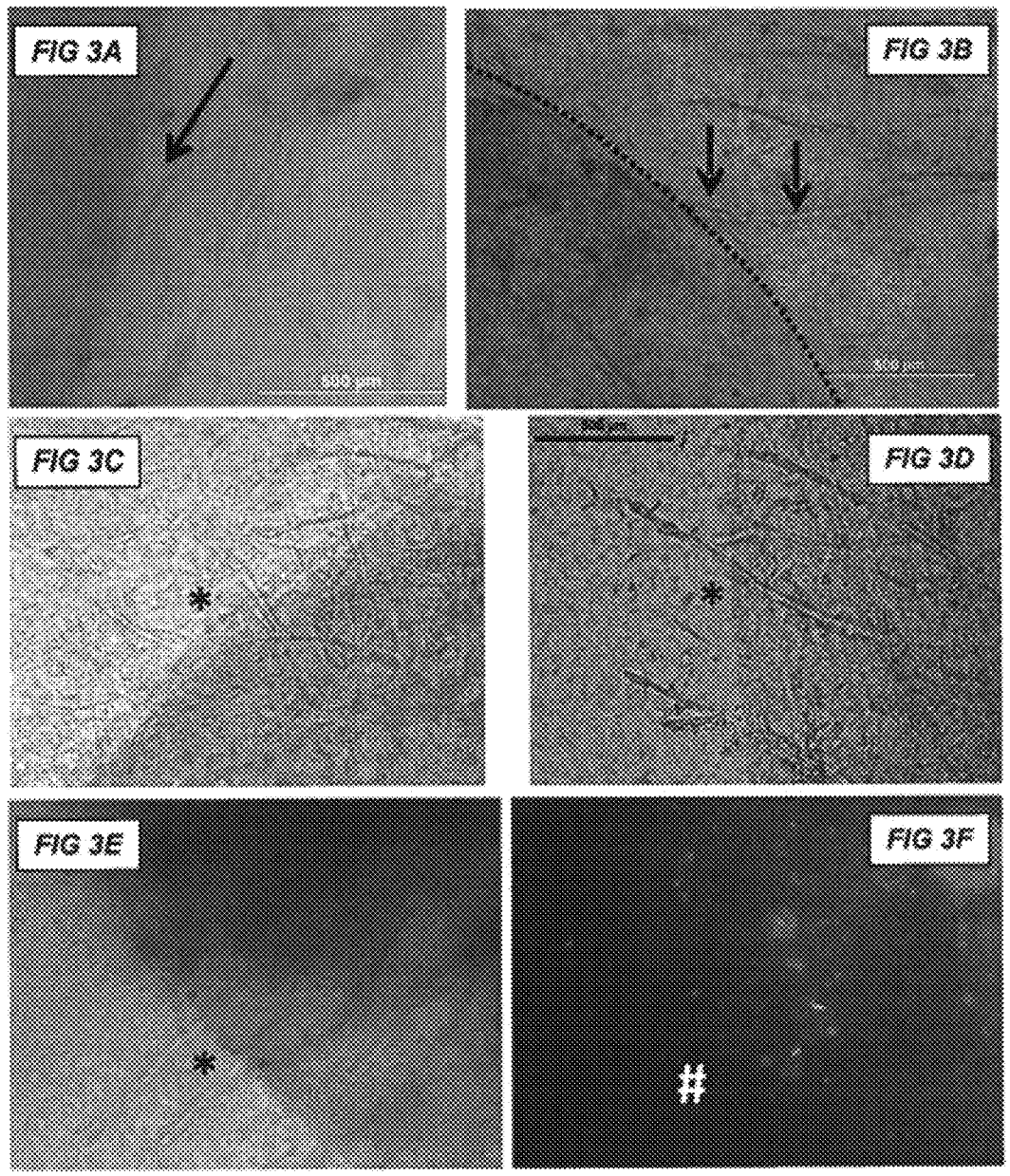

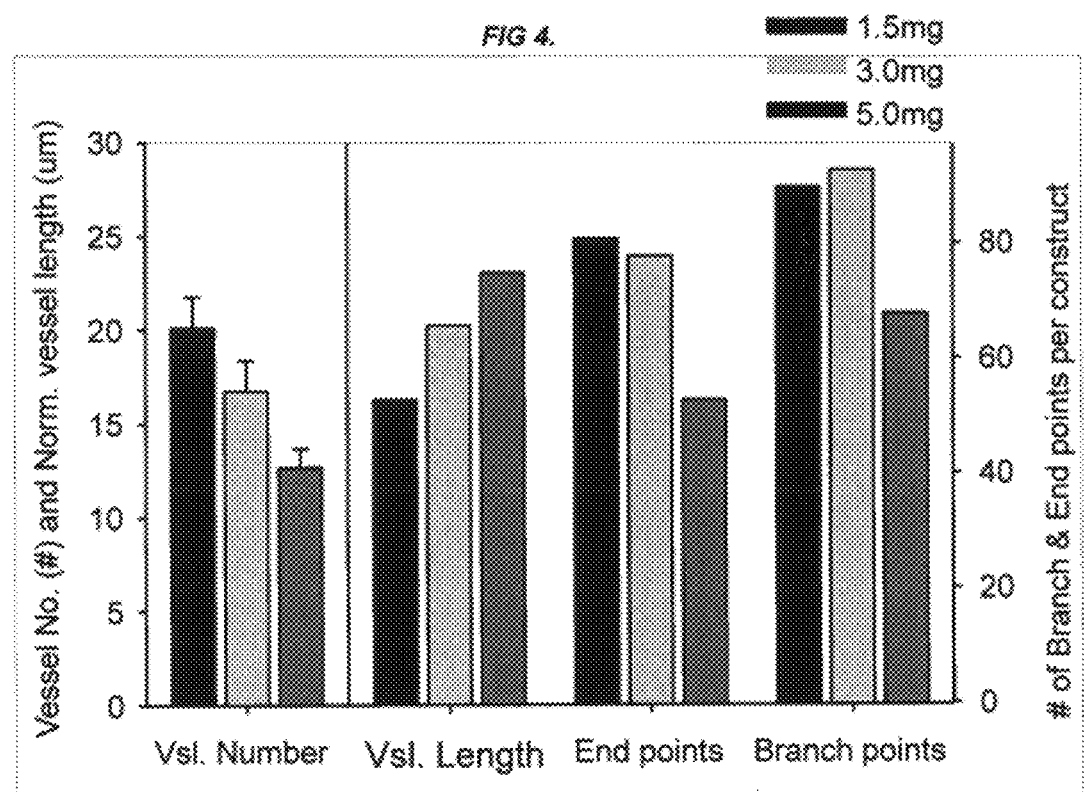
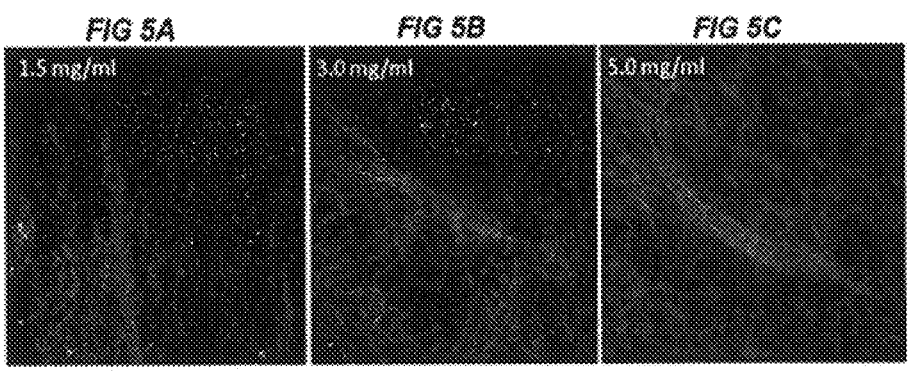

METHODS AND COMPOSITIONS TO SUPPORT TRANSPLANTED TISSUE INTEGRATION AND INNOSCULATION WITH ADIPOSE STROMAL CELLS

CROSS REFERENCE TO RELATED APPLICATIONS

This application is a National Phase Entry application under 35 U.S.C. §371 of International Application No. PCT/US2010/052496 filed on Oct. 13, 2010, which designates the United States, and which claims benefit under 35 U.S.C. 119(e) of U.S. Provisional Patent Application Ser. No: 61/251,060 filed 13 Oct. 2009, the contents of which are incorporated herein by reference in their entirety.

GOVERNMENT INTEREST

The present invention was made with United States Government support under Grant No. DK078175, awarded by the National Institutes of Health. The government has certain rights in this invention.

FIELD OF THE INVENTION

The present invention relates to the field of tissue, organ and cell transplantation. Methods and compositions are provided to improve integration, particularly through improved vascularization of a transplanted tissue, organ or cell into a host recipient.

BACKGROUND OF THE INVENTION

Transplants of cells and tissue engineered organs and tissues offer promise in facilitating tissue healing and repair and the replacement or treatment of diseased or dysfunctional organs. According to data from the American Association of Tissue Banks (AATB), a voluntary accreditation organization that sets standards for tissue banking, approximately 1.5 million bone and tissue allografts are distributed each year by AATB-accredited tissue banks in the United States. In the U.S., around 20,000 organ transplants are performed yearly, and the list of individuals in need of tissue and organ transplants is even increasing.

A primary challenge in the transplantation of tissues, organs, cells or an artificially created engineered tissue constructs is ensuring sufficient blood supply to the transplanted tissue and cells. In the absence of pre-existing vessels in the transplant capable of inosculation with the recipient blood supply, the amount of tissue that can be transplanted into a subject is limited by oxygen diffusion.

Ultimately, healthy transplants depend on sufficient vessel density within the transplanted tissue or organ and the organization of the vessels into a network comprised of low-resistance conduit vessels (arteries), a functional microcirculation (arterioles and capillaries) for a proper blood-tissue exchange, and drainage/compliance vessels (venules and veins).

Existing strategies for building a vascular system for tissue engineered constructs have been based on using cultured, human endothelial cells. For example, preparation of pre-formed vascular beds such as prevascularized constructs can be attached or incorporated at the tissue, organ or cell transplant interface at the time of transplantation as previously described in U.S. Pat. No. 7,052,829. However, growing such constructs is labor intensive and requires time for the prevascularized constructs to grow, which is not a possibility when it is necessary to transplant donated tissues, organs and cells within hours of removal of the organ, tissue or cell from a donor, or where the recipient is in need of an immediate cell or organ transplantation.

Additionally organs such as heart, kidneys, liver, lungs, pancreas, and intestines, and heart and lung transplants can be transplanted as whole organs. Many classifications of tissue may also be transplanted including whole eyes or corneas, heart valves, cardiovascular tissue, which includes the thoracic aorta, the abdominal aorta with iliac arteries, saphenous veins, and femoral vessels, may be donated to restore compromised blood circulation. Bone and soft musculoskeletal tissue, such as ligaments, are also suitable for transplantation for orthopedic and spinal surgeries and sports medicine injuries. Skin can be transplanted to promote healing and prevent infection in critically burned individuals, as well as whole, or partial face transplants for recipients who have severe facial deformities due to a previous injury. It is imperative that such large tissue and organ transplants are have sufficient blood supply to prevent atrophy of the transplanted tissue and integration into the recipients existing tissue.

Accordingly, improved methods for increasing vascularization of transplants such as donated and engineered tissues, cells and organs are needed.

SUMMARY OF THE INVENTION

The present invention provides methods and compositions to significantly increase the efficiency of tissue, organ and cell integration to its new environment. The invention is based on a discovery that a cell population, obtained from adipose tissue following tissue dissociation, accelerates and stimulates the integration of transplanted tissue, organ or cell into a host. The cell population is referred to herein as the stromal vascular fraction (SVF). In one embodiment, the transplant is a donated tissue, organ or cell. In another embodiment, the transplant is an engineered tissue or organ construct.

The methods and compositions as disclosed herein overcome a major obstacle in transplantation treatments, namely, the slow integration of transplanted tissue, organ, cell or tissue engineered construct into host tissue following transplantation. The methods and compositions as disclosed herein accelerate migration of microcirculation elements (small blood vessels) out of the transplanted tissue into recipient tissue. The accelerate migration of microcirculation elements (small blood vessels) results in accelerated restoration of blood flow to the transplanted tissue due to accelerated tissue integration.

Accordingly, one embodiment of the invention provides a method for enhancing a transplant integration into a recipient subject, where a composition comprising mixing a population of SVF cells present within a three-dimensional matrix, e.g., a gel, that comprises other cells, such as vascular fragments isolated from adipose tissue according to methods described in U.S. Pat. Nos. 7,052,829 and 7,029,838, or tissues such as islets as described in U.S. patent application publication No. 2006/0188488, and inserting three-dimensional matrix, e.g., gel, comprising SVF cells into the transplant host interface in a transplant recipient. In some embodiments, the transplant recipient is preferably human.

One aspect of the present invention is directed to the use of a three-dimensional matrix, e.g., a gel mixed with SVF cells for enhancing transplant integration in a subject in need of a tissue, organ and/or cell transplant.

In another embodiment, the invention provides a method for treating an external surface of a transplant or an external surface of three-dimensional matrix, e.g., a gel intended to be inserted into the transplant/host interface with the SVF cells. In one embodiment, the SVF cells are genetically engineered.

In one embodiment, the SVF cells are derived from the recipient which receives the transplanted tissue, and therefore the SVF cells are autologous, thus having an additional advantage of reducing graft-versus-host disease. In some embodiments, the SVF cells are derived from a donor, which can be either the transplant donor or a different donor.

One aspect of the present invention is directed to the use of a three-dimensional matrix, e.g., a gel, where the surface of the three-dimensional matrix has been externally treated with SVF cells for increasing transplant integration.

In one embodiment, the methods and compositions as disclosed herein are useful to assist a tissue engineered construct to integrate into a host.

One aspect of the present invention provides a method of enhancing vascularization of a tissue or cell transplant in a subject, comprising; (a) encapsulating the tissue or the cell transplant with a population of stromal vascular fraction (SVF) cells; (b) implanting the tissue or the cell transplant encapsulated with a population of stromal vascular fraction (SVF) cells into a subject, wherein the SVF enhances vascularization of the tissue or the cell transplant in the subject.

In some embodiments, the population of SVF cells are present on the surface of, or embedded within, a biocompatible three-dimensional culture matrix, and in some embodiments, the biocompatible three-dimensional culture matrix comprises additional cells, for example, microvessel fragments. In some embodiments, the microvessel fragments are obtained from adipose tissue.

In some embodiments, the tissue or cell transplant encapsulated with SVF cells is present on the surface of, or embedded within, a biocompatible three-dimensional culture matrix, and in some embodiments, the matrix further comprises microvessel fragments. In some embodiments, the three-dimensional culture matrix does not comprise other types of cells or tissue fractions than SVF cells.

In some embodiments, the SVF cells are directly or indirectly contact tissue or cell transplant.

In some embodiments, the SVF cells are obtained from the subject, for example a tissue or cell transplant donor. In some embodiments, the SVF cells and the tissue or cell transplant are from different subject species. In some embodiments, the SVF cells are human SVF cells. In some embodiments, the tissue or cell transplant is mammalian, e.g., human. In some embodiments, the SVF cells and/or tissue or cell transplant are genetically engineered. In some embodiments, the SVF cells are attached to a tissue or cell transplant, e.g. by suturing, stapling, gluing and combinations thereof.

In some embodiments, the SVF cells are a substantially pure population of SVF cells, for example, derived from human adipose tissue.

Another aspect of the present invention provides, a method of enhancing vascularization of a tissue or cell transplant in a subject, comprising; (a) combining a population of stromal vascular fraction (SVF) cells with tissue or cell transplant to form a transplant mixed with SVF cells, (b) implanting the transplant mixed with SVF cells into the subject, wherein the SVF cells enhance the vascularization of the tissue or cell transplant in the subject.

In some embodiments, a transplant, e.g., cell transplant can be mixed with SVF cells to produce a heterogeneous mixed population SVF cells with a tissue or cell transplant. In some embodiments, a population of SVF cells are a substantially pure population of SVF cells. In some embodiments, a transplant mixed with SVF cells is present on the surface of, or embedded within a three-dimensional biocompatible matrix, which can optionally comprise additional populations of cells. In some embodiments, a transplant mixed with SVF cells does not comprise microvessel fragments, or does not comprise other types of cells or tissue fractions other than SVF cells and cell transplant cells. In some embodiments, a transplant mixed with SVF cells is present on the surface of, or embedded within a biocompatible three-dimensional culture matrix is combined with a tissue, organ or cell mass to be transplanted.

Another aspect of the present invention relates to a composition comprising a tissue or cell transplant and a population of stromal vascular fraction (SVF) cells, wherein the population of SVF cells are attached to the outer surface of the tissue or cell transplant. In some embodiments, the population of SVF cells is a single cell layer or a multiple cell layer. In some embodiments, the population of SVF cells is present on the surface of, or embedded within a three-dimensional matrix.

In some embodiments, the a single cell layer or a multiple cell layer of SVF cells, or a population of SVF cells on a three-dimensional matrix substantially covers the outer surface of the tissue or cell transplant, for example by about at least 50%, or at least about 60%, or at least about 70%, or at least about 80%, or at least about 90%, or at least about 100% or any integer inbetween 50-100%. Another aspect of the present invention relates to the use of the composition comprising a tissue or cell transplant and a population of stromal vascular fraction (SVF) cells, wherein the population of SVF cells are attached to the outer surface of the tissue or cell transplant for transplantation into a subject in need of a tissue or cell or organ transplantation.

BRIEF DESCRIPTION OF DRAWINGS

FIG. 1A shows a freshly isolated vessel fragment. FIG. 1B shows a "sprout" formation at day 4.

FIGS. 2A-2D shows vascularization of mixture of islet and microvessel fragments. FIG. 2A shows India ink perfused islets showing ink within islet mass, shown by (*) (×10 magnification). FIG. 2B shows dextran perfusion image (×20) showing the outline of vessels (*) associated with the islet and islet perfusion. The dotted line denotes the boundary between the two vascularized gels. The arrow denotes a vessel approaching the interface and being defected. FIG. 2C shows an image of islet core showing India ink (×20). No central necrosis is evident. FIG. 2D shows GFP islets in the constructs of collagen and microvessels and islets. (×20).

FIGS. 3A-3F show improved vascularization of microvessel fragments in the presence of SVF cells. FIG. 3A shows defected vessel spouts at the boundary with a gluteraldehyde fixed collagen gel (arrow) on the left. FIG. 3B shows sprout deflection at the interface (dotted line) between a vascularized core and vascularized exterior (arrow). FIG. 3C shows an image of vessel sprouts across (*) the interface with addition of SVF (×10). FIG. 3D shows an image of vessel sprouts across (*) the interface with addition of SVF (×20). FIG. 3E shows an image of vessel sprouts across (*) the interface with SVF cells labeled with PHK26 (×10). FIG. 3F shows a similar image to that of 3E, with the PHK26 labeled SVF cells visible. Vessels were not treated with PHK26 and do not stain (#), demonstrating the permissive nature of SVF cells to enhance and accelerate vascularization of microvessel fragments.

FIG. 4 shows the number of vessels>150 μm, Median vessel lengths normalized to vessel number and Total branch and end-points per construct over increasing ECM density, such as at 1.5 mg/ml, 3.0 mg/ml and 5.0 mg/ml collagen density.

FIGS. 5A-5C show Collagen fibril alignment around neovessel sprouts. FIG. 5A shows collagen fibril alignment at 1.5 mg/ml collagen density, FIG. 5B shows collagen fibril alignment at 3.0 mg/ml collagen density, and FIG. 5C shows collagen fibril alignment at 5.0 mg/ml collagen density. The orientation field extends to a larger distance in weaker matrix.

DETAILED DESCRIPTION OF THE INVENTION

Figure 1:
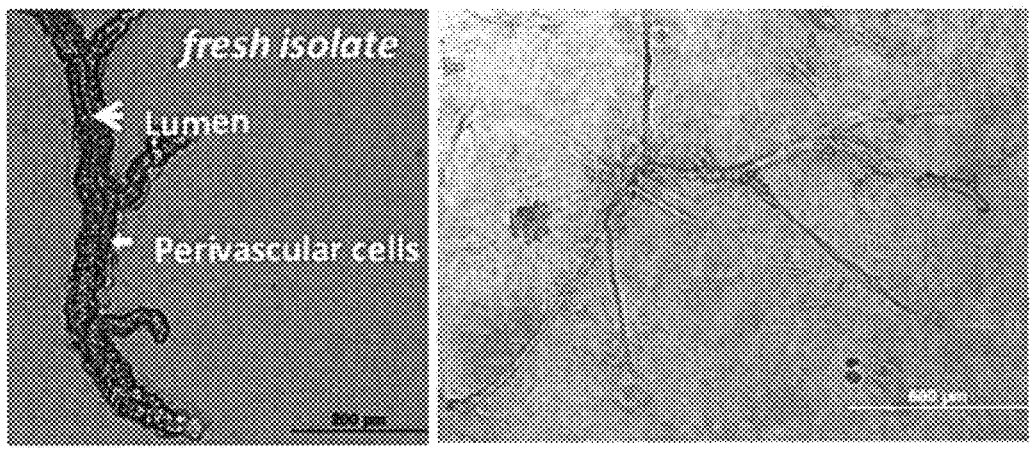
FIGS. 1A-1B shows vascularization of collagen seeded with microvessel fragments.
Figure 1:
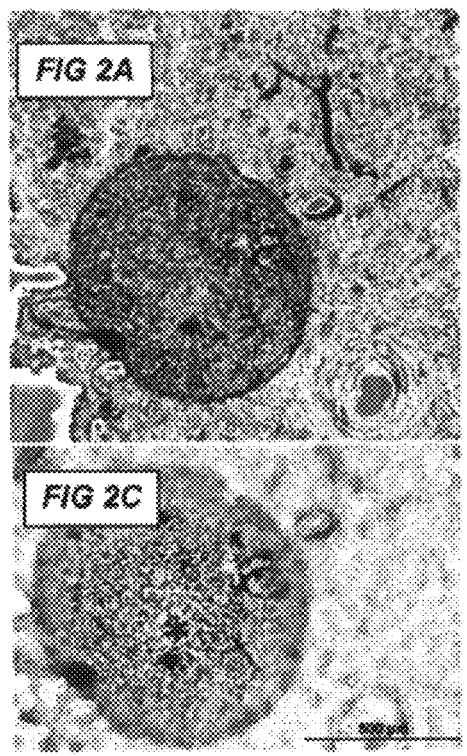
Figure 1:
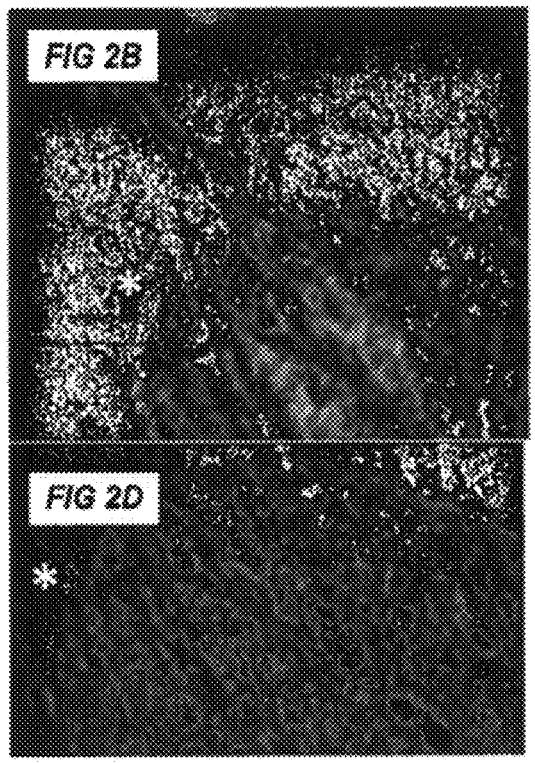

The section headings used herein are for organizational purposes only and are not to be construed as limiting the subject matter described. All references cited in this application are expressly incorporated by reference for any purpose.

Adequate vascularization of tissue-engineered constructs is a critical step in the integration of implants with the host tissue. The regulation of neovessel sprouting is closely related to extracellular matrix signals like stiffness and matrix fiber orientation. These conditions are typically encountered when neovessel sprouts traverse the boundary between different tissue structures, or at the interface of the host and implanted tissue, and can determine the fate of neovessel sprouts at such boundaries.

Several studies have addressed strategies to improve vascularization of implanted tissue, but the boundary between the host and implant is not well investigated as a possible barrier to neovascularization.

The present inventors studies models of such an interface in vitro, using a vascularized collagen construct based on adipose derived microvessels at the core, surrounded by cell free collagen on the sides. Though angiogenesis in the core of such models progress to form well interconnected networks, neovessels traversing the interface by themselves are infrequent.

The inventors discovered that addition of stromal vascular fraction cells derived from adipose tissue in addition to the microvessels significantly increases the number of neovessels growing across the boundary.

Unlike the methods described in the U.S. Pat. Nos. 7,029,838 and 7,052,829 (referred to herein as the '838 and '829 patents respectively), wherein microvessel fragments present within a three-dimensional matrix form a separate vascular structure which is grown for at least 7-10 days to form a new microvascular (capillary) bed, and forms an independent structure referred to as an "engineered prevascularized construct" which is then affixed and transplanted together with a tissue-engineered construct, the present invention herein provides a method and constructs where no pre-growth of the capillary bed is necessary. Accordingly, one advantage of the present method and composition is that it combines a population of SVF cells with the transplanted tissue or cells to greatly enhance and accelerate the vascularization of the transplanted tissue and cells. Thus, unlike the methods of the '838 patent, the present methods and compositions as disclosed herein are more suitable for real life organ and tissue donor situations where time is of the essence, and there is not sufficient time to allow for pre-growth of the capillary bed. Also, unlike the U.S. Pat. No. 7,052,829 where freshly isolated microvessel constructs comprising microvessel fragments are used, in some embodiments the methods and compositions as disclosed herein do not comprise microvessel constructs.

Also, unlike the methods and compositions of the '829 patent, an additional advantage of the methods and compositions as disclosed herein is that SVF cells can be used to encapsulate (e.g. encase or surround) the tissue and/or cell transplant to promote revascularization of a tissue or cell transplant. In some embodiments, the encapsulating population of SVF cells can be a single or multiple cell layer which encapsulates the tissue or cell population. In alternative embodiments, an encapsulating population of SVF cells can be in the presence (e.g. on the surface of, or embedded within) a three-dimensional matrix. In some embodiments, the encapsulating population of SVF cells can also be in the presence or absence of microvessel fragments, where in some embodiments, the microvessel fragments can be present on the surface of, or embedded within a three-dimensional matrix with the SVF cells. In some embodiments, the three-dimensional matrix comprising an encapsulating population of SVF cells does not comprise microvessel fragments. In alternative embodiments, the microvessel fragments can be mixed among the population of cells to be transplanted, which in turn is encapsulated with the encapsulating population of SVF cells.

Without wishing to be bound by a theory, the inventors demonstrate herein that the presence of SVF cells performs both regulatory modulation of existing neovessels and incorporation of neovessel sprouts into the transplanted cells or tissue. The inventors also demonstrate herein that the presence of SVF's also has a pro-angiogenic role. Further, collagen at the interface between the cell free periphery and the vascularized-cellular core remains relatively well-defined, demonstrating that any matrix remodeling by the SVF cells is a highly localized phenomenon. This is an important feature because it demonstrates that neovascularization of the transplanted cells or tissue is localized and does not provide uncontrolled vascular growth elsewhere in the body, demonstrating that the use of SVF cells will be safe where it is desirable to transplant into a human subject.

Additionally, the absence of any conspicuous pooling of SVF cells at the interfacial surface between the transplanted tissue or cells and the surrounding recipient tissue also demonstrates a pro-angiogenic and regulatory role for the SVFs, and demonstrates that the role of SVFs is not limited to matrix remodeling at the interface, but rather SVFs promote a higher invasion of angiogenic sprouts into the surrounding tissue.

One aspect of the present invention provides methods and compositions comprising a population of SVF cells in combination, such as mixed in, within tissue cells or cells to be transplanted into a subject to form what is referred to herein as a "transplant mixed with SVF cells". In such embodiments, a population of SVF cells can be combined with a population of cells to be transplanted in a three-dimensional matrix, such as a gel as disclosed herein. In some embodiments, the transplant mixed with SVF cells, (e.g. a heterologous mixture of a population of SVF cells and a population of cells of interest to be transplanted) can include additional populations of cells. In some embodiments a transplant mixed with SVF cells includes additional populations of cells, where the additional cells are not microvessel fragments. Alternatively, in some embodiments where a three dimensional matrix is not used, a transplant mixed with SVF cells can also include microvessel fragments.

In some embodiments, a transplant mixed with SVF cells is administered to a subject by injection, independent of whether the transplant mixed with SVF cells is present on the surface of, or embedded within a three-dimensional matrix. In some embodiments, a transplant mixed with SVF cells is administered to a subject by surgical procedures commonly known by a skilled artisan.

Another aspect of the present invention relates to the use of SVF cells to promote vascularization of a tissue or cell transplant to be transplanted into a subject. In embodiments of this aspect of the invention, a population of SVF cells can encapsulate (e.g. surround or cover the surface of) a tissue or cell transplant. In some embodiments, the tissue or cell transplant is a tissue engineered tissue, or the like. In some embodiments, the tissue or cell transplant can be on the surface of, or embedded within a three-dimensional matrix as that term is defined herein.

In some embodiments, where the tissue or cell transplant is present on the surface of, embedded within a three-dimensional matrix, and is encapsulated with a population of SVF cells, the three-dimensional matrix can further comprise microvessel fragments.

In some embodiments, a population of SVF cells which encapsulates the tissue or cell population is a single or multiple cell layer of SVF cells, which can partially or substantially encapsulate (e.g. surround or cover the surface of) the tissue or cell transplant.

In an alternative embodiment, a population of SVF cells is present on the surface of, or embedded within a three-dimensional matrix to form what is referred to herein as a "SVF-matrix construct", where the SVF-matrix construct can partially or substantially encapsulate (e.g. surround or cover the surface of) the tissue or cell transplant to be transplanted. In some embodiments, the SVF-matrix can also comprise additional cell types, for example, microvessel fragments. In some embodiments, such a SVF-matrix is combined with the tissue or cell population to be transplanted by placing and affixing the SVF-matrix to the surface of the tissue or cell population to be transplanted.

Another aspect of the present invention relates to a composition comprising a tissue or cell construct which is partially or substantially encapsulated (e.g. covered or surrounded) with a population of SVF cells. In some embodiments, the population of SVF cells is directly or indirectly attached to the outer surface of the tissue or cell transplant. In some embodiments, the population of SVF cells is in contact with the outer surface of the tissue or cell transplant. In some embodiments, the SVF cells are present on the surface of, or embedded within a three-dimensional matrix to form a SVF-matrix as disclosed herein, or in alternative embodiments, the SVF cells can be present as a single cell layer or multiple cell layer on the surface of the tissue or cell transplant. In some embodiments, the SVF cells cover at least about 50% of the outer surface of tissue or cell transplant, for example, at least about 50%, or at least about 60%, or at least about 70%, or at least about 80%, or at least about 90%, or greater than 90% of the outer surface of tissue or cell transplant. In some embodiments, the SVF cells cover at least about 80%-100%, or any integer inbetween, of the outer surface of tissue or cell transplant.

In some embodiments, the use of SVF cells according to the methods and compositions as disclosed herein can be used to enhance the vascularization of tissues and cells transplants, such as, for example, but not limited to tissues and cell transplants comprising cells from Bone, Fat, Islets, Parathyroid, Liver, Spleen, Cardiac Muscle, Skeletal Muscle, Blood Vessels, Cornea, Trabecular Meshwork, Lung tissue, Lymph tissue, Tissue Engineered Tissue, Regenerative Cells, and Stem Cells. In some embodiments, the SVF cells can be used to enhance vascularization of tissues and cells transplants which are tissue engineered tissue. In some embodiments, the tissues and cells transplants are genetically engineered tissue and cell transplants In some embodiments, the methods and compositions as disclosed herein, e.g. a tissue or cell transplant encapsulated in a population of SVF cells, or a transplant mixed with SVF cells can be inserted into a host, for example in all Muscles, Liver, Lung, Subcutaneous Fat, Peritoneal Space, Sphincters (all types), Trachea, Brain, Pancreas, Skin, Eye, and intravascular, intracoronary, intra-arterial sites, as well as bone surfaces.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention which will be limited only by the appended claims.

The term "stromal vascular fraction cells" or "SVFs" are used interchangeably with "Adipose-derived stromal cells" or "ASCs", and refer to adult cells that originate from adipose tissue. Stromal vascular fraction cells is a heterologous population of cells comprising at least one or at least 2 or the following population of cells; endothelial cells, mesenchymal stem cells, fibroblasts, smooth muscle cells, pericytes and adipose-derived stem cells, as well as additional other cell types not listed. In some embodiments, the stromal vascular fraction (SVFs) refers to a substantially pure population of adipose-derived stem cells. In some embodiments, stromal vascular fraction cells does not refer to adipose derived regenerative cells. Stromal vascular fraction cells (SVFs) can be easily harvested from adipose tissue and are substantially free of adipocytes and red blood cells and clonal populations of connective tissue stem cells. The stromal vascular fraction cells are substantially devoid of cells, which includes extracellular matrix material from adipose tissue.

The term "adipose" as used herein refers to any fat tissue from a subject. The terms "adipose" and "adipose tissue" are used interchangeably herein. The adipose tissue may be brown fat, white fat or yellow fat or white adipose tissue, derived from subcutaneous, omental/visceral, mammary, gonadal, or other adipose tissue site. The adipose tissue has adipocytes and stroma. Adipose tissue is found throughout the body of an animal. For example, in mammals, adipose tissue is present in the omentum, bone marrow, subcutaneous space and surrounding most organs. Preferably, the adipose is subcutaneous white adipose tissue. Such cells may comprise a primary cell culture or an immortalized cell line. The adipose tissue may be from any organism having fat tissue. Preferably, the adipose tissue is mammalian, most preferably, the adipose tissue is human. A convenient source of adipose tissue is from liposuction surgery, however, the source of adipose tissue or the method of isolation of adipose tissue is not critical to the invention.

The term "transplant mixed with SVF cells" refers to a combination of SVF cells and tissue or transplant cells. In some embodiments, a transplant mixed with SVF cells can comprise additional cells. In some embodiments, a transplant mixed with SVF cells can be present on the surface of, or embedded within a three-dimensional matrix. In some embodiments, where a transplant mixed with SVF cells also comprises a three-dimensional matrix, it does not comprise microvessel fragments.

The term "transplant encapsulated with SVF cells" refers to a composition comprising a tissue or cell transplant which is surrounded, partially or substantially, with SVF cells, where the SVF cells are present as a single or multiple cell layer or as a SVF-matrix.

The term "SVF-matrix" refers to a composition comprising a population of SVF cells and a three-dimensional matrix, wherein the SVF cells are on the surface or embedded within the three-dimensional matrix. In general, the SVF-matrix is used to encapsulate the tissue or cell transplant. In some embodiments, the SVF-matrix can comprise other cells, including in some embodiments microvessel fragments. In some embodiments, the SVF-matrix does not comprise transplant cells.

The term "tissue" as used herein is a broad term that is applied to any group of cells that perform specific functions, and includes in some instances whole organs (e.g. parathyroid) and/or part of organs, such as pancreatic islets. A tissue need not form a layer, and thus encompasses a wide range of tissue including bone marrow, skin, connective tissue (e.g. cells that make up fibers in the framework supporting other body tissues); and hematopoietic and lymphoid tissue (e.g. cells which function as part of the body's immune system that helps protect it from bacteria and other foreign entities).

The term "cell transplant" as used herein refers to a population of cells or cell mass for transplantation into a subject. A cell transplant can comprise genetically modified cells, as well as cells differentiated from other cells, such as stem cells, progenitors, iPS cells and the like. The population of cells which make up a cell transplant are referred to as "transplant cells" or "cell transplant cells".

The term "adult" as used herein, is meant to refer to any non-embryonic or non-postnatal juvenile animal or subject. For example the term "adult adipose-derived stromal cell," refers to an adipose-derived stromal cell, other than that obtained from an embryo or juvenile animal.

The term "graft" as used herein refers to the process whereby a free (unattached) cell, tissue, or organ integrates into a tissue following transplantation into a subject.

The term "allograft" refers to a transplanted cell, tissue, or organ derived from a different animal of the same species.

The term "xenograft" or "xenotransplant" as used herein refers to a transplanted cell, tissue, or organ derived from an animal of a different species. In some embodiments, a xenograft is a surgical graft of tissue from one species to an unlike species, genus or family. By way of an example, a graft from a baboon to a human is a xenograft.

The term "xenotransplantation" refers to the process of transplantation of living cells, tissues or organs from one species to another, such as from pigs to humans.

As used herein, the term "donor" refers to a subject to which an organ, tissue or cell to be transplanted is harvested from.

As used herein, the term "recipient" refers to a subject which will receive a transplanted organ, tissue or cell.

The term "host/transplant interface" or "interfacial surface" are used interchangeably herein and refer to the point at which the surface of the transplant tissue or cell transplant contacts the surface of the surrounding host tissue. For example, where a transplant mixed with SVF cells is transplanted, the "host/transplant interface" refers to the point at which the transplant mixed with SVF cells contacts the surface of the surrounding host tissue.

The term "contacting" or "contact" as used herein as in connection with a SVF cell, either present on a support, or absence of a support, contacting a tissue or cell transplant as disclosed herein, includes touching or extremely close proximity of the SVF cell with the tissue or cell transplant.

The terms "engineered tissue", "engineered tissue construct", or "tissue engineered construct" as used herein refer to a tissue or organ that is produced, in whole or in part, using tissue engineering techniques. Descriptions of these techniques can be found in, among other places, "Principles of Tissue Engineering, 2d ed.", Lanza, Langer, and Vacanti, eds., Academic Press, 2000 (hereinafter "Lanza et al."); "Methods of Tissue Engineering", Atala and Lanza, eds., Academic Press, 2001 (hereinafter "Atala et al."); Animal Cell Culture, Masters, ed., Oxford University Press, 2000, (hereinafter "Masters"), particularly Chapter 6; and U.S. Pat. No. 4,963,489 and related U.S. patents. By way of an example only, a "tissue engineered" myocardium refers to the artificial creation of myocardial tissue from cells, such as cardiomyocytes or cardiac progenitors, or from cells such as iPS cells which have been differentiated to become cardiomyocytes. In some embodiments, engineered tissue can comprises three-dimensional matrices and/or an appropriate scaffold such as biopolymer scaffolds as disclosed herein.

As used herein, the term "stem cells" is used in a broad sense and includes traditional stem cells, progenitor cells, preprogenitor cells, reserve cells, and the like. Exemplary stem cells include embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like. Descriptions of stem cells, including method for isolating and culturing them, may be found in, among other places, Embryonic Stem Cells, Methods and Protocols, Turksen, ed., Humana Press, 2002; Weisman et al., Annu. Rev. Cell. Dev. Biol. 17:387 403; Pittinger et al., Science, 284:143 47, 1999; Animal Cell Culture, Masters, ed., Oxford University Press, 2000; Jackson et al., PNAS 96(25):14482 86, 1999; Zuk et al., Tissue Engineering, 7:211 228, 2001 ("Zuk et al."); Atala et al., particularly Chapters 33 41; and U.S. Pat. Nos. 5,559,022, 5,672,346 and 5,827,735. Descriptions of stromal cells, including methods for isolating them, may be found in, among other places, Prockop, Science, 276:7174, 1997; Theise et al., Hepatology, 31:235 40, 2000; Current Protocols in Cell Biology, Bonifacino et al., eds., John Wiley & Sons, 2000 (including updates through March, 2002); and U.S. Pat. No. 4,963,489. The skilled artisan will understand that the stem cells and/or stromal cells selected for inclusion in a transplant with mixed SVF cells or SVF-matrix construct (e.g. for encapsulating a tissue or cell transplant according to the constructs and methods as disclosed herein) are typically appropriate for the intended use of that construct.

As used herein, the terms "iPS cell" and "induced pluripotent stem cell" are used interchangeably and refers to a pluripotent cell artificially derived (e.g., induced by complete or partial reversal) from an undifferentiated cell (e.g. a non-pluripotent cell) or a somatic cell such as a differentiated somatic cell. iPS cells are capable of self-renewal and differentiation into cell fate-committed stem cells, including neural stem cells, as well as various types of mature cells.

The term "derived from" used in the context of a cell derived from another cell means that a cell has stemmed (e.g. changed from or produced by) a cell which is a different cell type. In some instances, for e.g. a cell derived from an iPS cell refers to a cell which has differentiated from an iPS cell. Alternatively, a cell can be converted from one cell type to a different cell type by a process referred to as transdifferention or direct reprogramming Alternatively, in the terms of iPS cells, a cell (e.g. iPS cell) can be derived from a differentiated cell by a process referred to in the art as dedifferentiation or reprogramming.

The term "Relevant Cells", as used herein refers to cells that are appropriate for incorporation into a transplant with mixed SVF cells or SVF-matrix construct (e.g. for encapsulating a tissue or cell transplant according to the constructs and methods as disclosed herein) depends on the tissue or cell transplant to be transplanted. For example, Relevant Cells that are appropriate for the repair, restructuring, or repopulation of damaged liver may include, without limitation, hepatocytes, biliary epithelial cells, Kupffer cells, fibroblasts, and the like. Exemplary Relevant Cells for incorporation into prevascularized constructs include neurons, myocardiocytes, myocytes, chondrocytes, pancreatic acinar cells, islets of Langerhans, osteocytes, hepatocytes, Kupffer cells, fibroblasts, myocytes, myoblasts, satellite cells, endothelial cells, adipocytes, preadipocytes, biliary epithelial cells, and the like. These types of cells may be isolated and cultured by conventional techniques known in the art. Exemplary techniques can be found in, among other places, Atala et al., particularly Chapters 9 32; Freshney, Culture of Animal Cells A Manual of Basic Techniques, 4th ed., Wiley Liss, John Wiley & Sons, 2000; Basic Cell Culture: A Practical Approach, Davis, ed., Oxford University Press, 2002; Animal Cell Culture: A Practical Approach, Masters, ed., 2000; and U.S. Pat. Nos. 5,516,681 and 5,559,022.

The term "isolated" when used in reference to cells, refers to a single cell of interest, or a heterogeneous population of cells of interest such as SVF cells, at least partially isolated from other cell types or other cellular material with which it naturally occurs in the tissue of origin (e.g., adipose tissue). Stated another way, isolated SVFs are substantially free of adipocytes and red blood cells and clonal populations of connective tissue stem cells, and are substantially devoid of cells such as extracellular matrix material and cells from adipose tissue. A sample of SVFs which is "substantially pure" when it is at least 60%, or at least 75%, or at least 90%, and, in certain cases, at least 99% free of cells of adipose tissue other than cells of interest. For clarity, the cells of interest in a heterogeneous population of cells of a SVF cell population include, for example but are not limited to endothelial cells, mesenchymal stem cells, fibroblasts, smooth muscle cells, pericytes and adipose-derived stem cells. Purity can be measured by any appropriate method, for example, by fluorescence-activated cell sorting (FACS), or other assays which distinguish cell types. The term "enriching" is used synonymously with "isolating" cells, and means that the yield (fraction) of cells of one type is increased by at least 10% over the fraction of cells of that type in the starting culture or preparation.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a population of SVF cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not SVF cells as defined by the terms herein.

As used herein, the term "purified", relates to an enrichment of a cell, cell type, molecule, or compound relative to other components normally associated with the cell, cell type, molecule, or compound in a native environment. The term "purified" does not necessarily indicate that complete purity of the particular cell, cell type, molecule, or compound has been achieved during the process. A "highly purified" population of SVF cells as used herein refers to a population of SVF cells that is greater than 90% pure (i.e. the highly purified population of SVF cells comprises at least 90% cells of SVF population (i.e. endothelial cells, mesenchymal stem cells, fibroblasts, smooth muscle cells, pericytes and adipose-derived stem cells) relative to non-SVF cells such as red blood cells, adipocytes and cells of the extracellular matrix of adipose tissue).

The term "isolated cell" as used herein refers to a cell that has been removed from an organism in which it was originally found or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of SVF cells as used herein refers to a population of cells that has been removed and separated from a non-SVF cells in a mixed or heterogeneous population of SVF cells and non-SVF cells. In some embodiments, an isolated population is a substantially pure population of cells as compared to the heterogeneous population from which the cells were isolated or enriched from. In some embodiments, the isolated population is an isolated population of reprogrammed cells which is a substantially pure population of reprogrammed cells as compared to a heterogeneous population of cells comprising reprogramming cells and cells from which the reprogrammed cells were derived.

The terms "subject" and "individual" are used interchangeably herein, and refer to an animal, for example a human, to whom a SVP cells or transplant tissue can be harvested from, or a subject whom tissue can be transplanted into for treatment using the methods and compositions described herein. For treatment of conditions or disease states which are specific for a specific animal such as a human subject, the term "subject" refers to that specific animal. In some embodiments, the subject is a human subject. The terms "non-human animals" and "non-human mammals" are used interchangeably herein, and include mammals such as rats, mice, rabbits, sheep, cats, dogs, cows, pigs, and non-human primates. In some embodiments, the invention encompasses recipient subjects which are a different mammalian subject to the donor subject. As an illustrative example only, a donor subject may be a pig subject, and the recipient subject can be a human subject.

The term "mammal" or "mammalian" are used interchangeably herein, are intended to encompass their normal meaning. While the invention is most desirably intended for efficacy in humans, it may also be employed in domestic mammals such as canines, felines, and equines, as well as in mammals of particular interest, e.g., zoo animals, farmstock, transgenic animals, rodents and the like.

The term "three-dimensional matrix" is used in the broad sense herein and refers to a composition comprising a biocompatible matrix, scaffold, or the like. The three-dimensional matrix may be liquid, gel, semi-solid, or solid at 25° C. The three-dimensional matrix may be biodegradable or non-biodegradable. In some embodiments, the three-dimensional matrix is biocompatible, or bioresorbable or bioreplaceable. Exemplary three-dimensional matrices include polymers and hydrogels comprising collagen, fibrin, chitosan, MATRIGEL™, polyethylene glycol, dextrans including chemically crosslinkable or photocrosslinkable dextrans, processed tissue matrix such as submucosal tissue and the like. In certain embodiments, the three-dimensional matrix comprises allogeneic components, autologous components, or both allogeneic components and autologous components. In certain embodiments, the three-dimensional matrix comprises synthetic or semi-synthetic materials. In certain embodiments, the three-dimensional matrix comprises a framework or support, such as a fibrin-derived scaffold.

The term "biodegradable" as used herein denotes a composition that is not biologically harmful and can be chemically degraded or decomposed by natural effectors (e.g., weather, soil bacteria, plants, animals).

The term "bioresorbable" refers to the ability of a material to be reabsorbed over time in the body (e.g. in vivo) so that its original presence is no longer detected once it has been reabsorbed.

The term "bioreplaceable" as used herein, and when used in the context of an implant, refers to a process where de novo growth of the endogenous tissue replaces the implant material. A bioreplacable material as disclosed herein does not provoke an immune or inflammatory response from the subject and does not induce fibrosis. A bioreplaceable material is distinguished from bioresorbable material in that bioresorbable material is not replaced by de novo growth by endogenous tissue.

The terms "processed tissue matrix" and "processed tissue material" are used interchangeably herein, to refer to native, normally cellular tissue that as been procured from an animal source, for example a mammal, and mechanically cleaned of attendant tissues and chemically cleaned of cells and cellular debris, and rendered substantially free of non-collagenous extracellular matrix components. In some embodiments, the processed tissue matrix can further comprise non-cellular material naturally secreted by cells, such as intestinal submucosa cells, isolated in their native configuration with or without naturally associated cells.

As used herein the term "submucosal tissue" refers to natural extracellular matrices, known to be effective for tissue remodelling, that have been isolated in their native configuration. The submucosal tissue can be from any animal, for example a mammal, such as but not limited to, bovine or porcine submucosal tissue. In some embodiments, the submucosal tissue is derived from a human, such as the subject into which it is subsequently implanted (e.g. autograft transplantation) or from a different human donor (e.g. allograft transplantation). The submucosa tissue can be derived from intestinal tissue (autograft, allograft, and xenograft), stomach tissue (autograft, allograft, and xenograft), bladder tissue (autograft, allograft, and xenograft), alimentary tissue (autograft, allograft, and xenograft), respiratory tissue (autograft, allograft, and xenograft) and genital tissue (autograft, allograft, and xenograft), and derivatives of liver tissue (autograft, allograft, and xenograft), including for example liver basement membrane and also including, but not limited to, dermal extracellular matrices (autograft, allograft, and xenograft) from skin tissue.

The term "scaffold" is also used in a broad sense herein. Thus scaffolds include a wide variety of three-dimensional frameworks, for example, but not limited to a mesh, grid, sponge, foam, or the like.

The term "microvessel fragment" as used herein refers to a segment or piece of vascular tissue, including at least a part or segment of at least one artery, arteriole, capillary, venule, or vein. Typically a microvessel includes endothelial cells arranged in a tube surrounded by one or more layers of mural cells, such as smooth muscle cells or pericytes, and may further comprise extracellular matrix components, such as basement membrane proteins. In certain embodiments, the microvessel fragments are obtained from vascular tissue, for example, but not limited to, skin, skeletal muscle, cardiac muscle, the atrial appendage of the heart, lung, mesentery, or adipose tissue. In certain embodiments, the adipose tissue microvessel fragments are obtained from, for example, but not limited to, subcutaneous fat, perirenal fat, pericardial fat, omental fat, breast fat, epididymal fat, properitoneal fat, and the like. The skilled artisan will appreciate that other fat deposits or any vascular-rich tissue or organ may serve as a source of microvessel fragments for use in the invention, for example, but not limited to, skin, muscle, including skeletal or cardiac muscle, lung, and mesentery. In certain embodiments, the microvessel fragments are obtained from adipose tissue harvested by liposuction or abdominoplasty. Adipiose tissue harvested by a liposuction procedure where a sonic probe is not used during the harvesting process is particularly useful.

The terms "vascularize", "vascularizing", or "vascularization" as used herein refer to providing a functional or substantially functional vascular network to an organ or tissue, particularly an engineered tissue. A functional or substantially functional vascular network is one that perfuses or is capable of perfusing the tissue or organ to meet some or all of the tissue's or organ's nutritional needs, oxygen demand, and waste product elimination needs. A vascular tissue is a natural tissue that is rich in vascular elements, such as microvessels, for example, but without limitation, adipose tissue.

The terms "revascularize", "revascularizing", "neovascularization", or "revascularization" as used herein refer to revising an existing vascular network or establishing a new functional or substantially functional vascular network in a tissue or organ that has an avascular or hypovascular zone, typically due to disease, congenital defect, or injury. Additionally, the topical application of certain chemotherapeutic agents, for example, but not limited to, 5-fluorouracil (5-FU), may also result in an ischemic or avascular zone. Such an avascular or hypovascular tissue or organ is often totally or partially dysfunctional or has limited function and may be in need of revascularization. Revascularizing such a tissue or organ may result in restored or augmented function.

The terms "enhance vascularization" as used herein refers to an increase or acceleration in the rate of formation of a vascularized network. In some embodiments, an enhanced vascularization refers to the formation of a more dense capillary or vascularized network as compared to in the absence of the method (e.g. the vascularization which would occur in the absence of population of SVF cells). Stated another way, an enhancement in vascularization refers to a statistically significant increase in the rate of formation of a vascularized network, or alternatively a statistically significant increase in the amount of capillary which form the vascularized network.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

The term "substantially" as used herein means a proportion of at least about 60%, or preferably at least about 70% or at least about 80%, or at least about 90%, at least about 95%, at least about 97% or at least about 99% or more, or any interger between 70% and 100%.

As used herein, the term "polymer" is used in the broad sense and is intended to include a wide range of biocompatible polymers, for example, but not limited to, homopolymers, co-polymers, block polymers, cross-linkable or crosslinked polymers, photoinitiated polymers, chemically initiated polymers, biodegradable polymers, nonbiodegradable polymers, and the like. In other embodiments, the prevascularized construct comprises a polymer matrix that is nonpolymerized, to allow it to be combined with a tissue, organ, or engineered tissue in a liquid or semi-liquid state, for example, by injection. In certain embodiments, the prevascularized construct comprising liquid matrix may polymerize or substantially polymerize "in situ." In certain embodiments, the prevascularized construct is polymerized or substantially polymerized prior to injection. Such injectable compositions are prepared using conventional materials and methods know in the art, including, but not limited to, Knapp et al., Plastic and Reconstr. Surg. 60:389 405, 1977; Fagien, Plastic and Reconstr. Surg. 105:362 73 and 2526 28, 2000; Klein et al., J. Dermatol. Surg. Oncol. 10:519 22, 1984; Klein, J. Amer. Acad. Dermatol. 9:224 28, 1983; Watson et al., Cutis 31:543 46, 1983; Klein, Dermatol. Clin. 19:491 508, 2001; Klein, Pedriat. Dent. 21:449 50, 1999; Skorman, J. Foot Surg. 26:5115, 1987; Burgess, Facial Plast. Surg. 8:176 82, 1992; Laude et al., J. Biomech. Eng. 122:231 35, 2000; Frey et al., J. Urol. 154:812 15, 1995; Rosenblatt et al., Biomaterials 15:985 95, 1994; Griffey et al., J. Biomed. Mater. Res. 58:10 15, 2001; Stenburg et al., Scfand. J. Urol. Nephroi. 33:355 61,1999; Sclafani et al., Facial Plast. Surg. 16:29 34, 2000; Spira et al., Clin. Plast. Surg. 20:18188, 1993; Ellis et al., Facila Plast. Surg. Clin. North Amer. 9:405 11, 2001; Alster et al., Plastic Reconstr. Surg. 105:2515 28, 2000; and U.S. Pat. Nos. 3,949,073 and 5,709,854.

In certain embodiments, the polymerized or nonpolymerized matrix comprises collagen, including contracted and non-contracted collagen gels, hydrogels comprising, for example, but not limited to, fibrin, alginate, agarose, gelatin, hyaluronate, polyethylene glycol (PEG), dextrans, including dextrans that are suitable for chemical crosslinking, photocrosslinking, or both, albumin, polyacrylamide, polyglycolyic acid, polyvinyl chloride, polyvinyl alcohol, poly(n-vinyl-2-pyrollidone), poly(2-hydroxy ethyl methacrylate), hydrophilic polyurethanes, acrylic derivatives, pluronics, such as polypropylene oxide and polyethylene oxide copolymer, or the like. In certain embodiments, the fibrin or collagen is autologous or allogeneic with respect to the intended recipient. The skilled artisan will appreciate that the matrix may comprise non-degradable materials, for example, but not limited to, expanded polytetrafluoroethylene (ePTFE), polytetrafluoroethylene (PTFE), polyethyleneterephthalate (PET), polyurethane, polyethylene, polycabonate, polystyrene, silicone, and the like, or selectively degradable materials, such as poly (lactic-co-glycolic acid; PLGA), PLA, or PGA. (See also, Middleton et al., Biomaterials 21:2335 2346, 2000; Middleton et al., Medical Plastics and Biomaterials, March/April 1998, at pages 30 37; Handbook of Biodegradable Polymers, Domb, Kost, and Domb, eds., 1997, Harwood Academic Publishers, Australia; Rogalla, Minim. Invasive Surg. Nurs. 11:67 69, 1997; Klein, Facial Plast. Surg. Clin. North Amer. 9:205 18, 2001; Klein et al., J. Dermatol. Surg. Oncol. 11:337 39, 1985; Frey et al., J. Urol. 154:812 15, 1995; Peters et al., J. Biomed. Mater. Res. 43:422 27, 1998; and Kuijpers et al., J. Biomed. Mater. Res. 51:136 45, 2000).

The term "gene" as used herein refers to the nucleotide sequences which encode the amino acids found in the nascent polypeptide as a result of translation of a mRNA molecule. The coding region is bounded, in eukaryotes, on the 5'-side by the nucleotide triplet "ATG" which encodes the initiator methionine and on the 3'-side by one of the three triplets which specify stop codons (i.e., TAA, TAG, TGA). In addition to containing introns, genomic forms of a gene may also include sequences located on both the 5'- and 3'-end of the sequences which are present on the RNA transcript, which are termed "5' untranslated regions" or 5'UTR and 3' untranslated regions (3'UTR) respectively. These sequences are also referred to as "flanking" sequences or regions (these flanking sequences are located 5' or 3' to the non-translated sequences present on the mRNA transcript). The 5'-flanking region may contain regulatory sequences such as promoters and enhancers which control or influence the transcription of the gene. The 3'-flanking region may contain sequences which direct the termination of transcription, post-transcriptional cleavage and polyadenylation. Expression of a gene, for example of a genetically engineered cell (e.g. a genetically engineered SVF cell) can be achieved by introducing a gene which is operably joined to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (downstream) the coding region (open reading frame, ORF) as well as, where applicable, intervening sequences (i.e., 3'UTR, 5"UTR, introns) between individual coding regions (i.e., exons). The term "structural gene" as used herein is intended to mean a DNA sequence that is transcribed into mRNA which is then translated into a sequence of amino acids characteristic of a specific polypeptide.

The term "gene product(s)" as used herein refers to include RNA transcribed from a gene, or a polypeptide encoded by a gene or translated from RNA.

The terms "genome" or "genomic DNA" as used herein refers to the heritable genetic information of a host organism. Genomic DNA comprises the DNA of the nucleus (also referred to as chromosomal DNA) but also the DNA of the plastids (e.g., chloroplasts) and other cellular organelles (e.g., mitochondria). The terms genome or genomic DNA typically refers to the chromosomal DNA of the nucleus.

The term "exon" as used herein refers to the normal sense of the term as meaning a segment of nucleic acid molecules, usually DNA, that encodes part of or all of an expressed protein.

The term "expression" as used herein refers to the biosynthesis of a gene product, preferably to the transcription and/or translation of a nucleotide sequence, for example an endogenous gene or a heterologous gene, in a cell. For example, in the case of a heterologous nucleic acid sequence, expression involves transcription of the heterologous nucleic acid sequence into mRNA and, optionally, the subsequent translation of mRNA into one or more polypeptides. Expression also refers to biosynthesis of a RNAi molecule, which refers to expression and transcription of an RNAi agent such as siRNA, shRNA, and antisense DNA but does not require translation to polypeptide sequences.

The term "expression construct" and "nucleic acid construct" as used herein are synonyms and refer to a nucleic acid sequence capable of directing the expression of a particular nucleotide sequence, such as the heterologous target gene sequence in an appropriate host cell (e.g., a mammalian cell). If translation of the desired heterologous target gene is required, it also typically comprises sequences required for proper translation of the nucleotide sequence. The coding region may code for a protein of interest but may also code for a functional RNA of interest, for example antisense RNA, dsRNA, or a nontranslated RNA, in the sense or antisense direction. The nucleic acid construct as disclosed herein can be chimeric, meaning that at least one of its components is heterologous with respect to at least one of its other components.

The term "agent" refers to any entity which is normally absent or not present at the levels being administered, in the cell. Agent may be selected from a group comprising; chemicals; small molecules; nucleic acid sequences; nucleic acid analogues; proteins; peptides; aptamers; antibodies; or fragments thereof. A nucleic acid sequence may be RNA or DNA, and may be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. The agent may be applied to the media, where it contacts the cell and induces its effects. Alternatively, the agent may be intracellular within the cell as a result of introduction of the nucleic acid sequence into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

As used herein, "a reduction" of the level of a gene, included a decrease in the level of a protein or mRNA means in the cell or organism. As used herein, "at least a partial reduction" of the level of an agent (such as a RNA, mRNA, rRNA, tRNA expressed by the target gene and/or of the protein product encoded by it) means that the level is reduced at least 25%, preferably at least 50%, relative to a cell or organism lacking the RNAi agent as disclosed herein. As used herein, "a substantial reduction" of the level of an agent such as a protein or mRNA means that the level is reduced relative to a cell or organism lacking a chimeric RNA molecule of the invention capable of reducing the agent, where the reduction of the level of the agent is at least 75%, preferably at least 85%. The reduction can be determined by methods with which the skilled worker is familiar. Thus, the reduction of the transgene protein can be determined for example by an immunological detection of the protein. Moreover, biochemical techniques such as Northern hybridization, nuclease protection assay, reverse transcription (quantitative RT-PCR), ELISA (enzyme-linked immunosorbent assay), Western blotting, radioimmunoassay (RIA) or other immunoassays and fluorescence-activated cell analysis (FACS) to detect transgene protein or mRNA. Depending on the type of the reduced transgene, its activity or the effect on the phenotype of the organism or the cell may also be determined. Methods for determining the protein quantity are known to the skilled worker. Examples, which may be mentioned, are: the micro-Biuret method (Goa J (1953) Scand J Clin Lab Invest 5:218-222), the Folin-Ciocalteau method (Lowry O H et al. (1951) J Biol Chem 193:265-275) or measuring the absorption of CBB G-250 (Bradford MM (1976) Analyt Biochem 72:248-254).

As used herein, the term "amino acid sequence" refers to a list of abbreviations, letters, characters or words representing amino acid residues Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "nucleic acids" and "Nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or double stranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used interchangeably herein with "gene", "cDNA, "mRNA", "oligonucleotide," and "polynucleotide". Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. shRNAs also can comprise non-natural elements such as non-natural bases, e.g., ionosin and xanthine, nonnatural sugars, e.g., 2'-methoxy ribose, or non-natural phosphodiester linkages, e.g., methylphosphonates, phosphorothioates and peptides. The term "nucleic acid" or "oligonucleotide" or "polynucleotide" are used interchangeably herein and refers to at least two nucleotides covalently linked together. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid can be used for the same purpose as a given nucleic acid. Thus, a nucleic acid also encompasses substantially identical nucleic acids and complements thereof. As will also be appreciated by those in the art, a single strand provides a probe for a probe that can hybridize to the target sequence under stringent hybridization conditions. Thus, a nucleic acid also encompasses a probe that hybridizes under stringent hybridization conditions.

The term "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

A nucleic acid will generally contain phosphodiester bonds, although nucleic acid analogs can be included that can have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog can be located for example at the 5'-end and/or the 3'-end of the nucleic acid molecule. Representative examples of nucleotide analogs can be selected from sugar- or backbone-modified ribonucleotides. It should be noted, however, that also nucleobase-modified ribonucleotides, i.e. ribonucleotides, containing a non naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7 deaza-adenosine; O- and N-alkylated nucleotides, e.g. N6-methyl adenosine are suitable. The 2' OH-group can be replaced by a group selected from H. OR, R. halo, SH, SR, $NH_2$, NHR, $NR_2$ or CN, wherein R is C—C6 alkyl, alkenyl or alkynyl and halo is F, Cl, Br or I. Modifications of the ribose-phosphate backbone can be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs can be made.

The term "operable linkage" or "operably linked" are used interchangeably herein, are to be understood as meaning, for example, the sequential arrangement of a regulatory element (e.g. a promoter) with a nucleic acid sequence to be expressed and, if appropriate, further regulatory elements (such as e.g., a terminator) in such a way that each of the regulatory elements can fulfill its intended function to allow, modify, facilitate or otherwise influence expression of the linked nucleic acid sequence. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. In some embodiments, arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly can be any distance, and in some embodiments is less than 200 base pairs, especially less than 100 base pairs, less than 50 base pairs. In some embodiments, the nucleic acid sequence to be transcribed is located behind the promoter in such a way that the transcription start is identical with the desired beginning of the chimeric RNA of the invention. Operable linkage, and an expression construct, can be generated by means of customary recombination and cloning techniques as described (e.g., in Maniatis T, Fritsch EF and Sambrook J (1989) Molecular Cloning: A Laboratory Manual, 2nd Ed., Cold Spring Harbor Laboratory, Cold Spring Harbor (NY); Silhavy et al. (1984) Experiments with Gene Fusions, Cold Spring Harbor Laboratory, Cold Spring Harbor (NY); Ausubel et al. (1987) Current Protocols in Molecular Biology, Greene Publishing Assoc and Wiley Interscience; Gelvin et al. (Eds) (1990) Plant Molecular Biology Manual; Kluwer Academic Publisher, Dordrecht, The Netherlands). However, further sequences, which, for example, act as a linker with specific cleavage sites for restriction enzymes, or as a signal peptide, may also be positioned between the two sequences. The insertion of sequences may also lead to the expression of fusion proteins. In some embodiments, the expression construct, consisting of a linkage of promoter and nucleic acid sequence to be expressed, can exist in a vector integrated form and be inserted into a plant genome, for example by transformation.

The term "nucleic acid construct" as used herein refers to a nucleic acid at least partly created by recombinant methods. The term "DNA construct" is referring to a polynucleotide construct consisting of deoxyribonucleotides. The construct can be single or double stranded. The construct can be circular or linear. A person of ordinary skill in the art is familiar with a variety of ways to obtain one of a DNA construct. Constructs can be prepared by means of customary recombination and cloning techniques as are described, for example, in Maniatis T, Fritsch EF and Sambrook J (1989) Molecular Cloning: A Laboratory Manual, 2nd Ed., Cold Spring Harbor Laboratory, Cold Spring Harbor (NY); Silhavy et al. (1984) Experiments with Gene Fusions, Cold Spring Harbor Laboratory, Cold Spring Harbor (NY); Ausubel et al. (1987) Current Protocols in Molecular Biology, Greene Publishing Assoc and Wiley Interscience; Gelvin et al. (Eds) (1990) Plant Molecular Biology Manual; Kluwer Academic Pub-lisher, Dordrecht, The Netherlands.

The terms "polypeptide", "peptide", "oligopeptide", "polypeptide", "gene product", "expression product" and "protein" are used interchangeably herein to refer to a polymer or oligomer of consecutive amino acid residues.

The terms "promoter," "promoter element," or "promoter sequence" are equivalents and as used herein, refers to a DNA sequence which when operatively linked to a nucleotide sequence of interest is capable of controlling the transcription of the nucleotide sequence of interest into mRNA. A promoter is typically, though not necessarily, located 5' (i.e., upstream) of a nucleotide sequence of interest (e.g., proximal to the transcriptional start site of a structural gene) whose transcription into mRNA it controls, and provides a site for specific binding by RNA polymerase and other transcription factors for initiation of transcription. A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur (e.g., tissue promoters). If a promoter is an inducible promoter, then the rate of transcription in creases in response to an inducing agent. In contrast, the rate of transcription is not regulated by an inducing agent if the promoter is a constitutive promoter. Also, the promoter may be regulated in a tissue-specific or tissue preferred manner such that it is only active in transcribing the associated coding region in a specific tissue type(s) such as in a cancer cell.

The term "tissue specific" as it applies to a promoter refers to a promoter that is capable of directing selective expression of a nucleotide sequence of interest to a specific type of tissue (e.g., liver) in the relative absence of expression of the same nucleotide sequence of interest in a different type of tissue (e.g., kidney). Tissue specificity of a promoter may be evaluated by, for example, operably linking a reporter gene to the promoter sequence to generate a reporter construct, introducing the reporter construct into the genome of an organism, e.g. an animal model such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the promoter is specific for the tissues in which greater levels of expression are detected.

The term "transgene" as used herein refers to any nucleic acid sequence, which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence, which is naturally found in the cell into which it is introduced so long as it does not contain some modification (e.g., a point mutation, the presence of a selectable marker gene, etc.) relative to the naturally-occurring sequence. The term transgenic when referring to a cell, tissue or organisms means transformed, preferably stably transformed, with a recombinant DNA molecule that preferably comprises a suitable promoter operatively linked to a DNA sequence of interest.

The term "vectors" is used interchangeably with "plasmid" to refer to a nucleic acid molecule capable of transporting another nucleic acid to which it has been linked. Vectors capable of directing the expression of genes and/or nucleic acid sequence to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. Other expression vectors can be used in different embodiments of the invention, for example, but are not limited to, plasmids, episomes, bacteriophages or viral vectors, and such vectors can integrate into the host's genome or replicate autonomously in the particular cell. Other forms of expression vectors known by those skilled in the art which serve the equivalent functions can also be used. Expression vectors comprise expression vectors for stable or transient expression encoding the DNA. A vector can be a plasmid, bacteriophage, bacterial artificial chromosome or yeast artificial chromosome. A vector can be a DNA or RNA vector. A vector can be either a self replicating extrachromosomal vector or a vector which integrate into a host genome.

The term "disease" or "disorder" is used interchangeably herein, and refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, indisposition or affection.

The term "pathology" as used herein, refers to symptoms, for example, structural and functional changes in a cell, tissue or organs, which contribute to a disease or disorder. For example, the pathology may be associated with a particular nucleic acid sequence, or "pathological nucleic acid" which refers to a nucleic acid sequence that contributes, wholly or in part to the pathology, as an example, the pathological nucleic acid may be a nucleic acid sequence encoding a gene with a particular pathology causing or pathology-associated mutation or polymorphism. The pathology may be associated with the expression of a pathological protein or pathological polypeptide that contributes, wholly or in part to the pathology associated with a particular disease or disorder. In another embodiment, the pathology is for example, is associated with other factors, for example ischemia and the like.

As used herein, the terms "treat" or "treatment" or "treating" refers to therapeutic treatment wherein the object is to prevent or slow the development of the disease. Treatment is generally "effective" if one or more symptoms or clinical markers are reduced as that term is defined herein. Alternatively, a treatment is "effective" if the progression of a disease is reduced or halted. That is, "treatment" includes not just an improvement of a symptom or a decrease in a marker of a disease, but also a cessation or slowing of the progress or worsening of a symptom that would be expected in absence of treatment. Beneficial or desired clinical results include, but are not limited to, alleviation of one or more symptom(s), diminishment of extent of disease, stabilized (e.g., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with a need for a transplant, e.g., a heart-and-lung transplant, such as subjects with a serious cardiovascular condition. In some embodiments, treatment also includes prophylactic or preventative treatment to prevent developing a symptom of a disease or disorder, for example, where a subject is likely to develop a disease due to genetic susceptibility or other factors such as weight, diet and health. For example, prophylactic treatment may be sought by a subject which a very high risk of breast cancer due to genetic defects in the BRAC1 and/or BRAC2 gene, and where the subject opts for a preventative mastectomy and the methods and compositions can be used for encapsulating a breast tissue transplant in reconstructive breast surgery. In an alternative example, the methods and compositions can be used for treatment of an existing condition, e.g., a transplant of a cell transplant which functions as a bioreactor, e.g., where the bioreactor secretes a therapeutic composition, such as a peptide or growth factor to surrounding cells.

The term "effective amount" as used herein refers to the amount of therapeutic agent of pharmaceutical composition (e.g. e.g. a transplant mixed with SVF cells, or transplant encapsulated with SVF cells) to reduce at least one or more symptom(s) of the disease or disorder, and relates to a sufficient amount of pharmacological composition to provide the desired effect. The phrase "therapeutically effective amount" as used herein, (e.g., amount of a transplant mixed with SVF cells, or transplant encapsulated with SVF cells) means a sufficient amount of the composition to treat a disorder, at a reasonable benefit/risk ratio applicable to any medical treatment. The term "therapeutically effective amount" therefore refers to an amount of the composition as disclosed herein (e.g. transplant mixed with SVF cells, or transplant encapsulated with SVF cells) that is sufficient to effect a therapeutically significant reduction in a symptom or clinical marker associated with a dysfunction or disorder when administered to a typical subject who has a condition, disease or disorder to be treated.

A therapeutically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject. Measured or measurable parameters include clinically detectable markers of disease, for example, elevated or depressed levels of a biological marker, as well as parameters related to a clinically accepted scale of symptoms or markers for a disease or disorder. It will be understood, that the total daily usage of the compositions and formulations as disclosed herein will be decided by the attending physician within the scope of sound medical judgment. The exact amount required will vary depending on factors such as the type of disease being treated.

As used herein, the terms "administering," "introducing" and "transplanting" are used interchangeably and refer to the placement of the e.g. transplant mixed with SVF cells or transplant encapsulated with SVF cells as described herein into a subject by a method or route which results in at least partial localization of the transplant tissue at a desired site. The transplant mixed with SVF cells, or transplant encapsulated with SVF cells can be administered by any appropriate route which results in effective treatment in the subject, e.g. administration results in delivery to a desired location in the subject where at least a portion of the transplant mixed with SVF cells, or transplant encapsulated with SVF cells of the cells remain viable. The period of viability of the cells after administration to a subject can be as short as a few hours, e.g. twenty-four hours, to a few days, to as long as several years.

The phrases "parenteral administration" and "administered parenterally" as used herein mean modes of administration of a transplant mixed with SVF cells, or transplant encapsulated with SVF cells other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically", "peripheral administration" and "administered peripherally" as used herein mean the administration of the compositions as disclosed herein, e.g. transplant mixed with SVF cells, or transplant encapsulated with SVF cells to the subject such that it enters the animal's system and, thus, is subject to metabolism and other like processes.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation. The pharmaceutical formulation contains a compound of the invention in combination with one or more pharmaceutically acceptable ingredients. The carrier can be in the form of a solid, semi-solid or liquid diluent, cream or a capsule. These pharmaceutical preparations are a further object of the invention. Usually the amount of active compounds is between 0.1-95% by weight of the preparation, preferably between 0.2-20% by weight in preparations for parenteral use and preferably between 1 and 50% by weight in preparations for oral administration. For the clinical use of the methods of the present invention, targeted delivery composition of the invention is formulated into pharmaceutical compositions or pharmaceutical formulations for parenteral administration, e.g., intravenous; mucosal, e.g., intranasal; enteral, e.g., oral; topical, e.g., transdermal; ocular, e.g., via corneal scarification or other mode of administration. The pharmaceutical composition contains a compound of the invention in combination with one or more pharmaceutically acceptable ingredients. The carrier can be in the form of a solid, semi-solid or liquid diluent, cream or a capsule.

The terms "composition" or "pharmaceutical composition" used interchangeably herein refer to compositions or formulations that usually comprise an excipient, such as a pharmaceutically acceptable carrier that is conventional in the art and that is suitable for administration to mammals, and preferably humans or human cells. Such compositions can be specifically formulated for administration via one or more of a number of routes, including but not limited to, oral, ocular parenteral, intravenous, intraarterial, subcutaneous, intranasal, sublingual, intraspinal, intracerebroventricular, and the like. In addition, compositions for topical (e.g., oral mucosa, respiratory mucosa) and/or oral administration can form solutions, suspensions, tablets, pills, capsules, sustained-release formulations, oral rinses, or powders, as known in the art are described herein. The compositions also can include stabilizers and preservatives. For examples of carriers, stabilizers and adjuvants, University of the Sciences in Philadelphia (2005) *Remington: The Science and Practice of Pharmacy with Facts and Comparisons,* 21st Ed.

As used herein, the word "or" means any one member of a particular list and also includes any combination of members of that list. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof.

In this specification and the appended claims, the singular forms "a," "an," and "the" include plural references unless the context clearly dictates otherwise, and therefore "a" and "an" are used herein to refer to one or to more than one (i.e., at least one) of the grammatical object of the article. By way of example, "an element" means one element or more than one element, and reference to a composition for delivering "an agent" includes reference to one or more agents.

Compositions or methods "comprising" one or more recited elements may include other elements not specifically recited. For example, a composition that comprises SVF cells encompasses both the isolated SVF cells but may also include other cell types or protein or other components. By way of further example, a composition that comprises elements A and B also encompasses a composition consisting of A, B and C. The terms "comprising" means "including principally, but not necessary solely". Furthermore, variation of the word "comprising", such as "comprise" and "comprises", have correspondingly varied meanings. The term "consisting essentially" means "including principally, but not necessary solely at least one", and as such, is intended to mean a "selection of one or more, and in any combination."

Other than in the operating examples, or where otherwise indicated, all numbers expressing quantities of ingredients or reaction conditions used herein should be understood as modified in all instances by the term "about." The term "about" is used herein to mean approximately, roughly, around, or in the region of When the term "about" is used in conjunction with a numerical range, it modifies that range by extending the boundaries above and below the numerical values set forth. The term "about" when used in connection with percentages will mean ±1%.

I. Methods and Compositions Using SVFs to be Mixed with Tissues or Cell Transplants Prior to Transplantation One aspect of the present invention provides methods and compositions comprising a population of SVF cells in combination with (e.g. mixed in) tissue cells or cell transplants which are to be transplanted into a subject. In such embodiments, a combination of SVF cells and tissue cells or cell transplant cells form a composition which is referred to herein as a "transplant mixed with SVF cells". In such embodiments, a transplant mixed with SVF cells can be on the surface of, or embedded within a three-dimensional matrix, such as a gel or other matrices as disclosed herein. In some embodiments, the transplant mixed with SVF cells, (e.g. a heterologous mixture of a population of SVF cells and a population of cells of interest to be transplanted) can include additional populations of cells. In some embodiments where the transplant mixed with SVF cells includes additional populations of cells, the additional cells do not include microvessel fragments. Alternatively, in some embodiments, where a three dimensional matrix is not used, a transplant mixed with SVF cells can also include microvessel fragments.

In some embodiments, a transplant mixed with SVF cells is administered to a subject by injection, independent of whether the transplant mixed with SVF cells is present on the surface of, or embedded within a three-dimensional matrix. In some embodiments, a transplant mixed with SVF cells is administered to a subject by surgical procedures commonly known by a skilled artisan.

In some embodiments, a transplant cells are mixed, for example, as a heterogeneous population with SVF cells prior to implantation. In some embodiments, the transplant mixed with SVF cells is present on the surface of, or embedded within a three-dimensional biocompatible matrix. In some embodiments, a transplant mixed with SVF cells further comprises additional cells. In certain embodiments, the transplant mixed with SVF cells construct further comprises appropriate stromal cells, stem cells, Relevant Cells, or combinations thereof. In particular embodiments, a transplant mixed with SVF cells does not comprise microvessel fragments. In some embodiments, where a three-dimensional biocompatible matrix is not present, the transplant mixed with SVF cells can comprise a population of SVF cells, a population of cells of interest to be transplanted and microvessel fragments.

The skilled artisan will appreciate that such formation of a transplant mixed with SVF cells, by addition of the transplant cells and optionally addition of additional cells (e.g. stem cells, and/or Relevant Cells) may be incorporated into a transplant with mixed SVF cells during or after preparation. For example, but not limited to, combining SVF cells, and transplant cells (and optionally additional cells e.g. stem cells, Relevant Cells), in a liquid three-dimensional culture, such as collagen, fibrin, or the like, or seeding or sodding the SVF cells and transplant cells. Exemplary combinations of transplant cells to be combined with SVF cells include: islets of Langerhans and/or pancreatic acinar cells in a prevascularized construct for revascularizing a damaged pancreas; hepatocytes, hepatic progenitor cells, Kupffer cells, endothelial cells, endodermal stem cells, liver fibroblasts, and/or liver reserve cells in a transplant mixed with SVF cells for revascularizing a damaged liver For example, but not limited to, appropriate transplant cells for a transplant mixed with SVF cells for vascularizing, repairing, and reconstructing a damaged or disease liver might comprise liver reserve cells, liver progenitor cells, such as, but not limited to, liver fibroblasts, embryonic stem cells, liver stem cells; cardiomyocytes, Purkinje cells, pacemaker cells, myoblasts, mesenchymal stem cells, satellite cells, and/or bone marrow stem cells for revascularizing a damaged or ischemic heart (see, e.g., Atkins et al., J. of Heart and Lung Transplantation, December 1999, at pages 1173 80; Tomita et al., Cardiovascular Research Institute, American Heart Association, 1999, at pages 92 101; Sakai et al., Cardiovascular Research Institute, American Heart Association, 1999, at pages 108 14); and the like II. Methods and Compositions Using SVFs as an Encapsulating Layer for Tissue or Cells to be Transplanted Another aspect of the present invention relates to the use of a population of SVF cells to promote vascularization of a tissue or cell transplant to be transplanted into a subject. In embodiments of this aspect of the invention, a population of SVF cells can encapsulate (e.g. surround or cover the surface of) a tissue or cell transplant. In some embodiments, the tissue or cell transplant is a tissue engineered tissue, or the like. In some embodiments, the tissue or cell transplant can be on the surface of, or embedded within a three-dimensional matrix as that term is defined herein. In some embodiments, where the tissue or cell transplant is present on the surface of, embedded within a three-dimensional matrix, and is encapsulated with a population of SVF cells, the three-dimensional matrix can further comprise microvessel fragments.

In some embodiments, a population of SVF cells which encapsulates the tissue or cell population is a single or multiple cell layer of SVF cells, which can partially or substantially encapsulate (e.g. surround or cover the surface of) the tissue or cell transplant.

In an alternative embodiment, a population of SVF cells is present on the surface of, or embedded within a three-dimensional matrix to form what is referred to herein as a "SVF-matrix construct", where the SVF-matrix construct partially or substantially encapsulates (e.g. surrounds or covers the surface of) the tissue or cell transplant. In some embodiments, the SVF-matrix can also comprise additional cell types, for example, microvessel fragments. In some embodiments, such a SVF-matrix is combined with the tissue or cell population to be transplanted by placing and affixing the SVF-matrix to the surface of the tissue or cell population to be transplanted.

In certain embodiments, the SVF-matrix construct further comprises appropriate stromal cells, stem cells, Relevant Cells, or combinations thereof, as disclosed in more detail herein.

In one embodiment, a transplant encapsulated with SVF cells can be an engineered tissue encapsulated with SVF cells for example, but not limited to engineered pancreatic tissue prepared in a bioreactor, for example, but without limitation, according to U.S. Pat. No. 6,022,743. Any engineered tissue can be used for a transplant mixed with SVF cells or a transplant encapsulated with SVF cells. For example, in one embodiment, an engineered pancreatic tissue is removed from the bioreactor and coated with a population of SVF cells or SVF-matrix, where a SVF matrix is wrapped around the engineered pancreatic tissue and attaching it with 8-0 sutures. The combination of the engineered pancreatic tissue encapsulated (e.g. surrounded with or covered) with SVF-cells (either as a single layer of SVF cells, or a SVF-matrix) can be implanted in a subject, e.g. a human subject, following surgical following procedures. Thus, in some embodiments, the methods provide a vascularized pancreatic tissue which is generated in vivo by encapsulating with SVF cells.

III. Tissue or Cell Populations of Interest to be Transplanted

In some embodiments, the tissue for producing a transplant mixed with SVF cells or a transplant encapsulated with SVF is an engineered tissue, which is also referred to herein as "tissue engineered tissue". Methods for preparing engineered tissues are well known in the art. Descriptions of such techniques may be found in, among other places, Atala et al.; Lanza et al.; Masters; and in U.S. Pat. Nos. 4,963,489; 5,266,480; 5,510,254; 5,512,475; 5,516,680; 5,516,681; 5,518,915; 5,541,107; 5,578,485; 5,624,840; 5,763,267; 5,785,964; 5,792,603; 5,842,477; 5,858,721; 5,863,531; 5,902,741; 5,962,325; 6,022,743; 6,060,306; 6,121,042; and 6,218,182, which are each incorporated herein in their entirety by reference. Any engineered tissue can be used for a transplant mixed with SVF cells or a transplant encapsulated with SVF cells. Accordingly, one aspect of the present invention relates to methods of use of SVFs to mix with and/or encapsulate engineered tissues and enhance vascularization of the engineered tissues.

In some embodiments, the SVFs can be used to encapsulate and/or mixed among xenograft tissue, cells. Accordingly, one aspect of the present invention provides the use of SVFs in xenograft transplantation procedures, such as disclosed in Zhu et al, Pig-to-Non-human Primate Heart Transplantation: Immunologic Progress Over 20 Years, J. Heart and Lung Transplant. 26; 2007, 210-218.

In some embodiments, the methods and compositions as disclosed herein are amenable to transplantation of any tissues or cell population in which it is desirable to be transplanted into a subject. Examples of tissues which can be transplanted into a subject include for example, without limitation, bone, Fat, Islets, skin, Parathyroid, Liver, Spleen, Cardiac Muscle, Skeletal Muscle, Blood Vessels, Cornea, Trabecular Meshwork, Lung tissue, Lymph tissue, Tissue Engineered Tissue, Regenerative Cells, and tissue generated from stem cells.

Examples of cell populations which can be transplanted into a subject include for example, without limitation, bone cells, Fat cells, Islet cells, islet β-cells, parathyroid cells, liver cells, spleen cells, hepatic cells, cardiomyocytes, myocytes, vascular cells, epithelial cells, blood vessel cells, cornea cells, trabecular cells, meshwork cells, lung cells, Lymph cells, hematapoeic cells, blood cells, regenerative Cells, and stem cells, such as iPS cells. In some embodiments, the cells which are transplanted into a subject are genetically engineered cells.

In some embodiments, where the cells of interest to be transplanted are cells, e.g. somatic cells which have been differentiated from iPS cells. In some embodiments, cell transplants are cells differentiated from stem cells, including adult stem cells, embryonic stem cells, embryonic stem cell lines and the like. Alternatively, one can use cells for cell transplants derived from any number of cells sources known to a person of ordinary skill in the art, such as for example, but not limited to, stem cells, such as cardiac progenitor cells, or embryonic sources, embryonic stem (ES) cells, adult stem cells (ASC), embryoid bodies (EB) and induced pluripotent stem cells (iPS cells).

In some embodiments, an iPS cell produced by any method known in the art can be used, for example virally-induced or chemically induced generation of iPS cells as disclose in EP1970446, US2009/0047263, US2009/0068742, and 2009/0227032, which are incorporated herein in their entirety by reference. Non-viral methods to generate iPS cells are also known in the art, such as RNA mediated methods and are encompassed for use in the methods and compositions as disclosed herein, and are disclosed in "Highly efficient Reprogramming to pluripotency and Directed Differentiation of Human cells with synthetic modified mRNA" Warren et al., Cell Stem cell, 2010, 7; 1-13, which is incorporated herein in its entirety by reference.

In some embodiments, the cell transplants comprise cells which are derived from the reprogramming of cells. For example, a population of transplant cells for use in the methods and to be used on transplant-mixed SVF cells or transplants encapsulated with SVF cells as disclosed herein can be from an induced pluripotent stem cell (iPS), by method known by a person of ordinary skill in the art. For example, methods to produce skin derived iPS cell derived-cardiomyocytes have been described in Mauritz et al., *Circulation.* 2008; 118:507-517, and disclosed in International Application WO2008/088882 and patent applications EP1970446, US2009/0047263, US2009/0068742, and 2009/0227032 which are incorporated herein in their entirety by reference. In some embodiments, a somatic cell can be reprogrammed into a iPS cell by any method known in the art can be used, for example, an iPS cell can also be generated using other methods commonly known in the art, such as, including but not limited to uses of non-viral methods, polycistronic vectors, mRNA species, miRNA, and proteins, including International Patent Applications WO2010/019569, WO2009/149233, WO2009/093022, WO2010/022194, WO2009/101084, WO2008/038148, WO2010/059806, WO2010/057614, WO2010/056831, WO2010/050626, WO2010/033906, WO2009/126250, WO2009/143421, WO2009/140655, WO2009/133971, WO2009/101407, WO2009/091659, WO2009/086425, WO2009/079007, WO2009/058413, WO2009/032456, WO2009/032194, WO2008/103462, JP4411362, EP2128245, and U.S. Patent Applications US2004/0072343, US2009/0253203, US2010/0112693, US2010/07542, US2009/0246875, US2009/0203141, US2010/00625343, US2009/0269763, US2010/059806 which are incorporated herein in their entirety by reference.

In some embodiments, the cells for transplant are derived from cardiac progenitor cells, such as for example but not limited to cells derived from Isl1+ multipotent progenitor cells as disclosed in U.S. Provisional Application 60/856,490 and 60/860,354 and in International Application PCT/US07/23155, which are incorporated herein in its entirety by reference. Methods to direct the differentiation of iPS cells along cardiac lineages is well known by persons of ordinary skill in the art, and are disclosed in WO2010/00703, WO2009/145761, US2009/0202498, WO2009/097411, WO2009/118928, US2009/0202498 and US2008/0187494, which are incorporated herein in their entirety by reference.

In some embodiments, the tissue or cell populations are inserted, typically by surgical transplantation procedures into a host subject. In some embodiments, the location that the transplant is inserted is determined on the type of tissue or cell population to be transplanted. In some embodiments, the tissue or cell population is transplanted at a desired location for the transplant, and can be, for example, muscles, Liver, Lung, Subcutaneous Fat, Peritoneal Space, Sphincters (all types), Trachea, Brain, Pancreas, Skin, Eye, and intra-vascular, intracoronary, intra-arterial sites, as well as bone surfaces.

The skilled artisan will appreciate that such stromal cells, stem cells, and/or Relevant Cells may be incorporated into a transplant with mixed SVF cells or SVF-matrix construct (for encapsulating a tissue or cell transplant) during or after preparation. For example, but not limited to, combining stem cells, Relevant Cells, in a liquid three-dimensional culture, such as collagen, fibrin, or the like, or seeding or sodding stem cells, Relevant Cells, in or on a transplant with mixed SVF cells or SVF-matrix construct may be achieved. Exemplary combinations of appropriate stem cells, stromal cells, and Relevant Cells for incorporation into transplant with mixed SVF cells or SVF-matrix construct include: islets of Langerhans and/or pancreatic acinar cells in a SVF-matrix construct for revascularizing a damaged pancreas; hepatocytes, hepatic progenitor cells, Kupffer cells, endothelial cells, endodermal stem cells, liver fibroblasts, and/or liver reserve cells in a SVF-matrix construct for revascularizing a damaged liver For example, but not limited to, appropriate stem cells or stromal cells for a SVF-matrix construct for vascularizing, repairing, and reconstructing a damaged or disease liver might comprise liver reserve cells, liver progenitor cells, such as, but not limited to, liver fibroblasts, embryonic stem cells, liver stem cells; cardiomyocytes, Purkinje cells, pacemaker cells, myoblasts, mesenchymal stem cells, satellite cells, and/or bone marrow stem cells for revascularizing a damaged or ischemic heart (see, e.g., Atkins et al., J. of Heart and Lung Transplantation, December 1999, at pages 1173 80; Tomita et al., Cardiovascular Research Institute, American Heart Association, 1999, at pages 92 101; Sakai et al., Cardiovascular Research Institute, American Heart Association, 1999, at pages 108 14); and the like In some embodiments, the tissue or cell transplant comprises pancreatic cells, e.g., β-cells or pancreatic islet cells. Methods of isolation of pancreatic islet cells are well known in the art, and include for example the methods as disclosed in U.S. Pat. No. 7,052,829 which is incorporated herein by reference. One methods for isolating human pancreatic islets is as follows: human pancreatic islets are isolated using the tube method of ductal canulation and collagenase infusion, essentially as described by Arita et al., Transplantation 68(5):705 07, 1999. A polyethylene tube (INTRAMEDIC, Clay Adams, Parsippany, N.J.) with a tight-fitted injection needle on one end, a diameter of approximately 0.64 to 1.47 millimeters (mm) depending on the duct size, and of a length similar to the pancreas is used. The tube is inserted into the main duct of a whole pancreas, starting from the head and extending to the tail, and the duct is ligated around the tube. The pancreas is infused and digested with approximately 150-300 mL collagenase solution (3 mL/g pancreas weight), comprising 2-2.3 mg/mL of lots 9 or 522 collagenase P (Boehringer Mannheim, Indianapolis, Ind.). The collagenase-infused pancreas is chopped into small pieces, placed in a digestion chamber with remaining collagenase solution and gently agitated in a 37° C. water bath. Total incubation time in collagenase is 15 minutes. The collagenase solution is replaced by cold LAP-1 preservation solution (Islet Technology, North Oaks, Minn.) and the digestion chamber is placed in an ice-water bath and gently agitated. The supernatant, containing islets and fragmented acinar and duct tissue, is decanted every 5-10 minutes into collection bottles containing LAP-1 solution and fetal bovine serum. Fresh LAP-1 solution is added to the digestion chamber and cold digestion continues until most of the islets are released, approximately 30-40 minutes. The digested tissues are collected and islets are purified by centrifugation on a discontinuous three-layer gradient of Euro-Ficoll solution using a COBE2991 cell processor (COBE Laboratories, Lakewood, Colo.).

Numerous other islet purification techniques, generally known in the art, may also be employed. Exemplary islet purification techniques may be found in, among other places, London et al., in Methods in Cell Transplantation, Ricordi, ed., at pages 439 54, 1995; Lakey et al., Transplantation 72:562 63, 2001; Olack et al., Human Immunol 60:1303 09, 1999; London et al., Diabetes Metab. 24:200 07, 1998; Linetsky et al., Diabetes 46:1120 23, 1997; Arita et al., Pancreas 23:62 67, 2001; and Wang et al., Nat. Biotechnol. 15:358 62, 1997. The person of ordinary skill in the art will understand that such isolated pancreatic islets may be useful as Relevant Cells in, for example, prevascularized constructs for revascularizing a damaged or diseased pancreas.

In alternative embodiments, the tissue or cell transplant can comprise cells, e.g., ES cells or iPS cells which have undergone directed differentiation along pancreatic lineages into pancreatic cells or pancreatic progenitor cells. Methods to differentiate ES cells or iPS cells along pancreatic lineages are well known by persons of ordinary skill in the art, and are disclosed in WO2005/097977, WO2009/143241, WO2010/051213, WO2010/051223, WO2006/094286, WO2010/051213, WO2007/130474 which are incorporated herein in their entirety by reference. A primary iPS cell can be differentiated into a pancreatic cell linage. The pancreas is composed of exocrine and endocrine compartments. The endocrine compartment consists of islets of Langerhans, clusters of four cell types that synthesize peptide hormones: insulin (beta cells), glucagon (alpha cells), somatostatin (gamma cells), and pancreatic polypeptide (PP cells).

IV. Stromal Vascular Fraction Cells (SVFs)

VI. (a) Stromal Vascular Fraction Cells (SVFs)

Stromal vascular fraction cells (SVFs) are also commonly referred to in the art as adipose derived stromal cells or "ASCs" or "ADSL", and refer to a heterologous population of cells derived from digestion of adipose tissue. This population of cells is referred to as "SVF" or "stromal vascular fraction" cells herein.

Without wishing to be bound to theory, adipose tissue plays an important and overlooked role in the normal development and physiology of humans and other mammalian species. Many different kinds of fat exist. The most common type is white adipose tissue, located under the skin (subcutaneous fat), within the abdominal cavity (visceral fat) and around the reproductive organs (gonadal fat). Less common in the adult human is brown adipose tissue, which plays an important role in generating heat during the neonatal period; this type of fat is located between the shoulder blades (interscapular), around the major vessels and heart (periaortic and pericardial), and above the kidney (suprarenal). Adipose tissue also encompasses yellow fat. Adipose tissue is found throughout the body of an animal, including humans, and is present in the omementurm, bone marrow, subcutaneous space and surrounding most organs.

Adult SVF or human SVF represent a cell source that can be harvested routinely with minimal risk or discomfort to the subject. They can be expanded ex vivo, differentiated along unique lineage pathways, genetically engineered, and reintroduced into individuals as either autologous or allogenic transplantation.

A population of SVF as described herein, comprise is a heterologous population of cells comprising at least one or at least 2 or the following population of cells; endothelial cells, mesenchymal stem cells, fibroblasts, smooth muscle cells, pericytes and adipose-derived stem cells, as well as additional other cell types not listed. In some embodiments, adipose-derived stromal cells refers to a substantially pure population of adipose-derived stem cells. In some embodiments, adipose-derived stromal cells does not refers to adipose derived regenerative cells. SVF useful in the methods of the present invention have the ability to differentiate into various cell types, including, but no limited to, adipocytes, chondrocytes, and osteoblasts, as well as provide fully differentiated and functional cells for research, transplantation, and development of tissue engineering products for the treatment of diseases and disorders and traumatic injury repair.

SVF cells described herein can be isolated from adipose tissue using methods previously described (Zuk et al., Tissue Engineering 7:211, 2001; Katz et al., Stem Cells 23:412, 2005). However, one of ordinary skill in the art will appreciate that culture conditions such as cell seeding SVF densities can be selected for each experimental condition or intended use.

SVF cells can be cultured according to method commonly known in the art to induce the SVFs to give rise to cells having a mesodermal, ectodermal or endodermal lineage. After culturing SVFs in the differentiating-inducing medium for a suitable time (e.g., several days to a week or more), the SVFs can be assayed to determine whether, in fact, they have acquired the desired lineage.

Methods to characterize a population of SVFs, include, but are not limited to, histological, morphological, biochemical and immunohistochemical methods, or using cell surface markers, or genetically or molecularly, or by identifying factors secreted by the differentiated cell, and by the inductive qualities of the differentiated SVFs. US 2002/0076400 and WO 00/53795 (which are incorporated herein by reference) describe the production of multipotent cell populations from human adipose tissue. Said cell populations can be differentiated into adipocytes, osteoblasts, chondrocytes, and myocytes. The publications indicate that some of the cells they can be maintained in culture in vitro for at least 15 cell transfers without losing their multipotent character. U.S. Pat. No. 6,800,480, which is incorporated herein by reference, describes methods and materials for growing primate-derived primordial stem cells in a feeder cell-free culture system.

For example, molecular markers that characterize mesodermal cell that differentiate from the SVFs of the invention, include, but are not limited to, MyoD, myosin, alpha-actin, brachyury, FOG, tbx5 FoxF1, Nkx-2.5. Mammalian homologs of the above mentioned markers are preferred.

Molecular markers that characterize ectodermal cell that differentiate from the SVFs of the invention, include for example, but are not limited to N-CAM, GABA and epidermis specific keratin. Mammalian homologs of the above mentioned markers are preferred. Molecular markers that characterize endodermal cells that differentiate from the SVFs include for example, but are not limited to, Xhbox8, Endo1, Xhex, Xcad2, Edd, EF1-alpha, HNF3-β, LFABP, albumin, insulin. Mammalian homologs of the above mentioned markers are preferred.

Other techniques useful for isolating and characterizing the SVFs as described herein include fractionating cells using cell markers. The immunophenotype of the SVFs based on flow cytometry include Stromal cell—associated markers, such as CD13, CD29, CD34, CD44, CD63, CD73, CD90, CD166, as well as aldehyde dehydrogenase and the multidrug-resistance transport protein (ABCG2). ASC can also express endothelial cell—associated markers, such as for example but not limited to, CD31, CD144 or VE-cadherin, vascular endothelial growth factor receptor 2, von Willebrand factor.

SVFs also express a number of adhesion and surface proteins. These include cell surface markers such as CD9; CD29 (integrin β1); CD44 (hyaluronate receptor); CD49d,e (integrin alpha 4, 5); CD54 (ICAM1); CD55 (decay accelerating factor); CD105 (endoglin); CD106 (VCAM-1); CD166 (ALCAM) and HLA-ABC (Class I histocompatibility antigen); and cytokines such as interleukins 6, 7, 8, 11; macrophage-colony stimulating factor; GM-colony stimulating factor; granulocyte-colony stimulating factor; leukemia inhibitory factor; stem cell factor and bone morphogenetic protein. Many of these proteins have the potential to serve a hematopoietic supportive function and all of them are shared in common by bone marrow stromal cells.

In some embodiments, the SVFs are genetically engineered. In certain embodiments, a SVF is genetically engineered to express at least one cytokine, chemokine, antibiotic, drug, analgesic, anti-inflammatory, or immune suppressants, or the like. Exemplary cytokines include angiogenin, vascular endothelial growth factor (VEGF, including, but not limited to VEGF-165), interleukins, fibroblast growth factors, for example, but not limited to, FGF-1 and FGF-2, hepatocyte growth factor, (HGF), transforming growth factor beta (TGF-β), endothelins (such as ET-1, ET-2, and ET-3), insulin-like growth factor (IGF-1), angiopoietins (such as Ang-1, Ang-2, Ang-3/4), angiopoietin-like proteins (such as ANGPTL1, ANGPTL-2, ANGPTL-3, and ANGPTL-4), platelet-derived growth factor (PDGF), including, but not limited to PDGF-AA, PDGF-BB and PDGF-AB, epidermal growth factor (EGF), endothelial cell growth factor (ECGF), including ECGS, platelet-derived endothelial cell growth factor (PD-ECGF), placenta growth factor (PLGF), and the like. The skilled artisan will understand that the choice of chemokines and cytokine fragments to be expressed by engineered SVFs will depend, in part, on the target tissue or organ to be vascularized or revascularized.

In certain embodiments, a composition comprising a SVF cell on a three-dimensional (3D) matrix, e.g., a three-dimensional biocompatible matrix further comprise at least one genetically engineered SVF cell. In certain embodiments, a genetically engineered SVF cell will constitutively express or inducibly express at least one gene product encoded by the at least one genetically engineered cell due to the genetic alterations within the at least one genetically engineered cell induced by techniques known in the art. Descriptions of exemplary genetic engineering techniques can be found in, among other places, Ausubel et al., Current Protocols in Molecular Biology (including supplements through March 2002), John Wiley & Sons, New York, N.Y., 1989; Sambrook et al., Molecular Cloning: A Laboratory Manual, 2nd Ed., Cold Spring Harbor Laboratory Press, Cold Spring Harbor, N.Y., 1989; Sambrook and Russell, Molecular Cloning: A Laboratory Manual, 3rd Ed., Cold Spring Harbor Laboratory Press, Cold Spring Harbor, N.Y., 2001; Beaucage et al., Current Protocols in Nucleic Acid Chemistry, John Wiley & Sons, New York, N.Y., 2000 (including supplements through March 2002); Short Protocols in Molecular Biology, 4th Ed., Ausbel, Brent, and Moore, eds., John Wiley & Sons, New York, N.Y., 1999; Davis et al., Basic Methods in Molecular Biology, McGraw Hill Professional Publishing, 1995; Molecular Biology Protocols (see the highveld.com website), and Protocol Online (protocol-online.net). Exemplary gene products for genetically modifying the genetically engineered SVF cells of the invention include, plasminogen activator, soluble CD4, Factor VIII, Factor IX, von Willebrand Factor, urokinase, hirudin, interferons, including α-, β- and γ-interferon, tumor necrosis factor, interleukins, hematopoietic growth factor, antibodies, glucocerebrosidase, adenosine deaminase, phenylalanine hydroxylase, human growth hormone, insulin, erythropoietin, VEGF, angiopoietin, hepatocyte growth factor, PLGF, and the like.

IV(b). Methods to Obtain SVFs

Adipose tissue is readily accessible and abundant in many individuals. Obesity is a condition of epidemic proportions in the United States, where over 50% of adults exceed the recommended BMI based on their height. Adult adipose-derived stromal cells (ASC) can be harvested from a subject, for example, using the methods and devices as disclosed in U.S. Pat. No. 7,270,996, which is incorporated herein by reference. Additionally, adult adipose-derived stromal cells (ASC) can be obtained and cultured according to the culture conditions as disclosed in U.S. Patent Application 2008/0248003 which is incorporated herein by reference.

SVFs useful in the methods of invention can be isolated by a variety of methods known to those skilled in the art such as described in US Patent Application 2003/0082152 or WO 00/53795 or U.S. Pat. Nos. 4,820,626, 4,883,755, 5,035,708 and 5,957,972, which are all incorporated herein in their entirety by reference.

Alternatively, the process of isolating the SVFs enriched fraction can be performed using a suitable device, many of which are known in the art (see, e.g., U.S. Pat. No. 5,786,207 which is incorporated herein in its entirety by reference). Such devices can mechanically achieve the washing and dissociation steps if obtaining SVFs from adipose tissue.

In some embodiments, adipose tissue is isolated from a mammalian subject, preferably a human subject. In some embodiments, a source of adipose is subcutaneous adipose tissue. In some embodiments, a source of adipose tissue is omental adipose. In humans, the adipose is typically isolated by liposuction.

In some embodiments, the SVFs for use in the compositions and methods as disclosed herein (e.g. SVFs in a transplant mixed with SVF cells or a transplant encapsulated with SVF cells) are isolated from the adipose tissue obtained from that same subject (i.e. recipient host subject) which will receive the transplant. Thus, in one embodiment, for example the use of SVFs isolated from the recipient subject can be used to encapsulate a organ/tissue or cells which is from donor (non-recipient) subject, thus effectively changing an allogenic organ transplantation procedure into an autologous organ transplantation procedure. Alternatively, in some embodiments, the SVFs are from a non-recipient subject, and thus the organ/tissue/cells and SVFs (either encapsulating the organ/tissue/cells or mixed within the cells or issue) which are transplanted are allogenic.

One can use any method for isolation of SVF to obtain SVFs for the methods and compositions for mixing in with cells/tissue to be transplanted or encapsulating tissue/cells to be transplanted. For example, a person of ordinary skill in the art can use any methods for the isolation, expansion, and differentiation of human SVFs which as been previously reported. See for example, Burris et al. 1999, Mol Endocrinol 13:410-7; Erickson et al. 2002, Biochem Biophys Res Commun. Jan. 18, 2002; 290(2):763-9; Gronthos et al. 2001, Journal of Cellular Physiology, 189:54-63; Halvorsen et al. 2001, Metabolism 50:407-413; Halvorsen et al. 2001, Tissue Eng. 7(6):729-41; Harp et al. 2001, Biochem Biophys Res Commun 281:907-912; Saladin et al. 1999, Cell Growth & Diff 10:43-48; Sen et al. 2001, Journal of Cellular Biochemistry 81:312-319; Zhou et al. 1999, Biotechnol. Techniques 13: 513-517. Adipose tissue-derived stromal cells are obtained from minced human adipose tissue by collagenase digestion and differential centrifugation [Halvorsen et al. 2001, Metabolism 50:407-413; Hauner et al. 1989, J Clin Invest 84:1663-1670; Rodbell et al. 1966, J Biol Chem 241:130-139].

It is well documented that adipocytes are a replenishable cell population. Even after surgical removal by liposuction or other procedures, it is common to see a recurrence of adipocytes in an individual over time. This suggests that adipose tissue contains stromal stem cells and/or precursors that are capable of self-renewal.

However obtained, the adipose tissue is processed to separate the SVFs of the invention from the remainder of the adipose tissue. The SVFs population that contains a heterogeneous population of mesenchymal stem cells, fibroblasts, smooth muscle cells and pericytes and adipose-derived stem cells is obtained by washing the obtained adipose tissue with a physiologically-compatible solution, such as phosphate buffer saline (PBS). The washing step consists of rinsing the adipose tissue with PBS, agitating the tissue, and allowing the tissue to settle. In addition to washing, the adipose tissue is dissociated. The dissociation can occur by enzyme degradation and neutralization. Alternatively, or in conjunction with such enzymatic treatment, other dissociation methods can be used such as mechanical agitation, sonic energy, or thermal energy. Three layers form after the washing, dissociation, and settling steps. The top layer is a free lipid layer. The middle layer includes the lattice and adipocyte aggregates. The middle layer is referred to as an "adipose-derived lattice enriched fraction."

The bottom layer contains the SVFs population. The bottom layer is further processed to isolate the SVFs as disclosed herein. The cellular fraction of the bottom layer is concentrated into a pellet. One method to concentrate the cells includes centrifugation. The bottom layer is centrifuged and the pellet is retained. The pellet is designated the adipose-derived stromal cell population which includes the adipose-derived stem cells as well as other cells in the ASC population. The SVF cell population can also contain erythrocytes (RBCs). In a preferred method the RBCs are lysed and removed. Methods for lysis and removed RBCs are well known in the art (e.g., incubation in hypotonic medium). However, the RBCs are not required to be removed from the SVFs -EF. The pellet is resuspended and can be washed (in PBS), centrifuged, and resuspended one or more successive times to achieve greater purity of the SVFs. The SVFs population as disclosed herein is a heterogenous population of cells which include, among other cells, adipose-derived stem cells (ADSCs). The cells of the washed and resuspended pellet are ready for genetic manipulation and subsequent transplantation into a subject.

The SVFs in the resuspended pellet can be separated from other cells of the resuspended pellet by methods that include, but are not limited to, cell sorting, size fractionation, granularity, density, molecularly, morphologically, and immunohistologically. The immunophenotype of the adipose-derived stromal cells based on flow cytometry include Stromal cell—associated markers, such as CD13, CD29, CD34, CD44, CD63, CD73, CD90, CD166, as well as aldehyde dehydrogenase and the multidrug-resistance transport protein (ABCG2). SVFs can also express endothelial cell—associated markers, such as for example but not limited to, CD31, CD144 or VE-cadherin, vascular endothelial growth factor receptor 2, von Willebrand factor.

In one embodiment, the SVFs are separated from the other cells on the basis of cell size and granularity where SVFs are small and agranular. Alternatively, a molecular method for separating the SVFs from the other cells of the pellet is by assaying the length of the telomere. SVFs tend to have longer telomeres than differentiated cells.

In another embodiment, a biochemical method for separating the SVFs from the other cells of the pellet is used by assaying telomerase activity. Telomerase activity can serve as a stem cell-specific marker.

In still another embodiment, the SVFs are separated from the other cells of the pellet immunohistochemically, for example, by panning, using magnetic beads, or affinity chromatography.

Adipose tissue offers many practical advantages for tissue engineering applications. First, it is abundant. Second, it is accessible to harvest methods with minimal risk to the patient. Third, it is replenishable. While stromal cells represent less than 0.01% of the bone marrow's nucleated cell population, there about at least $8.6 \times 10^4$ or at least $8.6 \times 10^6$ stromal cells or SVFs per gram of adipose tissue (Sen et al., 2001, J. Cell. Biochem., 81:312-319). Ex vivo expansion over 2 to 4 weeks yields up to 500 million stromal cells or SVFs from 0.5 kilograms of adipose tissue.

Accordingly, in some embodiments SVFs for use in the compositions and methods as disclosed herein can be used immediately in mixing with cells for transplantation, or for coating a tissue or cell or cell mass to be transplanted. In alternatively, in some embodiments, the SVFs can be cryopreserved for future autologous or allogenic applications for use in mixing with cells to be transplanted or for coating transplanted tissue and cells in future transplantation procedures.

IV(c) Culturing the SVFs

In one embodiment, SVFs derived from adipose tissue, are subjected to varied culture media conditions as described herein to support growth or differentiation under serum-free or low serum conditions. One of ordinary skill in the art will appreciate that the amount of each growth factor, hormone, compound, nutrient, vitamin, etc., used may vary according to the culture conditions, amount of additional differentiation-inducing agent used, or the number of combination of agents used when more than one agent is used.

V Three-Dimensional Matrix

V(a) Combination of SVF Cells with Other Cells in Three-Dimensional Matrix.

As discussed herein, a population of SVF cells for use in a transplant mixed with SVF cells or a transplant encapsulated with SVF cells which encapsulates can be present or within a three-dimensional matrix. The SVF cells can be alone in the three-dimensional matrix (e.g. when the population of SVF cells is used to encapsulate a tissue or cell transplant), or the SVF cells can be present with other cells, e.g. when a population of SVF cells are mixed with cells in a cell transplants. In some embodiments, other cell types and populations are present. In some embodiments, where SVF cells are mixed with cells of the cell transplants, and they are present in three-dimensional matrix, microvessel fragments are not present.

In addition to the population of SVF cells, a skilled artisan will appreciate that the effective concentration of each additional cell type (e.g., cells of the cell transplant or other relevant cell types) within the three-dimensional matrix, and is dependent on the cell type and the intended use of the SVF-matrix construct. Thus, the person of ordinary skill will understand that it is routine to titrate each cell type in test SVF-matrix constructs to identify the effective concentration for a particular use. For example, to determine the effective concentration of SVF cells in SVF-matrix constructs, test constructs prepared according the methods as disclosed herein, and could be prepared as follows. Eighteen parallel liquid three-dimensional culture preparations comprising 13,000 human SVF cells each and either 0, 10, 100, 1000, 10000, or 50,000 of cells to be transplanted per/ml are prepared in six triplicate sets, and allowed to polymerize. The 18 parallel constructs are combined with target tissues or organs by implanting the constructs directly into test animals, by methods commonly known by a skilled artisan. After an appropriate implantation period, the SVF-matrix constructs would be explanted and the recipient animal, the implant, and the relevant tissue or organ would be evaluated. To evaluate the effect of the additional cell type(s) on the proliferation and growth microvessel fragments in cultured SVF-matrix, similar triplicate constructs could also be incubated, for example in a humidified 37° C., 5% $CO_2$ incubator, and evaluated over a seven to ten day period.

The skilled artisan will understand that further refinement of the appropriate number of additional cells for a particular SVF-matrix construct can be determined by additional experiments, based on the results of the above procedure. For example, if in the first experiment that 1000 additional cells/ml demonstrated the best results, additional tests using 500, 2000 and 6000 cells/ml would allow further refinement of the optimal number of additional cells per SVF-matrix construct. A similar procedure could be followed to determine the appropriate concentration of an additional cell type, such as other relevant Cells, genetically engineered cells, or combinations thereof, in a SVF-matrix construct.

In some embodiments, the cell or tissue to be transplanted is present on the surface or embedded in a three-dimensional biocompatible matrix. A three-dimensional biocompatible matrix can include a variety of scaffold matrices including fibrin gels and artificial, FDA-approved synthetic biocompatible polymers are encompassed for use in the methods and compositions as disclose herein.

The skilled artisan will understand that composition matrices comprising a population of SVF cells and/or cells of interest and a nonpolymerized liquid three-dimensional matrix that is subsequently allowed to polymerize or gel are capable of assuming a multitude of shapes. Thus, in certain embodiments, the ultimate size and shape of the polymerized composition matrices depends, in part, on the size and shape of the vessel in which the construct is polymerized. For example, but not limited to, cylindrical or tubular constructs can be prepared using conical tubes; disk-shaped constructs can be prepared using multi-well plates; planar constructs can be prepared using flat surfaces, for example, a petri dish, the inverted lid of a multi-well plate, or a flat-bottomed dish. Additionally, in certain embodiments, polymerized composition matrices can be cut or trimmed into a desired size or shape. Thus, composition matrices comprising a population of SVF cells and/or cells of interest can be prepared in virtually any size and shape, prior to or during use.

In certain embodiments, the composition matrices comprising a population of SVF cells and/or cells of interest comprises autologous SVF cells in an autologous or substantially autologous three-dimensional culture. In certain embodiments, composition matrices comprising a population of SVF cells and/or cells of interest comprise SVF cells in a three-dimensional culture comprising a scaffold, for example, but not limited to, fibrin-derived scaffolds (see, e.g., Nicosia et al., Lab. Invest. 63:115 22, 1990) and scaffolds comprising artificial, FDA-approved synthetic biocompatible polymers, for example, but not limited to, polyethylene, polymethacrylate, polyurethane, vinyl, such as polyvinyl chloride, silicones, PLGA, PTFE, ePTFE, polypropylene, polyethyleneterephthalate (PET), nylon, polylactide, and polyglycolide. Discussions of exemplary biocompatible polymers, scaffolds, and other matrix materials, including protocols for their preparation and use, may be found in, among other places, Atala et al., particularly Chapters 42 76; Lanza et al., particularly Chapters 21 and 22; and Handbook of Biodegradable Polymers, Domb, Kost, and Domb, eds., 1997, Harwood Academic Publishers, Australia V(b) Methods to Prepare a Matrix with SVF Cells, for Transplants Mixed with SVF Cells or for a SVF-Matrix to Encapsulate a Tissue or Cell Transplant Any method to prepare a three-dimensional matrix with SVF cells can be used. By way of an example, one method is as follows: a suspension comprising approximately 13,000 SVFs/mL, obtained from liposuction fat according to the methods as disclosed herein, in the nonpolymerized collagen solution, containing 2 ng/ml human $VEGF_{165}$ and 1 ng/ml human PDGF-BB (both from R&D Systems, Minneapolis, Minn.) is prepared. In some embodiments, such as in the preparation of a transplant at mixed with SVF cells, the transplant cells (approximately an equal amount of transplant cells to SVF cells, e.g. 13,000 cells/mL) are also included in the non-polymerized collagen solution. In some embodiments, such as in the preparation of a transplant encapsulated with SVF cells, microvessel fragments can be included, according to the methods as disclosed in U.S. Pat. No. 7,052,829.

Next, a 5 cm×7 cm piece of polyglycolic acid (PGA) felt (Albany International) with a pore size ranging from 2 15 µm and one mm thick is placed in a sterile glass pan. The suspension is gently poured into the glass pan until the felt is covered forming a SVF-matrix construct. The SVF-matrix construct is incubated at room temperature until polymerization occurs. A slice is made through the SVF-matrix construct along the edge of the PGA felt using a sterile scalpel.

The SVF-matrix construct comprising the felt is gently removed from the dish and placed directly on top of a 5 cm×7 cm piece of freshly thawed DERMAGRAFT®. human fibroblast-derived dermal substitute (Advanced Tissue Sciences, La Jolla, Calif.; see Atala et al., particularly Chapter 104). In some embodiments, e.g. embodiments where SVF-matrix is used in a transplant mixed with SVF cells, the SVF-matrix construct comprising transplant cells can be attached to the DERMAGRAFT® using one suture at each corner of the SVF-matrix construct-engineered tissue composite. After trimming the composite to the size of the tissue or cell transplant, it can be transplanted into a subject. The transplant mixed with SVF cells can be held securely in the transplanted location using surgical dressings.

In alternative embodiments, e.g., a embodiments where a SVF-matrix is used in a transplant encapsulated with SVF cells, the SVF-matrix can be trimmed to the size of the tissue or cell transplant, and affixed to the tissue or cell transplant by a suitable means, such as suture, fastening, glue and the like. The SVF-matrix and tissue or cell transplant composition can be transplanted into a subject. The transplant encapsulated with SVF cells can be held securely in the transplanted location using surgical dressings.

The skilled artisan will understand, based on these illustrative examples, that flexible SVF-matrix constructs may be wrapped around or within engineered tissues, such as DERMAGRAFT, and implanted into a human and cultured to generate vascularized engineered tissue. The skilled artisan will appreciate that SVF-matrix constructs may also be combined with an engineered tissue by placing the construct within the tissue. The combination is subsequently implanted and cultured in vivo to generate vascularized tissue. Vascularized engineered tissues may also be prepared, for example, but without limitation, combining at least one inflexible SVF-matrix constructs with an engineered tissue, before or after the tissue is implanted in a human patient. The skilled artisan will also appreciate that these techniques may be used with any engineered tissue to produce a vascularized engineered tissue.

VI. Microvessel Fragments

In some embodiments, the SVF cells are used to promote vascularization of a tissue or cell transplant. In some embodiments, the tissue or cell transplant is present on the surface of, or embedded within a 3D biocompatible matrix. In some embodiments, e.g. embodiments where SVF cells are used in a transplant mixed with SVF cells, the matrix comprises the transplant cells, a population of SVF cells, and in some embodiments does not comprise microvessel fragments.

In another embodiments, e.g. embodiments where SVF cells are used in a transplant mixed with SVF cells, the matrix comprises the transplant cells, a population of SVF cells, and in some embodiments can optionally comprise microvessel fragments. For example, in such an embodiment, the matrix, such as a gel comprises a heterologous population of cells, comprising SVF cells comingled (i.e. mixed in) with microvessel fragments comingled with the transplant cells. In certain embodiments, such a composition comprising a population of SVF cells, a population of cells of interest to be transplanted and microvessel fragments are prepared by combining; (i) a population of SVF cells with, (i) a population of cells of interest to be transplanted with, (iii) microvessel fragments, and (iv) a liquid three-dimensional matrix, such as nonpolymerized collagen, agarose, gelatin, other nonpolymerized polymer matrices, or the like. In other embodiments, a population of SVF cells and transplant cells (and optionally microvessel fragments) are seeded, sodded or perfused onto or through a solid or semi-solid three-dimensional matrix, for example, but not limited to, a framework, scaffold, hollow-fiber filter, or the like.

In an alternative embodiment, e.g. embodiments where SVF cells are used in a transplant encapsulated with SVF cells, a SVF-matrix construct, can further comprises microvessel fragments, to form a SVF-MV-matrix construct. Stated another way, SVF cells for use to encapsulate a tissue or cell transplant can be present on the surface of (such as in a single layer or multiple cell layer) of a matrix which comprises microvessel fragments. In an alternative embodiment, SVF cells for use to encapsulate a tissue or cell transplant can be embedded within a matrix which comprises microvessel fragments. Such matrices which comprise microvessel fragments are referred to as "pre-vascularized construct" and methods of their production are disclosed in U.S. Pat. Nos. 7,052,829 and 7,029,838 (which are incorporated herein in their entirety by reference). The terms "SVF-MV-matrix construct" refers to a composition comprising at least one SVF cell either on the surface of the matrix or embedded within, at least one microvessel fragment embedded within the matrix, where the matrix is a three-dimensional matrix, including but not limited to a matrix, scaffold, gel, or liquid.

Accordingly, in certain embodiments, a prevascularized construct as disclosed in U.S. Pat. Nos. 7,052,829 and 7,029,838 can be encapsulated with a single cell layer or multiple cell layer of SVF cells, or embedded with SVF cells to form a SVF-MV-matrix construct, where the SVF-MV-matrix construct encapsulates (e.g. partially or substantially surrounds or covers) a tissue or cell transplant. In certain embodiments, the matrix comprises a preformed framework, for example, but not limited to a fibrin scaffold. In certain embodiments, the three-dimensional culture comprises a polymerized, substantially polymerized, or nonpolymerized matrix.

In certain embodiments, a SVF-MV-matrix construct for encapsulating a tissue or cell transplant are prepared by combining SVF cells and microvessel fragments and a liquid three-dimensional culture, such as nonpolymerized collagen, agarose, gelatin, other nonpolymerized polymer matrices, or the like. In other embodiments, the SVF cells are seeded, sodded or perfused onto or through a solid or semi-solid three-dimensional matrix which comprises microvessel fragments embedded within, for example, but not limited to, a framework, scaffold, hollow-fiber filter, or the like.

Any means to obtain microvessel fragments can be used, which can be from any subject, mammalian or otherwise, and in some embodiments, the microvessel fragments are obtained from humans. In some embodiments the microvessel fragments are isolated from a patient's adipose tissue harvested by liposuction. To isolated microvessel fragments, the method of isolating single endothelial cells may be used as described in U.S. Pat. No. 5,957,972, the entire contents of which are incorporated by reference. In some embodiments, harvested microvessel fragments would be placed into a three-dimensional culture using fibrin derived from the patient's own blood as the 3-D matrix scaffold. In this manner, a patient would receive his own (autologous) vessels after a brief culture period (e.g., one hour to 30 days).

Isolation of microvessel fragments is well known in the art. By way of example only, isolation of rat microvessel fragments is disclosed, although the same procedure can be readily modified for isolation of human microvessel fragments. Rat fat microvessel fragments (RFMF) were isolated from the epididymal fat pads (8 to 10 milliliters (mLs)) of retired breeder Sprague Dawley or Fischer 344 rats, essentially as described (Carter et al., Surgery, 120:1089 94, 1996). Harvested fat pads were washed in EFAF-PBS (Dulbecco's cation-free phosphate buffered saline (DCF-PBS) supplemented with 0.1% essentially fatty acid free BSA (EFAFBSA; fraction V Sigma, St. Louis, Mo.), finely minced, placed in an Erlenmeyer flask containing a stir bar, and digested in PBS supplemented with 2 mg/mL collagenase (Worthington Biochemicals) and 2 mg/mL bovine serum albumin (BSA) for 10 minutes at 37° C. with shaking for mechanical-assisted enzymatic disruption. The solution was placed in a room temperature centrifuge and the microvessel fragments were pelleted at 700×g for 3 minutes.

Vessel fragments were transferred to 15 or 50 mL polypropylene conical tubes (Falcon), washed using approximately 12 mLs of EFAF-PBS and separated from adipose cells by centrifugation in an IEC tabletop centrifuge at 600 700×g for 3 minutes. Following centrifugation the fat cake was removed by decanting and the pelleted microvessel fragments were suspended in 12 ml EFAF-PBS. Tissue debris and large vessel pieces were removed by filtering through a nylon screen of 500 µm pore size. RFMF were collected from the filtrate by screening the filtrate through a nylon screen of 30 micron pore size. The RFMF were collected from the screen, placed in 15 mL polypropylene conical tubes, washed twice by pipetting using approximately 12 mLs of EFAF-PBS per wash, and centrifuged as before. The isolated microvessel fragments can be used in a three-dimensional matrix to form prevascularized constructs as disclosed in U.S. Pat. No. 7,052,829, which is incorporated herein by reference.

SVF-MV-matrix construct for encapsulating a tissue or cell transplant can be categorized as "cultured SVF-MV-matrix construct" or "freshly isolated SVF-MV-matrix construct." A cultured SVF-MV-matrix construct is typically incubated prior to implantation. For example, but not limited to, in a humidified incubator at 37° C. and 5% $CO_2$. Typically such cultured SVF-MV-matrix constructs are incubated for a period of one hour to thirty days, but may be incubated for shorter or longer periods, as desired. The skilled artisan will appreciate that the term "cultured" may or may not refer to the use of conventional incubation methods, such as a controlled-temperature incubator. Alternately, a freshly isolated SVF-MV-matrix construct refers to a SVF-MV-matrix construct which comprises a freshly isolated SVF cells and/or microvessel fragments that undergoes little or no incubation prior to use. The skilled artisan will appreciate that freshly isolated SVF-MV-matrix constructs can, but need not, be incubated. In certain embodiments, a freshly isolated SVF-MV-matrix construct comprises SVF cells on, or within a three-dimensional culture that has been "incubated" subsequent to the introduction of the SVF cells and/or microvessel fragments, for example, but without limitation, to allow the construct to polymerize. In other embodiments, a freshly isolated SVF-MV-matrix construct comprises a liquid three-dimensional culture, as may be appropriate for implantation by injection (see, e.g., U.S. Pat. Nos. 5,709,854 and 6,224,893). Such liquid constructs may, but need not, polymerize in situ under appropriate conditions.

VII. Application of SVF to a Transplant Surface

According to the methods and compositions as disclosed herein, SVF cells enhance vascularizing of tissue and/or cell transplants, including engineered tissues. In some embodiments, a layer of SVF cells, such as a single or multiple cell layer or a SVF-matrix is used to encapsulate a tissue or cell transplant. In such embodiments, a SVF-matrix is combined with a tissue or cell transplant. The term "combining" comprises placing or implanting at SVF-matrix on any surface of, within, between layers of, or adjacent to, a tissue or cell transplant. In certain embodiments, combining comprises coating the tissue or cell transplant with SVF cells or a SVF matrix construct. For example, but without limitation, a tissue or cell transplant is dipped into a liquid SVF matrix construct or a liquid SVF cells are poured or sprayed on an engineered tissue. In certain embodiments, such liquid SVF matrix construct coating the tissue or cell transplant is polymerized. In certain embodiments, such transplant encapsulated in SVF cells is incubated prior to implantation into a recipient animal or human.

In certain embodiments, a transplant encapsulated in SVF cells comprises attaching at SVF-matrix to at least one tissue or cell transplant, using techniques known in the art. Exemplary attachment means include suturing, stapling, for example, with surgical staples, glue or adhesive, such as surgical glue, biochemical interactions such as with the extracellular matrix, photo-activated glue, fibrin glue, acrylate-based adhesives, and the like.

In certain embodiments, the SVF-matrix construct is inserted within an incision in the tissue or cell transplant. In certain embodiments, combining comprises wrapping at least one SVF-matrix construct around or within at least tissue or cell transplant, such that the SVF-matrix construct envelopes or substantially envelopes the tissue or cell transplant. In certain embodiments, combining comprises forming or incorporating at least one SVF-matrix construct into the tissue or cell transplant during a tissue engineering process. In certain embodiments, combining comprises culturing at least one SVF-matrix construct on or within a growing engineered tissue during the tissue engineering process, such as in a bioreactor. In certain embodiments, at least one SVF-matrix construct is enveloped or substantially enveloped by the adjacent tissue or organ during the tissue engineering process.

In certain embodiments, the SVFs of a transplant mixed with SVF cells are combined with the tissue or cell transplant by injection. The terms "injecting", "injection", or variations thereof as used herein shall refer to any means of ejecting or extruding a substance, typically through a tube or structure comprising a bore or external opening. Such tube or structure can be flexible, inflexible, or can comprise at least one flexible portion and at least one inflexible portion. Exemplary injection means include a syringe with or without a needle, a cannula, a catheter, flexible tubing, and the like. Delivery of a prevascularized construct might also be accomplished through the use of devices that permeablize tissue, such as microneedles. In contrast to traditional injections with standard-gauge hypodermic needles, microneedle (typically defined by a radius of curvature about 1 µm) or microneedle arrays permeabilize the skin or endothelial cell layer by producing microscopic holes. These holes, in effect, act as conduits for materials delivery and may enhance the attachment or delivery of a population of SVF to a vessel, tissue, or organ. Thus, the skilled artisan will understand that any structure comprising a bore or external opening through which a population of SVF cells can be extruded on or into a tissue or organ, is within the intended scope of the invention. In certain embodiments, such injected construct polymerizes in situ, following injection.

In certain embodiments, the transplant mixed with SVF cells or transplant encapsulated with SVF cells are incubated, for example within a bioreactor or humidified incubator, prior to in vivo implantation into a recipient animal or human. In certain embodiments, a transplant mixed or encapsulated with SVF cells is implanted directly into a recipient animal or human with little or no additional incubation.

In certain embodiments, the transplant mixed or encapsulated with SVF cells serves as a nucleation site for vascularizing the engineered tissue. In certain embodiments, appropriate additional cells, e.g. stem cells, and/or Relevant Cells from the transplant mixed or encapsulated with SVF cells will support the integration of the engineered tissue within the recipient animal or human. In some embodiments, the transplant mixed or encapsulated with SVF cells comprise genetically engineered SVF cells to produce recombinant products that are distributed systemically via the bloodstream or delivered to the local microenvironment to induce repair, wound healing, or the like.

VIII. Methods for Revascularizing Damaged or Injured Tissues or Organs

In certain embodiments, methods for revascularizing damaged or injured tissues or organs, i.e., tissues or organs in need of revascularization and repair or reconstruction, are provided. In certain embodiments, transplants mixed or encapsulated with SVF cells are used to revascularize tissues or organs. In some embodiments, a transplant mixed or encapsulated with SVF cells further comprise at least one appropriate stem cell, Relevant Cell, or genetically engineered cell. In certain embodiments, transplants mixed or encapsulated with SVF cells for revascularizing tissues or organs comprise at least one cytokine, chemokine, antibiotic, drug, analgesic, anti-inflammatory, or the like. In certain embodiments, the transplant mixed or encapsulated with SVF cells, once implanted in vivo, will develop a functional vascular bed and inosculate with the surrounding functional vascular system and perfuse, or be capable of perfusing, the damaged tissue or organ.

The skilled artisan understands that certain tissues and organs are covered by or contain a layer of fibrous tissue, connective tissue, fatty tissue, or the like, and that the underlying tissue or organ can be revascularized without removing this layer. Such a layer may be naturally occurring (such as a serosal layer, mucous membrane, fibrous capsule, or the like), may result form fibrosis, necrosis, or ischemia, due to disease, defect, injury, or biochemical deficiency. Typically, the SVF cells of the transplants mixed or encapsulated with SVF cells can penetrate such a layer and inosculate with the vasculature of the underlying tissue or organ, revascularizing the tissue or organ. Thus, combining SVFs in transplants mixed or encapsulated with SVF cells enhances the revasculariztion of the transplant tissue or cell transplant in need of revascularization.

In some embodiments, a SVF-matrix can be directly implanted without the transplant tissue, for example where a tissue is need of revascularization. For example, but not limited to, placing the SVF cells or SVF-matrix construct directly on the meninges to revascularize brain tissue; the epicardium to revascularize the myocardium; the peritoneum and/or serosa, to revascularize portions of the large intestine; the conjunctiva and/or subconjunctiva to revascularize the eye; the tracheal surface to revascularize the trachea; the buccal mucosa to revascularize the mouth; the pleural and/or serosal surface to revascularize the lung; the pleural and/or peritoneal surface to revascularize the diaphragm; the skin to revascularize non-healing skin ulcers, such as diabetic ulcers; the pericardial surface to revascularize the pericardium; and the like.

IX. Timing of SVF Application

A transplant mixed with SVF cells or a transplant encapsulated with SVF cells can be "cultured" or "freshly isolated". If a transplant mixed with SVF cells or a transplant encapsulated with SVF cells is cultured, is typically incubated prior to implantation. For example, but not limited to, in a humidified incubator at 37° C. and 5% $CO_2$. Typically such cultured transplants mixed with SVF cells or a transplants encapsulated with SVF cells are incubated for a period of one hour to thirty days, but may be incubated for shorter or longer periods, as desired. The skilled artisan will appreciate that the term "cultured" may or may not refer to the use of conventional incubation methods, such as a controlled-temperature incubator.

Alternately, if a transplant mixed with SVF cells or a transplant encapsulated with SVF cells is freshly isolated, it refers to transplant mixed with SVF cells or a transplant encapsulated with SVF cells which comprises a freshly isolated SVF cells. A skilled artisan will appreciate that freshly isolated SVF cells can, but need not, be incubated for a prior time before being used in a transplant mixed with SVF cells or a transplant encapsulated with SVF cells as disclosed herein. In certain embodiments, a freshly isolated transplant mixed with SVF cells or freshly isolated transplant encapsulated with SVF cells can comprise SVF cells on, or within a three-dimensional culture that has been "incubated" subsequent to the introduction of the SVF cells, for example, but without limitation, to allow the construct to polymerize. In other embodiments, a freshly isolated transplant mixed with SVF cells or freshly isolated transplant encapsulated with SVF cell can comprises a liquid three-dimensional culture, as may be appropriate for implantation by injection (see, e.g., U.S. Pat. Nos. 5,709,854 and 6,224,893). Such liquid constructs may, but need not, polymerize in situ under appropriate conditions.

A skilled artisan will appreciate the advantages of using freshly isolated SVFs for production of freshly isolated transplant mixed with SVF cells or freshly isolated transplant encapsulated with SVF cells. For example, because of the nature of transplantation procedures, a transplant recipient may need a transplantation of a tissue or cell transplant immediately, due to the nature of the disease or condition, or the availability of the tissue or cell transplant from a donor subject. In such instances it may be impracticable to culture transplant mixed with SVF cells or transplant encapsulated with SVF cell prior to transplantation, as this may reduce the viability of the cells/tissue to be transplanted, or in certain circumstances risk the health or life of the recipient subject. Accordingly, one embodiment provides use of fresh SVF cells, either from the donor subject or from the recipient subject for encapsulating the transplant tissue or cells or mixing with the transplant tissue or cells, where the combination of SVF cells and transplant tissue or cells is immediately transplanted into the recipient subject.

X. Genetically Engineered SVF for Delivery of Additional Therapeutics to the Transplant Site In some embodiments, SVF cells used in methods to produce transplants mixed with SVF cells or transplants encapsulated with SVF cells are genetically modified. Methods to genetically engineer SVF cells are disclosed in U.S. application Ser. No. 12/511,940, filed on Jul. 29, 2009 which is incorporated herein in its entirety by reference.

Human SVF cells can be genetically engineered to generate cells that constitutively express human gamma interferon ($\gamma$-IFN), essentially as described by Stopeck et al., Cell Transplantation 6:18, 1997. The human SVF cells can be resuspended in M199 supplemented with 20% heat-inactivated FBS, 5 mM HEPES, 1.7 mM L-glutamine, and 60.mu.g/mL endothelial cell growth supplement (Jarrell et al., J. Vasc. Surg. 1:757 64, 1984) containing 25.mu.g/mL heparin and plated on gelatin coated polystyrene T-25 tissue culture flasks and incubated in a conventional humidified 37° C., 5% $CO_2$ incubator and maintained in culture.

Supernatants of high titer ($1\times10^6$–$1\times10^7$ cfu/mL) recombinant retrovirus containing either the E. coli beta-galactosidase ($\beta$-gal) or human $\gamma$-IFN gene were obtained from Viagene, Inc. (San Diego, Calif.). These recombinant retroviruses comprise a Moloney murine leukemia virus genome with viral structural genes replaced by either the $\beta$-gal or the human $\gamma$-IFN gene. T-25 flasks of human endothelial cells at 30 40% confluency are transduced for 6 18 hours on 2 consecutive days with media containing 750 μg/mL protamine sulfate and retrovirus supernatants at a multiplicity of infection of 5.

Forty-eight hours after transduction, cells are fixed with 2% formaldehyde prior to staining with X-gal solution (5 mM potassium ferricyanide, 5 mM potassium ferrocyanide, 2 mM $MgCl_2$, and 1 mg/,L X-gal (Sigma, St. Louis, Mo.) in PBS overnight at 37° C. The transduction efficiency is calculated as the number of cells staining positive for β-gal divided by the total number of cells counted. β-gal transduced or human γ-IFN transduced endothelial cells are selected using 1 mg/mL G418 (Gibco BRL) selection medium.

Total RNA is extracted from transduced and control endothelial cells using Trizol (Gibco BRL) for RT-PCR analysis, as described. Human endothelial cells transduced according to this procedure reportedly produce 80-130 pg/mL of human γ-IFN per $10^5$ cells after 24 hours in culture (see Stopeck et al., Cell Transplantation 6:18, 1997 and U.S. Pat. No. 5,957,972).

The skilled artisan will understand that replacement of the human γ-IFN or β-gal gene in these recombinant retrovirus vectors with alternate genes of interest requires only routine manipulation using techniques generally known in the art. Thus, any number of genes of interest may be transduced into and expressed by endothelial cells following this exemplary technique. The skilled artisan will also understand that, following techniques generally known in the art, a variety of mammalian cells can routinely be transduced or transfected to express virtually any gene product of interest (see, e.g., Twyman, Advanced Molecular Biology: A Concise Reference, Bios Scientific Publishers, Springer Verlag New York, particularly Chapter 24). Particularly useful gene products of interest include, for example, but without limitation, cytokines, insulin, human growth hormone, plasminogen activator, soluble CD4, Factor VIII, Factor IX, von Willebrand Factor, urokinase, hirudin, interferons, including α-, β- and γ-interferon, tumor necrosis factor, interleukins, hematopoietic growth factor, antibodies, glucocerebrosidase, adenosine deaminase, phenylalanine hydroxylase, human growth hormone, insulin, erythropoietin, VEGF, angiopoietin, hepatocyte growth factor, PLGF, and other proteins or gene products appropriate for local or systemic delivery, particularly blood-borne delivery.

Genetically engineered cells, particularly genetically engineered SVF cells, may be incorporated into the transplant mixed with SVF cells or transplant encapsulated with SVF cells of the invention at appropriate concentrations, as described. The skilled artisan that a wide variety of techniques may be used to genetically modify cells, i.e., transferring genes and nucleic acids of interest into recipient cells, using techniques generally known in the art, including, but not limited to: transfection (e.g., the uptake of naked nucleic acid), for example, but not limited to polyethylene glycol transfection, chemical transfection (e.g., using calcium phosphate and DEAE dextran), lipofection, electroporation, direct injection, and microballistics; and transduction, using a number of viral vectors, such as, without limitation, adenovirus vectors, herpesvirus vectors, retrovirus vectors, including, but not limited to lentivirus vectors. Descriptions of such techniques may be found in, among other places, Ausubel et al., Current Protocols in Molecular Biology (including supplements through March 2002), John Wiley & Sons, New York, N.Y., 1989; Sambrook et al., Molecular Cloning: A Laboratory Manual, 2nd Ed., Cold Spring Harbor Laboratory Press, Cold Spring Harbor, N.Y., 1989; Sambrook and Russell, Molecular Cloning: A Laboratory Manual, 3rdEd., Cold Spring Harbor Laboratory Press, Cold Spring Harbor, N.Y., 2001; Beaucage et al., Current Protocols in Nucleic Acid Chemistry, John Wiley & Sons, New York, N.Y., 2000 (including supplements through March 2002); Short Protocols in Molecular Biology, 4th Ed., Ausbel, Brent, and Moore, eds., John Wiley & Sons, New York, N.Y., 1999; Davis et al., Basic Methods in Molecular Biology, McGraw Hill Professional Publishing, 1995; Molecular Biology Protocols (see the highveld.com website), Protocol Online (protocol-online.net); and Twyman, Advanced Molecular Biology: A Concise Reference, Bios Scientific Publishers, Springer-Verlag New York.

In some embodiments of the present invention may be defined in any of the following numbered paragraphs:

1. A method of enhancing vascularization of a tissue or cell transplant in a subject, comprising;
    a. encapsulating the tissue or the cell transplant with a population of stromal vascular fraction (SVF) cells;
    b. implanting the tissue or the cell transplant encapsulated with a population of stromal vascular fraction (SVF) cells into a subject, wherein the SVF enhances vascularization of the tissue or the cell transplant in the subject.
2. The method of paragraph 1, wherein the population of SVF cells are present on the surface of, or embedded within, a biocompatible three-dimensional culture matrix.
3. The method of paragraph 2, wherein biocompatible three-dimensional culture matrix comprises additional cells.
4. The method of paragraphs 2 or 3, wherein biocompatible three-dimensional culture matrix comprises microvessel fragments.
5. The method of paragraph 4, wherein the microvessel fragments are obtained from adipose tissue.
6. The method of any of paragraphs 1 to 5, wherein the population of cells to be transplanted is present on the surface of, or embedded within, a biocompatible three-dimensional culture matrix.
7. The method of paragraph 6, wherein the population of cells to be transplanted which is present on the surface of, or embedded within a biocompatible three-dimensional culture matrix further comprises microvessel fragments.
8. The method of any of paragraphs 1 to 7, wherein the biocompatible three-dimensional culture matrix does not comprise other types of cells or tissue fractions than SVF cells.
9. The method of paragraph 1, wherein the SVF cells are contacted directly with the tissue or the cell transplant.
10. The method of any of paragraphs 1 to 9, wherein the SVF cells are obtained from the subject.
11. The method of any of paragraphs 1 to 9, wherein the SVF cells are obtained from a tissue or cell transplant donor.
12. The method of any of paragraphs 1 to 11, wherein the population of SVF cells and the tissue or cell transplant are from different species.
13. The method of any of paragraphs 1 to 12, wherein the SVF cells are human SVF cells.
14. The method of any of paragraphs 1 to 12, wherein the tissue or cell transplant is mammalian.
15. The method of paragraph 14, wherein mammalian tissue or cell transplant is human.
16. The method of any of paragraphs 1 to 15, wherein the SVF cells are genetically engineered.
17. The method of any of paragraphs 1 to 15, wherein the tissue or cell transplant is a genetically engineered tissue or cell transplant.
18. The method of any of paragraphs 1 to 8, wherein the SVF cells are attached to a tissue or cell transplant.

19. The method of paragraph 18, wherein attaching comprises suturing, stapling, gluing and combinations thereof.
20. The method of paragraph any of paragraphs 1 to 19, wherein the population of SVF cells is a substantially pure population of SVF cells.
21. The method of any of paragraphs 1 to 20, wherein the population of SVF cells are derived from adipose tissue.
22. A method of enhancing vascularization of a tissue or cell transplant in a subject, comprising;
    c. combining a population of stromal vascular fraction (SVF) cells with tissue or cell transplant to form a transplant mixed with SVF cells,
    d. implanting the transplant mixed with SVF cells into the subject, wherein the SVF cells enhance the vascularization of the tissue or cell transplant in the subject.
23. The method of paragraph 22, wherein the transplant mixed with SVF cells is a heterogeneous mixed population SVF cells with a tissue or cell transplant.
24. The method of paragraph 22 or 23, wherein the transplant mixed with SVF cells is present on the surface of, or embedded within a three-dimensional biocompatible matrix.
25. The method of any of paragraphs 22, 23 or 24, wherein the transplant mixed with SVF cells further comprises additional populations of cells.
26. The method of any of paragraphs 22, 23, 24 or 25, wherein the transplant mixed with SVF cells does not comprise microvessel fragments.
27. The method of any of paragraphs 22 to 26, wherein the transplant mixed with SVF cells does not comprise other types of cells or tissue fractions other than SVF cells and cell transplant cells.
28. The method of any of the paragraphs 22 to 27, wherein the transplant mixed with SVF cells present on the surface of, or embedded within a biocompatible three-dimensional culture matrix is combined with a tissue, organ or cell mass to be transplanted.
29. The method of paragraph 28, wherein combining the transplant mixed with SVF cells comprises attaching at least one transplant mixed with SVF cells to a tissue or cell transplant.
30. The method of paragraph 29, wherein attaching comprises suturing, stapling, gluing and combinations thereof.
31. The method of any of paragraphs 22 to 30, wherein the population of SVF cells is a substantially pure population of SVF cells.
32. The method of any of paragraphs 22 to 31, wherein the population of s SVF cells are derived from adipose tissue.
33. The method of any of paragraphs 22 to 32, wherein the SVF cells are obtained from the subject.
34. The method of any of paragraphs 22 to 32, wherein the SVF cells are obtained from a tissue or cell transplant donor.
35. The method of any of paragraphs 22 to 33, wherein the population of SVF cells and the tissue or cell transplant are from different species.
36. The method of any of paragraphs 22 to 35, wherein the SVF cells are human SVF cells.
37. The method of any of paragraphs 22 to 35, wherein the tissue or cell transplant is mammalian.
38. The method of paragraph 37, wherein mammalian tissue or cell transplant is human.
39. The method of any of paragraphs 22 to 38, wherein the SVF cells are genetically engineered.
40. The method of any of paragraphs 22 to 39 wherein the tissue or cell transplant is a genetically engineered tissue or cell transplant.
41. A composition comprising a tissue or cell transplant and a population of stromal vascular fraction (SVF) cells, wherein the population of SVF cells are attached to the outer surface of the tissue or cell transplant.
42. The composition of paragraph 41, wherein the population of SVF cells is a single cell layer or a multiple cell layer.
43. The composition of paragraphs 41 or 42, wherein the a single cell layer or a multiple cell layer of SVF cells substantially covers the outer surface of the tissue or cell transplant.
44. The composition of paragraphs 41, 42 or 43, wherein the a single cell layer or a multiple cell layer of SVF cells covers at least 50% of the outer surface of the tissue or cell transplant.
45. The composition of any of paragraph 41, 42 or 43, wherein the a single cell layer or a multiple cell layer of SVF cells covers at least 70% of the outer surface of the tissue or cell transplant.
46. The composition of any of paragraph 41, 42 or 43, wherein the a single cell layer or a multiple cell layer of SVF cells covers at least 80% of the outer surface of the tissue or cell transplant.
47. The composition of any of paragraph 41, 42 or 43, wherein the a single cell layer or a multiple cell layer of SVF cells covers at least 90% of the outer surface of the tissue or cell transplant.
48. The composition of paragraph 41, wherein the population of SVF cells is present on the surface of, or embedded within a three-dimensional matrix.
49. The composition of paragraphs 41 or 48, wherein the population of SVF cells present on the surface of, or embedded within a three-dimensional matrix substantially covers the outer surface of a tissue or cell transplant.
50. The composition of any of paragraph 41, 48 or 49, wherein the population of SVF cells present on the surface of, or embedded within a three-dimensional matrix covers at least 50% the outer surface of a tissue or cell transplant.
51. The composition of any of paragraph 41, 48 or 49, wherein the population of SVF cells present on the surface of, or embedded within a three-dimensional matrix covers at least 70% the outer surface of a tissue or cell transplant.
52. The composition of any of paragraph 41, 48 or 49, wherein the population of SVF cells present on the surface of, or embedded within a three-dimensional matrix covers at least 80% the outer surface of a tissue or cell transplant.
53. The composition of any of paragraphs 41, 48 or 49, wherein the population of SVF cells present on the surface of, or embedded within a three-dimensional matrix covers at least 80% the outer surface of a tissue or cell transplant.
54. The composition of any of paragraphs 41, 48 to 53, wherein the population of SVF cells present on the surface of, or embedded within a three-dimensional matrix comprises additional cells.
55. The composition of paragraph 54, wherein the population of SVF cells present on the surface of, or embedded within a three-dimensional matrix comprises microvessel fragments.
56. The composition of paragraph 54, wherein the population of SVF cells present on the surface of, or embedded within a three-dimensional matrix does not comprise microvessel fragments.

57. The composition of any of paragraphs 41 to 56, wherein the tissue or cell transplant and the SVF cells are from different species.
58. The composition of any of paragraphs 41 to 57, wherein the SVF cells are mammalian.
59. The composition of any of paragraphs 41 to 58, wherein the SVF cells are human.
60. The composition of any of paragraphs 41 to 59, wherein the SVF cells are genetically engineered.
61. The composition of any of paragraphs 41 to 57, wherein the tissue or cell transplant is mammalian.
62. The composition of any of paragraphs 41 to 61, wherein the tissue or cell transplant are human.
63. The composition of any of paragraphs 41 to 62, wherein the tissue or cell transplant is genetically engineered.
64. The composition of any of paragraphs 41 to 64, wherein the tissue or cell transplant is a tissue engineered tissue.
65. The use of the composition of paragraph 41 to 64, for transplantation into a subject.

Although the invention has been described with reference to various applications, methods, and compositions, it will be appreciated that various changes and modifications may be made without departing from the invention. The foregoing examples are provided to better illustrate the invention and are not intended to limit the scope of the invention.

EXAMPLES

Example 1

Beta cell replacement by islet transplantation is an emerging alternative to conventional insulin replacement therapy in the treatment of Type 1 diabetes (Ty.1 DM), especially in cases with poor glycemic control causing secondary complications (1, 2). Emerging approaches to islet implants include direct implantation at compatible sites, encapsulation, or immunoisolation devices. Such hypoxic and diffusion limited environments with a subsequent loss of cell-cell or cell-extracellular matrix (ECM) contacts represent a challenging state for freshly implanted islets.

Consequently, a major obstacle in its clinical utilization is islet death in the early post-implantation period. Furthermore, a lack of proper cell-matrix interactions in the isolated islets can destabilize the islets and trigger apoptosis (3). Substantial evidence supports the potentiation of angiogenesis by a heterogeneous population of cells derived by collagenase digestion of adipose tissue, called the stromal vascular fraction cells (SVFs) (4-7). Other cell preparations have been reported to evoke an angiogenic response and improve implant vascularization (8, 9). Interestingly, unlike use of other cells preparations, the inventors demonstrated that addition of SVFs increased the number of events of microvessels crossing a boundary between two collagen constructs. SVFs also increased the number of events of microvessels crossing a boundary between the islet—host tissue boundary in transplantation of β-cell. The need for immunoisolation of islets to avoid immunosuppressants poses challenges in maintenance of islet viability. SVFs have a demonstrated anti-apoptotic role (5) while encapsulation of islets in SVFs, host derived or otherwise, serves a purpose to reduce immunogenicity based on an earlier report describing a lower HLR antigen expression by cultured SVFs (10). The inventors demonstrate encapsulating or investing the islet microvasculature with SVFs prior to islet isolation. The presence of SVFs in association with islets has at least four advantages; (i) can help islet stability, (ii) viability, (iii) early revascularization, and (iv) reduce immunogenicity.

The inventors have demonstrated improved islet stability, viability and function by association with SVFs. The inventors demonstrate that the presence of SVFs, as an encapsulating layer or an internal microvascular investing layer, improve stability and promote early revascularization of islets. The inventors have discovered improved viability in islets retaining some parent cell and ECM cover. Thus, the inventors demonstrate that an external cellular layer of SVFs plays a role in cell-cell contact and signaling, ECM production, and cytokine secretion, thus increasing islet stability. Islet viability and function has been evaluated in vitro in presence of SVFs in normoxic and hypoxic conditions as seen post implantation.

The inventors demonstrate accelerated revascularization of implanted islets by association with SVFs. SVFs were shown to potentiate the crossing of host or implant vascular elements across the islet boundary and accelerate vascularization. SVFs also were shown to affect an accelerated revascularization response in the islets, likely by a cytokine dependant mechanism. SVFs injected in the pancreatic microcirculation prior to isolation also limit its de-endothelization or promote re-endothelization. Revascularization and function of SVF associated islets in a mouse implantation model was also evaluated.

Inflammation and immunogenicity of transplanted islets by association with SVFs has been reduced. Host derived SVFs encapsulating and re-endothelizing islets shield implanted islets from inflammation and immune rejection. Use of host derived SVFs serves to limit inflammation and immune rejection occurring primarily at the intraislet capillary endothelium while simultaneously promoting stability and early vascularization. Implanting SVF associated Sprague Dawley rat islets in both SCID mice and Fisher rats in appropriate configurations will elucidate the role of SVFs in reducing inflammation and rejection.

Almost 6% of the developed world's population has diabetes, a metabolic disorder of insulin deficiency and consequent hyperglycemia (12). Type 1 diabetes mellitus (Ty.1DM) is an autoimmune disease affecting the insulin secreting β-cells in the islets of Langerhans, leading to hyperglycemia and related complications. Traditional therapeutic management consists chiefly of restoring the metabolic homeostasis with exogenous insulin. In many cases however, this is insufficient for optimal control and leads to rapid swings in blood glucose levels and in some cases even to hypoglycemic shock episodes. About 10% of the Ty.1DM population is extremely sensitive to insulin and may lack proper glucagon response or other countermeasures and are at severe risk of hypoglycemia (12). Additionally, about a third of Ty.1a diabetics suffer from severe hypoglycemia requiring the intervention of another person about 1.3 times a year (13).

Alternatives to this therapy include insulin pumps, inhalational insulin, whole pancreas transplantation and islet transplantation (12). The goal of whole organ or purified islet transplantation is to produce a sustainable, exogenous insulin independent euglycemic state. Islet transplants gained attention due to their perceived ease of implantation over whole organ transplants but soon lost momentum due to failure of early procedures in inducing external insulin independence and graft rejection. The success of the Edmonton protocol for islet implantation has infused new excitement in this field and prompted numerous studies on free islet transplants and bioartificial pancreas.

The outcome of islet transplantation hinges on a critical islet mass, usually higher than the estimated islet equivalents (1E) and early revascularization of the implanted islets to leave behind at least of 26% β cell mass (14). Causes of failure of islet and other cell-based transplantation include hypoxia due to poor vascularization, loss of trophic support (15-17), non-specific inflammation, autoimmunity, reduced β-cell replication rates (18), and the host metabolic environment (19), and decreased viability post-transplantation. The immediate post-transplant environment is severely hypoxic and challenging. For example, typical post implantation oxygen tension in the islets is about 25% of the native endogenous islets (pO2, 40 mm Hg) (12) and does not improve significantly with time (20, 21). There is an attenuated, but reversible, reduction in the magnitude of the second phase insulin response with hypoxia, which is culture time dependent, and at least pO2 of 40-60 mm Hg is required to maintain islet secretory response (22). Almost 60% islet cell death post implantation within 3-6 months necessitates multiple implants (18, 23). Hence it is not surprising that islet transplantation has not yet become the treatment of choice in Ty1.DM. Islet transplantation is also being considered for Ty.2DM with a paradigm shift towards islet cell insufficiency from 'insulin-receptor resistance' theory (24). The substantial shortage of donor islets, poor transplantation results with cultured islets, and the requirement for multiple islet transplants to attain insulin independence limits clinical utility of this procedure. In its present form, islet transplantation can only benefit about 0.5% of all potential patients (13). Hence, Islet culture prior to transplantation may eventually become an inevitable process given the logistics of multiple organ donor management. Currently however, islet culture is associated with a reduction of mean islet mass (IE) (14) and may adversely impact their function post implantation (25). But culture of islets for a short time after isolation reduces the transfer of exocrine tissue contaminants and possibly its immunogenicity (26).

Although the islets constitute only about 1-2% of pancreatic tissue volume, they receive almost 15-20% of the organ blood flow (27). Freely implanted islets are heavily dependent on the post-transplantation revascularization process, which in freshly implanted islets, proceeds fairly quickly (28, 29) and may resemble that of native islets (28). However the hemodynamics and functional vascular density of the revascularized islets are not quite the same as the native islets and approach only a small fraction of this perfusion state (30), especially with cultured islets when the vascular density drops to 15% of the endogenous values within 7 days (31). At best they take on the characteristic hemodynamics of the local host vascular bed at the implantation site (21). Hence, improvement in implant site vascularity and co-implantation with modified cell types is now considered to improve revascularization with microencapsulation (32).

The role of peri-islet tissue and islet size in this revascularization process is unclear with studies suggesting better vascularization with peri-islet tissue and with smaller islets (29, 30). Only 30% of vasculature in such grafts was found associated with endocrine tissue compared to the non-endocrine and connective tissue parts (20, 21) possibly due to a selective loss of intra-islet endothelial lining. Freshly isolated islets retain their intra-islet capillary network endothelial cells (EC), which rapidly disappears even with overnight culture, and consequently are not revascularized fully until 7 days post-implantation (33, 34). Depending on the model, there is a variation in the amount of host and source ECs that may get incorporated into the new network endothelium (35). Further, a layer of endothelial cells has been reported around freshly isolated islets after portal injection (36), but this may not necessarily indicate better vascularity of islet substance (21, 37). The host-islet interface is the preferential area for active angiogenesis (34, 35, 38) in revascularizing islets with a significant amount of vasculature contributed by donor endothelial cells (ECs) in addition to the host-graft inosculation which was considered the primary mechanism (28, 29, 39). Thus, a preformed host derived endothelial cell or progenitor cell layer could hasten the process of revascularization when combined with maintenance of intra-islet endothelial cell (EC) lining Early phase of angiogenesis is involves increased proteolytic activity (40), which can improve islet vascular density post implantation (31). The inventors have previously demonstrated SVFs have a potentiating effect on vascular outgrowth across a collagen-collagen construct interface. Herein, the inventors demonstrate that the angiogenesis potentiating role of SVFs is critical for islet revascularization.

It is well known that the extracellular matrix (ECM) is responsible for transmission of both chemical and mechanical signals. Intact mature islets are normally surrounded by an incomplete cellular capsule and the associated collagen and laminin rich ECM (3). Inside the islets they are localized along the capillaries (3). The β-cells also associate with vessels by a basement membrane (BM) interface (41, 42). This BM is destroyed in the isolation process3 but is replaced by similar matrix proteins in a few days in culture (41). Islet ECM influences its stability and survival as discussed by Stendhal (42, 43). Islets retaining some native ECM have markedly reduced apoptotic rates and better function (23). Addition of RGD peptides or anti β1-integrin antibodies reduced islet cell death (3). The β-cells in the interior may not physically have such ECM contacts until revascularization and may be dependent on appropriate intercellular signaling (3, 42) or cytokines like IGF-II (17), EGF, FGF and VEGF (31, 44, 45). Cells immobilized on the islet surface in an attempt to increase biocompatibility do not lead to central necrosis (11). This leads to the conclusion that cell-ECM, cell-cell, and the mechanical forces transmitted to islets from this external cells on the basement membrane are essential for its stability and function and prevention of anoikis (23). Thus an ideal strategy will provide both cellular and ECM contacts to the outside and inside of the islets. A layer of cells allowed to grow on the islet periphery over a collagen IV and laminin layer can provide the cell-cell contacts for cells at the islet periphery, and their matrix and growth factor secretion, and contractile activities could satisfy the hitherto unknown requirements of these islets in culture. An investing layer of cells in the intra-islet vasculature would potentially serve a similar purpose and gradually provide seed elements for a quicker re-endothelization and revascularization of these cultured islets.

Stromal vascular fraction cells (SVFs) obtained by collagenase digestion of adipose tissue represent a heterogeneous population of cells which on culture in specific conditions can differentiate into endothelial cells. They also secrete cytokines and anti-apoptotic factors, especially in hypoxic states (5), integrate with preformed vessels, spontaneously form vessel like structures (4, 5, 46, 47), and protect against oxidative stress (48). Adipose derived stem cells (ADSC), isolated by plating the initial SVFs on plastic (49), can be driven to form islet like aggregates raising an interesting possibility that some of the SVFs used to encapsulate or invest the islets, especially the ones in close proximity to the beta cells, by virtue of local growth and maturation factors, could be directed to form islet like masses or incorporated into the pancreatic islet mass (50). Recently, Figliuzzi et al., demonstrated improved pancreatic islet function by co-implantation with mesenchymal stem cells (MSCs) which promoted a 30% graft vascularization (51) while use of SVFS in ischemic myocardium improved local vascularity and cardiac function (7). The different mechanisms by which SVF cells modulate cell behavior and exert their protective role is unclear, but their plasticity (52) and role in implant facilitator cannot be ignored.

The endothelium is a target of humoral and cellular immune rejection in transplantation (53). Similarly, immune rejection in Ty.1 diabetes is focused on the islet microvasculature (54). Innate immunity, inflammation and apoptosis result in significant islet death post implantation (12). Reduction of islet death and destabilization contribute to improving implant outcome by reducing the initial islet requirements, reducing the antigenic tissue exposed by destabilizing islets, and by reducing release of pro-inflammatory factors. An immuno-protective role for MSCs has been envisaged based on their suppressive action on allogenic T-cells (55, 56), suppression of dendritic cell antigen presentation, and promoting activity of suppressor T-cells (57). It is thus possible that SVFs, allogenic more than autologous (57), by virtue of their stem cell content will elicit a similar immunosuppressive response. The proposed encapsulation and microvascular investment of islets with SVFS will thus serve multiple simultaneous roles by preventing apoptosis, improving islet stability, promoting angiogenesis and inosculation with host vasculature, while also providing local immunosuppression due to their colocalization with native islet endothelium as SVFs get incorporated into the islet structure.

Experimental Data

The inventors have demonstrated that insulin secreted by the islets seeded in a collagen matrix is free to diffuse out from the collagen constructs. This is a relevant finding given that the inventor's approach involves seeding islets, microvessels, and SVFS in a collagen matrix and ex-vivo glucose challenge tests. The microvessels obtained from rat adipose tissue by partial collagenase digestion spontaneously forms sprouts when seeded in 3D collagen gels leading to a network formation by 10-14 days (FIG. 1). This model of angiogenesis from preformed vessel elements resembles a more physiological angiogenic process rather than the tube formation assays based on single cells.

Perfusion capability of islets after implantation in vascularized collagen construct.

Hiscox (58) demonstrated a close association between islets and such microvessel sprouts suggesting that islets may revascularizing when implanted between prevascularized constructs. To demonstrate that islets implanted in this fashion in the subcutaneous space were indeed perfused, the inventors have carried out these studies by seeding a mix of islets and microvessels in Ty.1 collagen, and polymerizing this solution between two pre-cultured (Day 7) vascularized constructs. The constructs were implanted in dorsal subcutaneous pouches of 6-8 wk old SCID mice for 14 days. Prior to explantation, the mice were either perfused with rhodamine labeled dextran or exanguinated and perfused with India ink, to highlight the perfusion capable vessels and the total connected vasculature within the constructs. Explants were dehydrated in sucrose and cryosectioned to get 20 µm thick sections. The sections clearly reveal the high degree of vascularization of the islets by India ink perfusion which showed several vessels within the islet mass containing ink. Dextran perfused islets show a vessel entering the islet (FIG. 2). This demonstrates the perfusion capability of islets when implanted subcutaneously in our system.

Role of SVFs in creating a permissive environment for host and implant microvessel sprout inosculation—Tissue engineered implants as well as tissue transplants always generate an interface with the host site when implanted. A successful revascularization event requires that microvessels from the host and/or implant cross this host-implant boundary. Though this process is relevant to understanding the early revascularizing events in the implanted islets, either within a 3D carrier substrate or direct hepatic delivery, it has not yet been studied. The inventors developed a model of this interface where a preformed microvessel construct is surrounded by a freshly prepared collagen gel polymerized around this central vascularized core. The inventors have demonstrated a 'deflection' of microvessels sprouts as they near this interface. An analogous situation can be envisaged in vivo, where microvessels sprouting from the adjoining tissue fail to penetrate the islets and only limited inosculation occurs. These inosculations may be stochastic occurrences, which can be maximized for early vascularization. However, addition of SVFs to the vascularized constructs induced a crossing of microvessels across this boundary, demonstrating that addition of SVFs to engineered constructs or surfaces can enhance the vascularization response (FIG. 3).

Benefits of using SVFs with microvessels in islet implants.

The inventors demonstrated that the addition of SVFs as well as microvessel fragments, improved islet vascularity when co-implanted as a vascularized construct in female SCID mice. The inventors have shown that addition of SVFs accelerates the vascularization process which can be observed over time using the proposed window chamber model. The presence of preformed vessels will only further potentiate this activity.

Islet transplantation is better than whole pancreas transplantation in patients with Ty.1DM given the comparative ease of the procedure and lesser morbidity (25). β-cell mass decreases by almost ⅔rd in transplanted islets while the endocrine non-beta cell mass remains stable (18). High initial islet requirements ($10^6$ islets avg.) and the need for secondary islet implants (59) hinder widespread clinical applicability. Multiple portal injections carry the risk of portal vein thrombosis. If a single donor is insufficient for transplantation, a successful in vitro culture process can maintain the islets until another donor is processed. Other roadblocks to the use of islet implantation include impaired revascularization, islet death, or compromised function by inflammation or immune rejection.

The inventors have shown that it is possible to improve islet stability and survival in culture by providing an encapsulating cellular layer to satisfy the cell-cell and cell-matrix interactions of the islets. Further, by injecting SVFs into the islet microcirculation, one can prevent denudation of the parent intraislet endothelium, and to quicken the re-endothelialization of these networks. ADSCs in this heterogeneous SVF cell population may also provide local immune-modulation. SVFs derived from the host or allogeneic sources can further ameliorate the immune-rejection. This proposal is designed to test the aforementioned aspects of inclusion of SVFs in islet culture and transplants while simultaneously promoting revascularization.

In the natural state, pancreatic islets exist surrounded by a relatively dense extracellular matrix and exocrine tissue. The interactions between islets and the surrounding cells and ECM are essential in prevention of apoptosis. These signals are transduced from the outside-in, to the β-cell rich islet core, and maintain the appropriate signaling to prevent apoptosis. Islet isolation releases the tension exerted by the surrounding ECM and cells on the islets, may influence its stability. Trophic support from the surrounding tissue is essential to prevent islet death. The inventors demonstrate that by recreating a cellular cover around islets, or providing close association with SVFs, provides sufficient trophic support for the transplanted islets and prevents islet death. Islet microvasculature endothelium is rapidly lost even within the first day of culture (33). Injecting heparinized SVFs into the islet microcirculation prior to isolation will deliver cells at this location where they may mitigate denudation of native endothelium and help in re-endothelization.

Methods:

The islet matrix is naturally rich in collagen Ty.IV and laminin, both of which can provide a pro-angiogenic environment (60, 61). Cell culture on microspheres, either static or rolling, is a well established (62). The inventors used the spheroidal pancreatic islets, isolated as described by Hiscox et al.(58), in lieu of microspheres, and generate a coat of SVFs over it by rolling co-culture for 24 hrs. The spreading and proliferation of SVFs on the islet surface will satisfy the need for cell-cell interactions and prevent islet death by apoptosis (48). The secretion of cytokines, deposition of new matrix, and contractile forces generated by the cells on the islet surface will serve to partially recreate the gamut of signals perceived by the islets in their native state. Tie-2 GFP rat derived adipose tissue yielding GFP-SVFs is used to differentiate native islet cells from the SVF generated coverage. Prior to collagenase injection into the pancreatic ducts, SVFs in heparinized DMEM are injected into the pancreatic microcirculation via the thoracic aorta after ligation of the abdominal aorta below the renal arteries. Delivery of SVFS into the islet microvasculature can be confirmed, for example, by using GFP SVFs. Islets are equilibrated in equilibration medium for about 2 hrs and cultured for about 10 days in high glucose DMEM with 10% FBS. Islets are examined for SVF derived coverage, viability, intraislet microvascular endothelial coverage, and an in vitro glucose challenge test on days 1, 3, 5, and 7. Confocal microscopy is used to reconstruct 3D images of islets stained for insulin (Alexa 633 secondary antibody), endothelial cells (GS1-Rhodamine), GFP-SVFs, and nuclei (DAPI). Generation of the SVF shell is described as % coverage in area and relative depth. Insulin and nuclear staining will reveal areas of central necrosis if any. GS1 labeled endothelial cells (EC) lining the intraislet microvasculature will be differentiable from the injected GFP-SVF derived cells. The ratios of parent EC retention vs. EC from GFP-SVFs will be an index of efficacy of the SVF association process and will be compared over time. Non-SVF associated islets will be used as controls. A similar set of islets will be examined for insulin response to a glucose challenge test in vitro (58). SVF associated islets will be compared on the 7th day of culture in normoxic and hypoxic conditions to mimic implantation.

In some instances, where the SVFs forms an incomplete layer surrounding the pancreatic islets in the 24 hr rolling culture period, expand coverage to a multicellular layer can subsequently occur by static culture. Injected SVFs are expected to associate with the host microvessel endothelium. Reduction of parent endothelium is paralleled by an increased incorporation of GFP-SVFS. The viability and response to glucose challenge are better in SVF associated islets than in controls, with retention of response characteristics over duration of culture. Addition of SVFS may improve viability, and function under hypoxia.

Coating of islets with SVFs can serve as an enabling technology in pancreatic islet implantation.

Current strategies involve shipping the whole pancreas in a shipping medium (single of dual layered) followed by isolation and implantation. However, this procedure is presently ineffective in rendering islet implantation commonplace in clinical practice, namely due to high numbers of islet death immediately post implantation, and the requirement of a large number of seeding islets to attain desired survival and function post-implantation. The inventors overcome this issue, and demonstrate herein, that coating the whole pancreas or parts of the pancreas with SVF cells can directly influence this process by allowing collection of islets from multiple donors and culturing them until required for implantation or β-cell isolation and implantation. Thus, coating tissues or cells to be implanted with SVFs is useful to promote their survival, for example, during travel from the donor location to the recipient location and prior to implantation into the recipient. As an added advantage, the use of SVFs to coat cells and/or tissues allows for formation of an angiogenesis induction capable cell layer on the islet surface and will maintain the intraislet microvasculature. Additionally, in some embodiments, where the SVFs used to coat the tissue (e.g. pancreas) are originally obtained from the recipient host, this serves as an added advantage of reducing host versus graft disease and immune rejection of the transplanted tissue or cells.

Lack of revascularization and loss of intraislet microvascular EC architecture is a primary cause of early post-implantation death. Freshly isolated islets on implantation show sprouts by the 2nd day and initial circulation only by the 6th day (28, 29, 33). Even such brief periods of ischemia can be detrimental to the function of surviving islets (25). Thus, the inventors demonstrating that associating SVFs with islets on the outside, as well in the microvasculature, improves the revascularization response. In addition to the role in islet stability and viability, incorporating SVFs with the islets primes the islets for revascularization by secretion of angiogenic growth factors and maintaining a healthier quantum of surviving or re-established intraislet ECs. Based on the inventors data demonstrating vessels growing across a collagen-collagen construct interface with the addition of SVFs, an increased number of microvessels growing across the host-islet interface is seen by the permissive actions of SVFs. Without wishing to be bound by a theory, the inventors demonstrate that presence of microvessel elements in the SVF-islet implant construct further facilitates revascularization.

Methods

Islet revascularization will be examined in a dorsal skinfold window chamber. Islets from GFP rats (green cells) are coated or invested with SVFS from mRFP mice (red cells), seeded in collagen Ty.1 gels and implanted subcutaneously in 6-8 wk old female SCID mice. Fluorescently labeled dextran are administered by tail vein injections at 3, 7, 10, and 14 days and imaged to determine the progression of functional perfusion and relative contributions of various components of this system to islet revascularization. Constructs with only islets, and those containing islets+microvessels, or islets+SVFS+microvessels, are used as controls to evaluate the relative efficacy of the procedures. In the latter, constructs for the window chamber contain microvessels from mice with blue fluorescent protein. Injection of dextran is followed by injection of glucose to determine any local increase in perfusion at the implant site, denoting a functional response of the implanted islets to a glucose challenge. In terminal experiments, fluorescently labeled microbeads are used instead of dextran to characterize changes in flow dynamics in the islet constructs. Similar constructs from SD rats explanted at the same time points will be used for histomorphometric quantification of vessel density, cellularity, and insulin response to glucose challenge ex vivo. One animal per time point is used for ink casting of constructs post vasodilatation to get true vessel density, which can be higher than functional density.

SVF associated islets revascularize faster than islets only or islets with microvessels. Islet vascularity and blood flow alterations with glucose challenge is established quicker in SVFS+microvessel containing constructs due to existence of the preformed vessel elements to promote network formation. However, SVF associated islets perform better than remaining groups indicating an advantage of a well-vascularized environment. Histomorphometric data reveals a higher number of parent EC retention as well as a quicker re-endothelization of intraislet microvessel networks with SVF derived ECs.

Demonstration of improved revascularization in the presence of SVFS, with or without added microvessels, will be a major step in the current paradigm for islet implantation. It not only improves integration of islets by the current portal delivery system, but also provide easier alternative routes for islet delivery like the subcutaneous tissue or omentum. The demonstration of improved microvessel communication across the islet-host tissue barrier also has far reaching consequences for implanted tissue or devices in general where the existence of such an interface is generally ignored. Recent evidence by Provenzano et al. and others suggest that this is indeed a non-trivial problem in implant design and integration (63-65).

Even with development of improved immunosuppressive and anti-inflammatory treatments, islet death post implantation remains high. Though inadequate vascularization is the primary cause, a significant number of islets are lost to both nonspecific inflammation induced by partly digested islets, and specific innate or cellular immunity. Islet immunogenicity however may reduce after a few days in culture (26). The presence of mesenchymal stem cells (MSCs) of allogenic bone marrow origin has been shown to reduce inflammation and immunogenicity in several studies. MSCs themselves have been shown to lose specific antigenic epitopes in culture. Encapsulation of islets with SVFs provides a shield to reduce to its immunogenicity. Since the islet endothelium is the primary site of immune rejection reactions, presence of SVFs is beneficial. Further, host derived SVFS can even completely envelope the islets and abrogate the foreign body/antigen response against the implanted allogenic or xenogeneic islets.

Islets from SD rats are associated with GFP-SVFs on the outside and at the intraislet endothelium, cultured for 5 days, and implanted in dorsal subcutaneous pouches of 6-8 wk old female SCID mice or female Fisher rats for 14 days. The SCID mice lack an immune response but have an inflammatory response while the Fisher rats are non-immunogenic for allogenic transplants (islets coated with Fisher rat derived SVFs). This experiment allows the separation of inflammatory and immune responses. Islets obtained from SD rats but without SVF association are used as controls. Constructs are explanted on the 14th day and examined for inflammatory cells, vascularity, and islet viability. A separate construct implanted in the same animals but only containing the xenogeneic ECs is used as a control for islet specific confounding factors if any.

SVF associated islets perform better than non-SVF controls. No immune rejection of SD rat islets implanted into Fisher rats is seen when they are encapsulated and invested with SVFs. Non-SVF associated islets in Fisher rats are destroyed by immune rejection.

Successful reduction in inflammation and immune rejection by use of allogeneic or autologous SVFs in encapsulating implants can reduce the number of islets required for achieving insulin independence. Further, such an approach has wider applicability in other implant models as well, where a localization of cells on the host-contacting surface can help in graft integration, and prevent fibrous capsule formation.

References for Example 1

Reference numbers in brackets "(#)" refer to the references listed in Example 1 are listed below. All references, patents and patent applications cited herein and throughout the specification are herewith incorporated by reference in their entirety.
1. Ricordi, C., et al., Islet transplantation and results. 2009. p. 913-20.
2. Guyton, A. C., Textbook of medical physiology. 8 ed. 1991: W. B. Saunders Company.
3. Pinkse, G. G., et al., Integrin signaling via rgd peptides and anti-beta1 antibodies confers resistance to apoptosis in islets of langerhans. Diabetes, 2006. 55(2): p. 312-7.
4. Planat-Benard, V., et al., Plasticity of human adipose lineage cells toward endothelial cells: Physiological and therapeutic perspectives. Circulation, 2004. 109(5): p. 656-63.
5. Rehman, J., et al., Secretion of angiogenic and antiapoptotic factors by human adipose stromal cells. Circulation, 2004. 109(10): p. 1292-8.
6. Yamamoto, N., et al., Isolation of multipotent stem cells from mouse adipose tissue. J Dermatol Sci, 2007. 48(1): p. 43-52.
7. Li, B., et al., Adipose tissue stromal cells transplantation in rats of acute myocardial infarction. Coron Artery Dis, 2007. 18(3): p. 221-7.
8. Rubina, K., et al., Adipose stromal cells stimulate angiogenesis via promoting progenitor cell differentiation, secretion of angiogenic factors, and enhancing vessel maturation. Tissue Eng Part A, 2009.
9. Fumimoto, Y., et al., Creation of a rich subcutaneous vascular network with implanted adipose tissue-derived stromal cells and adipose tissue enhances subcutaneous grafting of islets in diabetic mice. Tissue Eng Part C Methods, 2009.
10. McIntosh, K., et al., The immunogenicity of human adipose-derived cells: Temporal changes in vitro. Stem Cells, 2006. 24(5): p. 1246-53.
11. Teramura, Y., et al., Islet encapsulation with living cells for improvement of biocompatibility. Biomaterials, 2009. 30(12): p. 2270-5.
12. Merani, S., et al., Current status of pancreatic islet transplantation. Clin Sci (Lond), 2006. 110(6): p. 611-25.
13. Shapiro, J. A. M., Islet transplantation and beta cell replacement therapy. CRC Press, 2007.
14. Matsumoto, S., et al., Evaluation of engraftment after single islet transplantation from a brain-dead donor by the secretory unit of islet transplant objects (suito) index. Transplantation proceedings, 2008. 40(2): p. 364-6.
15. Davalli, A. M., et al., Vulnerability of islets in the immediate posttransplantation period. Dynamic changes in structure and function. Diabetes, 1996. 45(9): p. 1161-7.

16. Tenniswood, M. P., et al., Active cell death in hormone-dependent tissues. Cancer Metastasis Rev, 1992. 11(2): p. 197-220.
17. Ilieva, A., et al., Pancreatic islet cell survival following islet isolation: The role of cellular interactions in the pancreas. J Endocrinol, 1999. 161(3): p. 357-64.
18. Davalli, A. M., et al., A selective decrease in the beta cell mass of human islets transplanted into diabetic nude mice. Transplantation, 1995. 59(6): p. 817-20.
19. Biarnes, M., et al., Beta-cell death and mass in syngeneically transplanted islets exposed to short- and long-term hyperglycemia. Diabetes, 2002. 51(1): p. 66-72.
20. Andersson, A., et al., Promoting islet cell function after transplantation. Cell Biochem Biophys, 2004. 40(3 Suppl): p. 55-64.
21. Carlsson, P. O., et al., Oxygen tension and blood flow in relation to revascularization in transplanted adult and fetal rat pancreatic islets. Cell transplantation, 2002. 11(8): p. 813-20.
22. Dionne, K. E., et al., Effect of hypoxia on insulin secretion by isolated rat and canine islets of langerhans. Diabetes, 1993. 42(1): p. 12-21.
23. Thomas, F. T., et al., Anoikis, extracellular matrix, and apoptosis factors in isolated cell transplantation. Surgery, 1999. 126(2): p. 299-304.
24. Halban, P. A., Cell therapy for type 2 diabetes: Is it desirable and can we get it? Diabetes, obesity & metabolism, 2008. 10 Suppl 4: p. 205-11.
25. Ryan, E. A., et al., Clinical outcomes and insulin secretion after islet transplantation with the edmonton protocol. Diabetes, 2001. 50(4): p. 710-9.
26. Kedinger, M., et al., In vitro culture reduces immunogenicity of pancreatic endocrine islets. Nature, 1977. 270(5639): p. 736-8.
27. Lifson, N., et al., Blood flow to the rabbit pancreas with special reference to the islets of langerhans. Gastroenterology, 1980. 79(3): p. 466-73.
28. Menger, M. D., et al., Angiogenesis and hemodynamics of microvasculature of transplanted islets of langerhans. Diabetes, 1989. 38 Suppl 1: p. 199-201.
29. Menger, M. D., et al., Revascularization and microcirculation of freely grafted islets of langerhans. World J Surg, 2001. 25(4): p. 509-15.
30. Kampf, C., et al., Size-dependent revascularization of transplanted pancreatic islets. Cell transplantation, 2006. 15(2): p. 205-9.
31. Olsson, R., et al., Revascularization of transplanted pancreatic islets following culture with stimulators of angiogenesis. Transplantation, 2006. 82(3): p. 340-7.
32. de Groot, M., et al., Causes of limited survival of microencapsulated pancreatic islet grafts. J Surg Res, 2004. 121(1): p. 141-50.
33. Mendola, J. F., et al., Immunocytochemical study of pancreatic islet revascularization in islet isograft. Effect of hyperglycemia of the recipient and of in vitro culture of islets. Transplantation, 1994. 57(5): p. 725-30.
34. Nyqvist, D., et al., Donor islet endothelial cells participate in formation of functional vessels within pancreatic islet grafts. Diabetes, 2005. 54(8): p. 2287-93.
35. Brissova, M., et al., Intraislet endothelial cells contribute to revascularization of transplanted pancreatic islets. Diabetes, 2004. 53(5): p. 1318-25.
36. Hirshberg, B., et al., Histopathological study of intra-hepatic islets transplanted in the nonhuman primate model using edmonton protocol immunosuppression. The Journal of clinical endocrinology and metabolism, 2002. 87(12): p. 5424-9.
37. Lau, J., et al., Low revascularization of human islets when experimentally transplanted into the liver. Transplantation, 2009. 87(3): p. 322-5.
38. Linn, T., et al., Angiogenic capacity of endothelial cells in islets of langerhans. FASEB J, 2003. 17(8): p. 881-3.
39. Vajkoczy, P., et al., Histogenesis and ultrastructure of pancreatic islet graft microvasculature. Evidence for graft revascularization by endothelial cells of host origin. Am J Pathol, 1995. 146(6): p. 1397-405.
40. Krishnan, L., et al., Interaction of angiogenic microvessels with the extracellular matrix. Am J Physiol Heart Circ Physiol, 2007. 293(6): p. H3650-8.
41. Wang, R. N., et al., Characterization of integrin expression in islets isolated from hamster, canine, porcine, and human pancreas. J Histochem Cytochem, 1999. 47(4): p. 499-506.
42. Stendahl, J. C., et al., Extracellular matrix in pancreatic islets: Relevance to scaffold design and transplantation. Cell transplantation, 2009. 18(1): p. 1-12.
43. Nagata, N. A., et al., Co-culture of extracellular matrix suppresses the cell death of rat pancreatic islets. J Biomater Sci Polym Ed, 2002. 13(5): p. 579-90.
44. Stagner, J. I., et al., Induction of angiogenesis by growth factors: Relevance to pancreatic islet transplantation. EXS, 1992. 61: p. 381-5.
45. Hayek, A., et al., The use of digital image processing to quantitate angiogenesis induced by basic fibroblast growth factor and transplanted pancreatic islets. Microvasc Res, 1991. 41(2): p. 203-9.
46. Nakagami, H., et al., Novel autologous cell therapy in ischemic limb disease through growth factor secretion by cultured adipose tissue-derived stromal cells. Arterioscler Thromb Vasc Biol, 2005. 25(12): p. 2542-7.
47. Madonna, R., et al., In vitro neovasculogenic potential of resident adipose tissue precursors. Am J Physiol Cell Physiol, 2008. 295(5): p. C1271-80.
48. Kim, W. S., et al., Evidence supporting antioxidant action of adipose-derived stem cells: Protection of human dermal fibroblasts from oxidative stress. J Dermatol Sci, 2008. 49(2): p. 133-42.
49. Halvorsen, Y. D., et al., Thiazolidinediones and glucocorticoids synergistically induce differentiation of human adipose tissue stromal cells: Biochemical, cellular, and molecular analysis. Metabolism, 2001. 50(4): p. 407-13.
50. Chandra, V., et al., Generation of pancreatic hormone expressing islet like cell aggregates from murine adipose tissue-derived stem cells. Stem Cells, 2009.
51. Figliuzzi, M., et al., Bone marrow-derived mesenchymal stem cells improve islet graft function in diabetic rats. Transplant Proc, 2009. 41(5): p. 1797-800.
52. Scherberich, A., et al., Three-dimensional perfusion culture of human adipose tissue-derived endothelial and osteoblastic progenitors generates osteogenic constructs with intrinsic vascularization capacity. Stem Cells, 2007. 25(7): p. 1823-9.
53. Banz, Y., et al., Endothelial cell protection in xenotransplantation: Looking after a key player in rejection. Xenotransplantation, 2006. 13(1): p. 19-30.
54. Petruzzo, P., et al., Pancreatic islet microcirculation: A scanning electron microscopic study of corrosion casts. Transplantation proceedings, 1997. 29(4): p. 2050-1.
55. Maitra, B., et al., Human mesenchymal stem cells support unrelated donor hematopoietic stem cells and suppress t-cell activation. Bone Marrow Transplant, 2004. 33(6): p. 597-604.

56. Tse, W. T., et al., Suppression of allogeneic t-cell proliferation by human marrow stromal cells: Implications in transplantation. Transplantation, 2003. 75(3): p. 389-97.
57. Rasmusson, I., Immune modulation by mesenchymal stem cells. Experimental cell research, 2006. 312(12): p. 2169-79.
58. Hiscox, A. M., et al., An islet-stabilizing implant constructed using a preformed vasculature. Tissue Eng Part A, 2008. 14(3): p. 433-40.
59. Markmann, J. F., et al., Insulin independence following isolated islet transplantation and single islet infusions. Ann Surg, 2003. 237(6): p. 741-9; discussion 9-50.
60. Kidd, K. R., et al, Laminin-5-enriched extracellular matrix accelerates angiogenesis and neovascularization in association with eptfe. J Biomed Mater Res A, 2004. 69(2): p. 294-304.
61. Williams, S. K., et al., Covalent modification of porous implants using extracellular matrix proteins to accelerate neovascularization. J Biomed Mater Res A, 2006. 78(1): p. 59-65.
62. Shivakumar, K., et al., Synthetic hydrogel microspheres as substrata for cell adhesion and growth. In Vitro Cell Dev Biol, 1989. 25(4): p. 353-7.
63. Karamichos, D., et al., Complex dependence of substrate stiffness and serum concentration on cell-force generation. J Biomed Mater Res A, 2006. 78(2): p. 407-15.
64. Provenzano, P. P., et al., Collagen reorganization at the tumor-stromal interface facilitates local invasion. BMC Med, 2006. 4(1): p. 38.
65. Brown, R. A., et al., Ultrarapid engineering of biomimetic materials and tissues: Fabrication of nano- and microstructures by plastic compression. Advanced Functional Materials, 2005. 15(11): p. 1762-70.

Example 2

The regulatory processes involved when a new vessel sprout traverses complex tissue environment are critical in determining its final architecture. Such complex environments are commonly encountered at tissue or organ boundaries or even within a tissue like muscles, where there is a regional variation in properties. It is still unclear why a neovascular bed has a defined architecture. In addition to the soluble factors and cytokines, local variations in mechanical properties and ECM alignment may direct this process. Similarly, there is a mismatch between engineered constructs and the surrounding host tissue.

The interfacial nature of such a 'barrier' of mismatched properties in tissue is not well recognized. The inventors demonstrate a change in direction of a neovessel sprout approaching an interface between two vascularized constructs. It is unclear whether this change in direction and apparent 'barrier' like behavior is due to a change in orientation of the matrix fibers at this interface, due to local change in stiffness, or if it is due to limited remodeling capacity of cells. A similar behavior can be expected of neovessels in vivo as they approach an implant interface or in wound healing where vessels penetrate a provisional fibrin matrix. The inventors investigate that both matrix stiffness and local extracellular matrix (ECM) orientation determine the neovascular sprouting, morphology, and orientation, both differentially and in a temporal sequence. The inventors used an in vitro vascularized constructs which were generated with different ECM densities, defined orientation cues for contact guidance, and an overlay of contact guidance and mechanical forces to delineate the relative importance of contact guidance and mechanical signals in determining microvascular morphology. Further, the inventors used a plug and field model of vascularized constructs comprising SVF cells to demonstrate a transitional interface, as occurs in vivo.

In vivo, growing neovessels are exposed to multiple competing stimuli like cytokines, other soluble factors, changing tissue stiffness, and an aligned matrix (ECM). Furthermore, these stimuli may be presented at areas of transition between different tissue units or within a single tissue unit like the transition of muscle body to a tendon. A growing vessel senses these multiple competing stimuli in addition to flow, and is ultimately guided to its final tissue architecture. To understand the development of such complex vascular architecture it is essential to study the regulatory mechanisms that dictate the orientation, branching, and other morphological features of neovascular networks. Based on current literature relating to angiogenesis, the inventors have discovered that mechanical loading and contact guidance as the primary determinants of this process. This 'mismatch' in properties is also a significant problem in implantation of engineered constructs which may have distinct lamellae at the interfacial surfaces[10,11] with possible regional variations in mechanical properties. The inventors have recently demonstrated that where a neovessel sprout is deflected at such an interface reinforces the possibility of interfacial properties affecting cellular behavior. It is unknown if this phenomenon is a result of difference in stiffness or ECM fiber orientation. Taken in context of revascularization of transplants or engineered grafts, and in growth of new vessels into complex tissue, this interface assumes significance as a possible barrier. It is thus essential to study the influence of matrix stiffness, its orientation, and the interaction between the two stimuli to understand how the neovessel morphology and direction in angiogenesis is regulated. Knowledge of these interactions can provide insights into the development of organized vasculature in vivo and is also critical to engineering better transplant-host tissue integration strategies.

Significant evidence supports a direct or indirect influence of mechanical loading on cells[12-16]. Matrix rigidity can influence the formation of endothelial cord like structures in vitro[17-19] possibly by the relaxation of ECM contacts of endothelial cells[20] Sprouting angiogenesis in itself alters the stiffness of ECM, while external loading or contraction against fixed anchors caused an increase in the number of branching events in microvascular networks[21,22]. The orientation field in response to neovessel growth has not been evaluated in detail, although the inventors have previously demonstrated a correlation with vessel alignment[23]. Further, it must be considered that a disturbance in mechanical homeostasis in itself can be a sufficient trigger to control initial sprout morphology and branching[3,20,24]. Further Lo et al. report a preferential migration of cells into stiffer matrices or higher density matrix at interfaces[25,26]. Crosslinking ECM, which increases its stiffness and limits orientation, can also influence angiogenesis[27,28]. To understand the relative contributions of each of these factors to development of the final vascular architecture, it is necessary to isolate the two stimuli at least in a temporal fashion. The inventors have used the orientation field developed due to neovascular growth as an indicator of the amount of tractional forces generated by neovessels and compared the results across different densities as well as in orientation restricted crosslinked matrices to identify the dominant regulatory influence on neovessel morphology.

Cell orientation can be achieved by ridges and grooves on patterned surfaces[5, 6] or by orientation of matrix fibrils[29]. Neovessels can similarly grow along the matrix guidance pathways generated by cell traction[30, 31]. Matrix orientation at the interface may determine the ability of neovessels to cross an interface. In fact, Provenzano et al. have demonstrated a difference in local collagen fiber structure associated with invasive or non-invasive nature of tumor cells in a collagen matrix in vitro[32] However once contact guidance based orientation is established, further reorientation is limited even in single cells[33]. An alignment of neovessels can be achieved by electrospun collagen fibers, but the effect of strain may be seen as an increased branching in the direction of strain in an attempt to minimize or redistribute the part of the vasculature exposed to the principal strain direction as postulated by Eastwood et al.[7].

Addition of cells to the prevascularized constructs adds multiple small foci of cellular traction. Based on the 'two-center' theory proposed by Wolfe, this can lead to the formation of multiple small discrete traction fields between these single cells[9, 34]. This could not only provide a mechanical stimulus for neovessel growth, but also provide provisional ECM guidance channels based on the interpretation of recent data by Provenzano et al.[32]. Additionally, the inventors herein demonstrate that EVC (also referred to as SVFs herein) improve the revascularization of grafts in vitro and in vivo by providing cytokines.

Effect of Stiffness on Microvessels[35]

To demonstrate the role of matrix stiffness in regulation of vascular architecture, the inventors investigated how changing matrix density and thus its stiffness influenced the neovascular network architecture during early angiogenesis. Microvessel fragments from rat epididymal fat pad was minced, partially digested with collagenase and seeded at a density of 20,000 fragments/ml in Ty.1 collagen at 3 different collagen concentrations (1.5, 3, 5 mg/ml) shown to differ in stiffness[36]. Sprouting began on the 3rd day and continued to form in vitro networks. Cultures were fixed on the 5th day and stained with Alexa-488-GS1 lectin for endothelial cells. Confocal images were taken to a depth of 300 um from the surface, 3 um apart, and reconstructed with commercial software (Amira, Visage Imaging). The images were threshold, converted to a medial skeleton representation, and parsed through a custom program to get vessel morphology parameters of interest like vessel numbers, lengths, branching, and orientation[21]. The collagen fiber alignment around the growing neovessel sprouts were imaged by reflectance microscopy. The vessel 'bulk' and invading 'tip' areas were chosen for fiber orientation analysis based on the methods of Kirkpatrick et al.[37]. The orientation of fibers was evaluated in a 25 um area just adjacent to the vessel and another 25 um area adjacent to the first one i.e. 50 um from the vessel. The investigators demonstrated a significant difference in vessel network architecture with matrix density. Results show shorter, but more branched vessels at lower collagen concentrations. The matrix orientation field extended to a larger distance from the vessel tip at lower collagen density. With increasing collagen density there was an increase in vessel length and reduction in vessel numbers and branching. The larger fibril alignment field in the lower density matrix suggests that vessel mediated fibril orientation may influence neovessel guidance and length, but not necessarily regulate branch initiation. The results demonstrate that matrix stiffness, reflected by its malleability to orientation, by balancing the cell traction forces influences neovessel growth[3].

Behavior of Neovessel Sprouts at Interfaces

Growth of neovessels across a simple interface can be considered to simplistically approximate the traversing of complex tissue structures in vivo. Looking at angiogenesis at such an interface provides an opportunity to understand how different cues are interpreted during development of characteristic vascular architectures. Understanding how vessels behave at or near interfaces provides insights into the predominant regulatory mechanisms e.g. stiffness, orientation, chemokine gradients etc. The inventors created interfaces between vascularized-vascularized gel, vascularized-cell free gel, and vascularized-gluteraldehyde fixed gels by first polymerizing one gel in a 96 well plate and transferring it to a 48 well plate containing unpolymerized collagen with RFMF (microvessel fragments). Using this method, provides a good interface without apparent gaps. The significant findings were that the neovessel sprouts do not cross across any of the interfaces, but are instead deflected along the edges. Such a barrier like effect is consistent with an altered fibril orientation or 'skin' as reported by Karamichos et al. and others[10, 11, 32].

Behavior of Neovessel Sprouts at Interfaces when Co-Cultured with EVC (Also Termed SVF Cells)

The inventors demonstrated that the addition of a single cell population derived from the complete digestion of adipose tissue (Extravascular cells, EVC e.g. SVF cells) rather than partial digestion as for the microvessel fragments, can influence and significantly increase or accelerate the sprouting by providing more cytokines, increased matrilysis, or heightening the matrix remodeling in their vicinity. The inventors created an interface between a vascularized gel core and unvascularized collagen outside as before, with the difference that the vascularized gel core also had $10^6$ SVF cells. Significantly, by the 8th day of culture, events of microvessel sprouts crossing the interface were apparent. Using PHK26 labeled SVF, the inventors demonstrate that the SVF cells stayed within the substance of the core where they were seeded. Thus, the inventors demonstrate that the potentiating effect on enhancing neovessels crossing the interface a result of increased matrilysis causing matrix remodeling or creating multiple areas of local fibril reorientation[32] also acting as small nodes of matrix traction as a result of cellular contractility.

As a new vessel element traverses a complex tissue, it encounters variations in ECM stiffness, orientation, and chemokine gradients. The interpretation of these multiple cues by neovessels is not yet understood well. The inventors demonstrate that mechanical loading and matrix orientation are the major factors involved. The inventors used an in vitro vascularized construct to investigate these regulatory mechanisms. The inventors investigated Neovascular sprout orientation, branching and other parameters in a vascularized construct model with different collagen densities to understand the influence of matrix stiffness. Further, this model also enabled characterizing the response of neovessels to two competing or conflicting stimuli i.e. mechanical forces and contact guidance. Finally, addition of EVC provides information on how the surrounding cells as seen in vivo, like perivascular cells, smooth muscle cells or fibroblasts, guide the final vascular architecture.

Vascularized Constructs:

Adipose derived microvessel fragments (RFMF) isolated by partial collagenase digestion and seeded in Ty1. collagen gel[35, 38] form an ideal system to investigate the process of angiogenesis and understanding various regulatory mechanisms discussed earlier. Typically, sprouts begin to form spontaneously by the 3rd day of culture and progress to form perfusion capable networks when implanted[39]. The defining feature of this model is the use preformed microvessel elements rather than single cells. Though single cell models forming cord like structures are efficient to identify cell-cell signaling and other similar aspects, they must indeed be viewed as a model of vasculogenesis. Use of preformed microvessel elements is a closer approximation to the physiological processes and includes small arterioles, venules, and capillaries with appropriate perivascular cellular associations. Formation of vascularized constructs, confocal imaging, and ECM orientation analysis are detailed in earlier publications[21-23, 35, 37, 38].

Evaluation of the architecture of angiogenic microvessel sprouts in matrices of different density and the extent of fibril orientation. The inventors demonstrate that vascular morphology and neovessel induced ECM orientation correlate with changes in ECM stiffness with progressive neovessel growth. The reciprocal nature of the interaction between cell traction and substrate properties is well known[1, 2]. The inventors demonstrate that neovessel growth and branching is a determinant of the balance between cell tractional forces and the resisting forces by the ECM (referred to as tensional homeostasis). This tensional homeostasis[3, 4] may act as a switch governing the neovessel branching. The matrix alignment field reflects the amount of matrix remodeling necessary to attain this homeostasis. The inventors examined neovessel length, branching and alignment in comparison to this ECM orientation field in different density matrices at an early and late phase of angiogenesis to demonstrate the effect of ECM stiffness. Further, the inventors constrained the ECM orientation in these vascularized matrices by crosslinking or by anchorage and examined similar parameters to demonstrate that matrix orientation is necessary to regulate neovessel morphology or if any temporal sequence exists between cellular mechanical homeostasis and contact guidance from fibril orientation.

ECM orientation field in the vicinity of the growing sprout is the direct result of cellular contractile forces during sprout formation. The orientation field is thus dependant on the balance of forces between the cells and the collagen matrix; and stiffer the ECM, easier the attainment of this homeostasis. The inventors investigated if matrix orientation is a secondary process and may allow easier vessel elongation after the initial ECM alignment. Constraining alignment by crosslinking the ECM or by anchoring the constructs will interfere with mechanical homeostasis, and was used to differentiate matrix stiffness from matrix orientation.

Vascularized constructs at four different collagen concentrations known to vary in stiffness[36] will be analyzed at early (D4) and late phase (D8) of angiogenesis for vessel morphology and fiber orientation around growing sprouts. The field of ECM orientation around the vessel sprouts, and the vessel branching patterns in this vicinity will be compared across the different densities. Notch1 &Dll4 antibody labeling of construct cryosections will be performed to determine the extent of signals for vessel branching40. Variations in the orientation field and vessel growth with time will allow us to dissect the temporal sequence of prominence between these stimuli. Comparing these outcomes with those from constructs either treated with Glucose-6-Phosphate or anchored to steel meshes, allowing for mechanical homeostasis while limiting ECM orientation, will indicate the influence of matrix stiffness on vessel morphology and associated ECM orientation field.

The inventors have previously demonstrated longer vessels and positive Notch1-Dll4 staining with smaller ECM orientation fields at high density and high stiffness conditions. The inventors determined that when low density gels are anchored or crosslinked, the branching will be reduced, vessel length increased, and Notch1-Dll4 signaling increased with reduced ECM orientation field in the neovessel vicinity.

The inventors used crosslinking of the matrix to restrict ECM orientation, but this is sometimes difficult in the presence of microvessels in our 3D constructs. Crosslinked matrices may still be reversibly oriented[41] in which case destabilizing the actin cytoskeleton will reveal the extent of deformation[42]. As an alternative, constraining the constructs between stainless steel mesh anchors[21] could be done to serve a similar purpose.

Evaluation of the interplay between contact guidance and mechanical forces in neovessels. The inventors investigated if mechanical forces form the primary but transient cue whereas contact guidance is the secondary but lasting signal for determination of neovessel morphology and orientation. Cell migration and orientation along patterned surfaces and in strain fields are well known[5-8]. Cellular tractional forces also set up migratory tracts for further growth[9]. However, the relative dominance of either mechanical forces or of contact guidance in determining neovessel orientation, branching or morphology is unknown. To understand the behavior of neovessel sprouts under such dual cues, as may be commonly encountered in vivo, it is essential to know if these stimuli act in a concerted manner, if there is any time dependence, or if there is a differential sensing mechanism. The inventors evaluated this interdependence by subjecting microvessel constructs impregnated with an electrospun collagen mesh to uniaxial stretch at different times in the angiogenic process.

The role of contact guidance in tissue morphology may be secondary to mechanical homeostasis. The initiation of orientation could be due to mechanical stimuli, with contact guidance being the secondary cue. But once established contact guidance may be the governing stimulus in multicellular structures with superimposed mechanical stimuli causing secondary changes like increased proteolysis[33].

A coarse mesh of electrospun collagen fiber strands, either coated or uncoated with fibronectin, will provide contact guidance cues to sprouting neovessel. This mesh will be laid within the collagen gels in custom chambers with or without anchors to enable stretching of growing constructs as described earlier[21, 22]. The alignment of collagen fibrils in this model in response to addition of this electrospun coarse mesh, in the absence of vessels, will be used as a baseline control in fibril orientation imaging studies. This inventors performed this experiment with static free floating constructs at the four collagen concentrations (see FIG. 4). Further, a group of vascularized constructs at 3 mg/ml collagen density was allowed to grow for 5-7 days to establish robust neovessel sprouting and then subjected to 10% uniaxial static stretch. Neovessel morphology and branching both along and transverse to the direction of stretch, in the vicinity of the electrospun fibers was then compared. Notch1 & Dll4 antibody staining was repeated to correlate the induction of branching with stretch direction. Phenotypic switch of sprout 'stalk' cells to 'apical' cells[43] under stretch transverse to initial vessel alignment direction was studied in an environmental chamber by live imaging of growing microvessels from Tie2-GFP rats. Formation of filopodia by the 'stalk' cells will be the visual indicator prior to staining[43].

The inventors demonstrate that in that in the absence of any external mechanical forces like anchorage or stretch, neovessel sprouts grow along, and in close association with the electrospun fibers irrespective of ECM density and without significant differences in branching or alignment. However, under the influence of anchorage or external stretch, the response differs based on the time of application of uniaxial stretch. A pre-stretched construct was demonstrated to produce more neovessels in the direction of stretch but a construct stretched only after the neovessels are allowed to align along the electrospun fibers does not show such an orientation. Instead, the inventors demonstrate that these neovessels oriented along the electrospun fibers to show more branching when stretched transverse to alignment direction and longer vessels when stretched in the direction of alignment. Comparable observations have been reported for fibroblasts on patterned surfaces[44].

As an alternative to coarse electrospun collagen fibers, it is possible to use collagen fibrils oriented within an electric field[45] as the patterned substrate, with vessels growing into these oriented matrices from a juxtapositioned vascularized construct.

Characterization of the influence of SVF or EVC (extravascular cells) cells in enhancing a neovascular reorientation response under the two conflicting stimuli.

The inventors evaluated if SVF cells or EVCs create a permissive environment for neovessels to grow against a perceived orientation or stiffness barrier by matrix remodeling and generation of multiple local force gradients. Vascularization of implanted grafts or migration of cells to, and from an implant, is common in vivo. The inventors demonstrate both a perceived interface and a potentiating role of SVF cells or other EVC in neovessels crossing this barrier. The inventors determined that the SVF cells or other EVCs by virtue of matrilysis, matrix realignment, or by generating multiple areas of stress localization by their traction, potentiate both the transgression of this barrier as well as a reorientation of neovessels in the direction of strain field on a transversely aligned substrate.

Resistance of cells in multicellular structures to changing direction against an established contact guidance field may come from the organized ECM fibrils themselves forming a refractory or deflecting barrier. A similar deflection may occur due to a difference in ECM stiffness. Addition of extravascular cells (EVC) or SVF cells increases local proteolysis and generate myriad small tensional (traction) gradients influencing both the cells as well as the existing fiber orientations, thus generating a more permissive environment to enable an invasion and migration across this perceived barrier.

A 'plug and field' model with cell free collagen forming the field area and vascularized constructs with EVC ($0.5 \times 10^6$ cells) or SVF cells forming the central plug was used. The polymerization of collagen against a preformed construct in itself gives rise to an organized fibril barrier[10, 11] and was evaluated first against constructs without EVC or SVF cells. Next, a similar approach was used to characterize this phenomenon across an interface of different matrix densities (stiffness). Neovessels and EVC or SVF cells were allowed to grow for 5 days in the collagen gel with the coarse electrospun mesh as described herein and then subjected to uniaxial stretch (10%). The orientation, branching, and predominant sprout or branch direction of neovessels was evaluated within representative mesh grids at the specimen center and compared for variations with respect to both the aligned electrospun fibers and the direction of stretch. Total proteolytic activity was estimated using fluorogenic substrates as described earlier[22].

The inventor demonstrate more neovessels cross across the fiber orientation or stiffness barrier, and a larger number of neovessels reorienting in the direction of stretch and increased branching in the direction of stretch. The inventors also demonstrate local fiber remodeling by the EVC or SVF cells at the interface between constructs or at established fiber tracts.

The true cell type within the EVC or SVF cell population that enhances the number of neovessels across the interface could be due to endothelial cells, pericytes, and other cells from adipose tissue, or a combination thereof.

References for Example 2

Reference numbers which are superscript (e.g.[no]) refer to the references listed in Example 2 are listed below. All references, patents and patent applications cited herein and throughout the specification are herewith incorporated by reference in their entirety.

1. Sieminski, A. L., et al., The relative magnitudes of endothelial force generation and matrix stiffness modulate capillary morphogenesis in vitro. Exp. Cell Res., 2004. 297(2): p. 574-84.
2. Ingber, D. E., et al., Mechanochemical switching between growth and differentiation during fibroblast growth factor-stimulated angiogenesis in vitro: Role of extracellular matrix. J. Cell Biol., 1989. 109(1): p. 317-30.
3. Ingber, D., Tensegrity: The architectural basis of cellular mechanotransduction. Annu. Rev. Physiol., 1997. 59: p. 575-599.
4. Ingber, D. E., et al., How does extracellular matrix control capillary morphogenesis? Cell, 1989. 58(5): p. 803-5.
5. Dunn, G. A., et al., Alignment of fibroblasts on grooved surfaces described by a simple geometric transformation. J. Cell Sci., 1986. 83: p. 313-40.
6. Uttayarat, P., et al., Topographic guidance of endothelial cells on silicone surfaces with micro-to nanogrooves: Orientation of actin filaments and focal adhesions. J. Biomed. Mater. Res. A, 2005. 75(3): p. 668-80.
7. Eastwood, M., et al., Effect of precise mechanical loading on fibroblast populated collagen lattices: Morphological changes. Cell Motil. Cytoskeleton, 1998. 40(1): p. 13-21.
8. Neidlinger-Wilke, C., et al., Cell alignment is induced by cyclic changes in cell length: Studies of cells grown in cyclically stretched substrates. J. Orthop. Res., 2001. 19(2): p. 286-93.
9. Vernon, R. B., et al., Organized type i collagen influences endothelial patterns during "Spontaneous angiogenesis in vitro": Planar cultures as models of vascular development. In Vitro Cell Dev Biol Anim, 1995. 31(2): p. 120-31.
10. Karamichos, D., et al., Complex dependence of substrate stiffness and serum concentration on cell-force generation. J Biomed Mater Res A, 2006. 78(2): p. 407-15.
11. R. A. Brown, et al., Ultrarapid engineering of biomimetic materials and tissues: Fabrication of nano- and microstructures by plastic compression. Advanced Functional Materials, 2005. 15(11): p. 1762-1770.
12. Shyy, J. Y., Mechanotransduction in endothelial responses to shear stress: Review of work in dr. Chien's laboratory. Biorheology, 2001. 38(2-3): p. 109-17.
13. Chen, B. P., et al., DNA microarray analysis of gene expression in endothelial cells in response to 24-h shear stress. Physiol. Genomics, 2001. 7(1): p. 55-63.
14. Alenghat, F. J., et al., Mechanotransduction: All signals point to cytoskeleton, matrix, and integrins. Sci. STKE, 2002. 2002(119): p. PE6.
15. Muratore, C. S., et al., Stretch-induced upregulation of vegf gene expression in murine pulmonary culture: A role 16. Oddou, C., et al., Cell mechanotransduction and interactions with biological tissues. Biorheology, 2000. 37(1-2): p. 17-25.
17. Stephanou, A., et al., The rigidity in fibrin gels as a contributing factor to the dynamics of in vitro vascular cord formation. Microvasc Res, 2007. 73(3): p. 182-90.
18. Vailhe, B., et al., In vitro angiogenesis is modulated by the mechanical properties of fibrin gels and is related to alpha(v) beta3 integrin localization. In Vitro Cell Dev Biol Anim, 1997. 33(10): p. 763-73.
19. Ghajar, C. M., et al., The effect of matrix density on the regulation of 3-d capillary morphogenesis. Biophys J, 2008. 94(5): p. 1930-41.
20. Deroanne, C. F., et al., In vitro tubulogenesis of endothelial cells by relaxation of the coupling extracellular matrix-cytoskeleton. Cardiovasc. Res., 2001. 49(3): p. 647-58.
21. Krishnan, L., et al., Effect of mechanical boundary conditions on orientation of angiogenic microvessels. Cardiovasc Res, 2008. 78(2): p. 324-32.
22. Krishnan, L., et al., Interaction of angiogenic microvessels with the extracellular matrix. Am J Physiol Heart Circ Physiol, 2007. 293(6): p. H3650-8.
23. Underwood, C. J., et al. Quantification of temporal collagen and microvessel alignment induced by anchored boundary conditions during angiogenesis. in ASME Summer Bioengineering Conference. 2009. Squaw Creek Resort, Lake Tahoe, Calif.
24. Ingber, D. E., Mechanical signaling and the cellular response to extracellular matrix in angiogenesis and cardiovascular physiology. Circulation Research, 2002. 91(10): p. 877-87.
25. Lo, C. M., et al., Cell movement is guided by the rigidity of the substrate. Biophysical Journal, 2000. 79(1): p. 144-52.
26. Hsu, S., et al., Effects of shear stress on endothelial cell haptotaxis on micropatterned surfaces. Biochem. Biophys. Res. Commun., 2005. 337(1): p. 401-9.
27. Kuzuya, M., et al., Inhibition of angiogenesis on glycated collagen lattices. Diabetologia, 1998. 41(5): p. 491-9.
28. Howard, E. W., et al., Cellular contraction of collagen lattices is inhibited by nonenzymatic glycation. Exp Cell Res, 1996. 228(1): p. 132-7.
29. Guido, S., et al., A methodology for the systematic and quantitative study of cell contact guidance in oriented collagen gels. Correlation of fibroblast orientation and gel birefringence. J. Cell Sci., 1993. 105 (Pt 2): p. 317-31.
30. Davis, G. E., et al., Regulation of endothelial cell morphogenesis by integrins, mechanical forces, and matrix guidance pathways. Exp. Cell Res., 1995. 216(1): p. 113-23.
31. Takakuda, K., et al., Tensile behaviour of fibroblasts cultured in collagen gel. Biomaterials, 1996. 17(14): p. 1393-7.
32. Provenzano, P. P., et al., Collagen reorganization at the tumor-stromal interface facilitates local invasion. BMC Med, 2006. 4(1): p. 38.
33. Mudera, V. C., et al., Molecular responses of human dermal fibroblasts to dual cues: Contact guidance and mechanical load. Cell Motil Cytoskeleton, 2000. 45(1): p. 1-9.
34. Korff, T., et al., Tensional forces in fibrillar extracellular matrices control directional capillary sprouting. J. Cell Sci., 1999. 112 (Pt 19): p. 3249-58.
35. Krishnan, L., et al. Extracellular matrix stiffness modulates microvascular morphology during early sprouting angiogenesis in vitro. in ASME Summer Bioengineering Conference. 2009. Squaw Creek Resort, Lake Tahoe, Calif.
36. Krishnan, L., et al., Design and application of a test system for viscoelastic characterization of collagen gels. Tissue Eng, 2004. 10(1-2): p. 241-52.
37. Kirkpatrick, N. D., et al., Live imaging of collagen remodeling during angiogenesis. Am J Physiol Heart Circ Physiol, 2007. 292(6): p. H3198-206.
38. Hoying, J. B., et al., Angiogenic potential of microvessel fragments established in three-dimensional collagen gels. In Vitro Cell Dev Biol Anim, 1996. 32(7): p. 409-19.
39. Shepherd, B. R., et al., Rapid perfusion and network remodeling in a microvascular construct after implantation. Arterioscler Thromb Vasc Biol, 2004. 24(5): p. 898-904.
40. Hellstrom, M., et al., Dll4 signalling through notch1 regulates formation of tip cells during angiogenesis. Nature, 2007. 445(7129): p. 776-80.
41. Vader, D., et al., Strain-induced alignment in collagen gels. PLoS One, 2009. 4(6): p. e5902.
42. Wakatsuki, T., et al., Cell mechanics studied by a reconstituted model tissue. Biophysical Journal, 2000. 79: p. 2353-2368.
43. Gerhardt, H., et al., Vegf guides angiogenic sprouting utilizing endothelial tip cell filopodia. J Cell Biol, 2003. 161(6): p. 1163-77.
44. Loesberg, W. A., et al., The effect of combined cyclic mechanical stretching and microgrooved surface topography on the behavior of fibroblasts. J Biomed Mater Res A, 2005. 75(3): p. 723-32.
45. Cheng, X., et al., An electrochemical fabrication process for the assembly of anisotropically oriented collagen bundles. Biomaterials, 2008. 29(22): p. 3278-88.

The invention claimed is:

1. A composition comprising a tissue or cell transplant and a population of cells comprising stromal vascular fraction (SVF) cells, wherein the population of cells comprising SVF cells coats at least a portion of the outer surface of the tissue or cell transplant, wherein the SVF cells present on the surface of, or embedded within a three-dimensional matrix comprises microvessel fragments and wherein the population of cells comprising SVF cells are not cultured by incubation for a period of time prior to contracting the tissue of cell transplant.

2. The composition of claim 1, wherein the population of SVF cells substantially covers the outer surface of the tissue or cell transplant.

3. The composition of claim 2, wherein a single cell layer or a multiple cell layer of SVF cells covers at least 70% of the outer surface of the tissue or cell transplant.

4. The composition of claim 1, wherein the population of cells comprising SVF cells is present on the surface of, or embedded within a three-dimensional matrix, wherein the population of SVF cells contacts the tissue of the cell transplant.

5. The composition of claim 1, wherein the tissue or cell transplant is genetically engineered.

6. The composition of claim 1, wherein the tissue or cell transplant is a tissue engineered tissue.

7. The composition of claim 1 wherein inosculation is established post-transplantation.

8. The composition of claim 7 wherein establishing inosculation comprises a functional response to a glucose challenge.

\* \* \* \* \*